US005700354A

United States Patent [19]

Virnelson et al.

[11] Patent Number: 5,700,354
[45] Date of Patent: Dec. 23, 1997

[54] PAPER STRENGTHENED WITH SOLUBILIZED COLLAGEN AND METHOD

[75] Inventors: Kevin M. Virnelson, Mayfield Hts.; Kenneth E. Hughes, Gahanna; David C. Masterson, Grove City; David J. Fink, Shaker Hts.; Barbara A. Metz, Baltimore; Gordon E. Pickett, Reynoldsburg; Paul M. Gemmer, Port Clinton; Richard S. Brody, Worthington, all of Ohio

[73] Assignee: Ranpak Corp., Concord Township, Ohio

[21] Appl. No.: 479,175

[22] Filed: Jun. 7, 1995

Related U.S. Application Data

[63] Continuation-in-part of Ser. No. 250,806, May 27, 1994, abandoned, and Ser. No. 78,932, Jun. 16, 1993, Pat. No. 5,316,942.

[51] Int. Cl.$^6$ .......................... D21H 17/22; D21H 17/00
[52] U.S. Cl. .......................... 162/143; 162/135; 162/151; 162/157.6; 162/174; 162/180; 162/183; 162/184; 162/185; 435/68.1; 435/71.1; 435/184; 435/212; 435/213; 435/273; 530/356
[58] Field of Search .......................... 162/143, 135, 162/151, 157.6, 174, 180, 183, 184, 185; 435/68.1, 71.1, 184, 212, 213, 273; 530/356

[56] References Cited

U.S. PATENT DOCUMENTS

| 1,184,518 | 5/1916 | Clapp . | |
|---|---|---|---|
| 2,352,922 | 7/1944 | Thomas et al. | 92/21 |
| 2,637,321 | 9/1953 | Cresswell | 128/335.5 |
| 2,934,446 | 4/1960 | Highberger et al. | 106/155 |
| 2,934,447 | 4/1960 | Highberger et al. | 106/155 |
| 3,223,551 | 12/1965 | Tu | 117/140 |
| 3,314,861 | 4/1967 | Fujii | 195/6 |
| 3,532,593 | 10/1970 | Young | 162/2 |
| 3,592,925 | 7/1971 | Evans et al. | 424/119 |
| 3,616,205 | 10/1971 | Ito et al. | 195/6 |
| 3,907,779 | 9/1975 | DeBoer et al. | 260/211.5 R |
| 4,066,083 | 1/1978 | Ries | 128/325 |
| 4,140,537 | 2/1979 | Luck et al. | 106/155 |
| 4,220,724 | 9/1980 | Berg et al. | 435/273 |
| 4,233,360 | 11/1980 | Luck et a. | 428/310 |
| 4,293,647 | 10/1981 | Monsheimer et al. | 435/69 |
| 4,389,487 | 6/1983 | Ries | 435/273 |
| 4,488,911 | 12/1984 | Luck et al. | 106/161 |
| 4,565,580 | 1/1986 | Miyata et al. | 106/124 |
| 4,575,500 | 3/1986 | Burg et al. | 514/121 |
| 4,655,980 | 4/1987 | Chu | 264/102 |
| 4,703,108 | 10/1987 | Silver et al. | 530/356 |
| 4,883,864 | 11/1989 | Scholz | 530/356 |
| 5,021,406 | 6/1991 | Maeda et al. | 54/99 |
| 5,137,875 | 8/1992 | Tsunenaga et al. | 514/21 |
| 5,316,942 | 5/1994 | Fink | 435/273 |

FOREIGN PATENT DOCUMENTS

| 139458A | 5/1985 | European Pat. Off. . |
| 1145904 | 3/1963 | Germany . |
| 1062083 | 3/1964 | United Kingdom . |
| 2023613 | 1/1980 | United Kingdom . |
| 8103261 | 11/1981 | WIPO . |

OTHER PUBLICATIONS

The Preparation and Properties of Solubilised Collagens; N. T. Crosby et al; J. Soc. Lea. Trades Chemists; 46; 1962; pp.152–161.
Comminuted Collagen: Estimated Costs of Commercial Production; V.A. Turkot et al; Food Technology; Apr. 1978; pp.48–57.
The Use of Collagen Dispersions During the Manufacturing of Paper; J. Tkac et al; Kozarstvi 30; 11; 1980; pp.324–326.
The Science & Technology of Gelatin; Ward, A.G. & Courts, A.; Academic Press; 1977; pp.152–153, 164–167, 422–425.
Abstract 118126g, "Collagen & Collagen Solutions," Japan Leathaer Co., Ger. 1,145,904, Mar. 1963.
Hamill et al, "Glue as Beater Sizing," Paper Trade Journal, 55th year, pp. 32–37.
Calkin, "Modern Pulp & Papermaking," Reinhold Publishing Corp., pp. 269 and 312–313.
"Hide Glue for Tub Sizing," TAPPI, pp. 227–228.
"Relationship Between Collagen & Gelatin," pp. 152–153, 164–167, 176–177, 422–425.

*Primary Examiner*—Herbert J. Lilling
*Attorney, Agent, or Firm*—Renner, Otto, Boisselle & Sklar

[57] ABSTRACT

A method for making a collagen strengthened cellulosic sheet by providing a cellulosic pulp slurry; adding solubilized collagen to the pulp slurry, and mixing for a time effective for interaction of the cellulosic pulp slurry and solubilized collagen; forming the interacted cellulosic pulp slurry and solubilized collagen into a sheet; and drying the sheet; also, a method for using solubilized collagen for strengthening paper by mixing the solubilized collagen with a cellulosic pulp slurry; and making a cellulosic pulp product from the mixture and drying.

10 Claims, 4 Drawing Sheets

PAPER STRENGTHENED WITH SOLUBILIZED COLLAGEN AND METHOD

The present invention is a continuation-in-part application of Ser. No. 08/250,806, filed May 27, 1994, now abandoned, and a continuation-in-part application of Ser. No. 08/078,932 filed Jun. 16, 1993 now U.S. Pat. No. 5,316,942.

FIELD OF THE INVENTION

This invention relates to a process for making solubilized collagen and for making solubilized collagen-strengthened paper that provides advantages over other known processes that make improved papers. The invention also relates to the improved solubilized collagen and improved paper made by the process. The invention has utility in making low cost solubilized collagen and in binders for cellulosic products, especially in the production of recycled cellulosic paper that has improved mechanical properties and low cost.

The present invention is related to the application entitled RECYCLE PROCESS FOR THE PRODUCTION OF LOW-COST SOLUBLE COLLAGEN having Ser. No. 08/250,803, filed May 27, 1994, currently pending the disclosure of which is incorporated by reference herein.

BACKGROUND OF THE INVENTION

The processing of animal hides to produce leather is an ancient art, and today it is a very mature industry. Excellent references to the chemistry of leather manufacture by McLauglin, G. D., et al, *The Chemistry of Leather Manufacture*, Reinhold Publishing Corp, N.Y. (1945), and collagen reactivity by Gustavson, K. H., *The Chemistry and Reactivity of Collagen*, Academic Press Inc., N.Y. (1956), date from the 1940's and 1950's, and are still basic descriptions of the art practiced today. The name "collagen" is derived from the Greek word for glue, as is the term "colloid" which means "gluelike" in Greek.

Skin is composed of four distinct layers, which are, proceeding from outside-in: (1) a thin outer layer of epithelium termed the "epidermis", which is rich in the protein keratin, not collagen; (2) a dense collagen-rich layer, termed the "dermal" or "grain" layer, also called in the older literature the "thermostat" layer; (3) a thicker layer of less-dense, collagen-rich connective tissues, termed the "corium" layer; and (4) an inner layer of "subcutaneous tissue", known to the tanner as "flesh", by which the skin is attached to the underlying tissue.

Although hides may merely be "cured" in salt and/or other biocidal solutions to stop microbial degradation, many hides that are intended for use in leather manufacture are "limed", that is, soaked in a saturated solution of hydrated lime (calcium hydroxide) and water. The liming process initiates the loosening of the epidermis and the subcutaneous layer, and is the first step in the dehairing process. After liming is complete, the hair, epidermis, and any residual flesh, fat and surface muscles are removed by mechanical scraping, and the dermal layer is mechanically cut, along with enough of the corium layer to give the final leather its required thickness, from the remaining inner corium layer.

In leather-making the primary interest is on the dense collagen-rich dermal layer, which is about 25% of the thickness of the corium layer. During the process of leather-making, the dermal tissue receives separate chemical and tanning treatments to stabilize the collagen structure.

The residual portion of the corium layer that is separated from the dermal layer is termed the "limed split" and is a by-product waste of the leather manufacturing process. It is these limed splits that become, for example, the collagen-rich feedstock for sausage casing production, and that have been used as the source of collagen for the examples herein.

During the liming process, the skin imbibes and binds water, and becomes highly swollen; in the process it acquires a very alkaline pH of about 12.5. The chemistry of the liming process is quite well understood. Prior to further leather processing, and in the collagen production process considered here, the skins must be "delimed" by soaking in acid or salt solutions.

Recycling of cellulosic materials to preserve natural resources and reduce costs is presently a desirable environmental objective. The recycled cellulosic materials are preferably used to replace end products where virgin cellulosic materials have historically been used. Unfortunately, products made from recycled cellulosic materials usually have physical characteristics that differ from those made from virgin materials. One of these important characteristics is strength which is often significantly reduced.

Previous attempts to provide increased strength to paper include that disclosed in the Young, U.S. Pat. No. 3,532,593. Young describes a mechanical method for isolating preexisting gelled collagen fibers, not an enzymatic method for solubilizing the collagen as in the present invention. This patent describes a method for removing fat from collagen. The collagen is mechanically treated by beating in an acid solution but remains insoluble. The insoluble mechanically treated collagen was then combined with cellulose beaten pulp and made into paper sheets.

A French journal article by G. Sauret et al, Le collagne ans la fabrication du papier, Revue A.T.P.I., Vol 33, No. 8, Octobre 1979, pp 374–365, discloses a mechanical method using a Turmix-Waring blender for preparing collagen. The mechanically treated collagen is insoluble. It is combined with cellulose pulp and made into paper sheets.

In contrast, the present invention uses a method that combines small amounts of soluble collagen with cellulosic material as further described herein.

SUMMARY OF THE INVENTION

A typical embodiment of the invention is a method for producing an aqueous solution of solubilized collagen by the steps of (a) providing an aqueous ground slurry of insoluble collagen and adjusting the pH of the slurry to obtain activity for a later added proteolytic enzyme; (b) adding the proteolytic enzyme to the pH adjusted slurry; (c) reacting the slurry and enzyme of step b and or recycled insoluble collagen and enzyme of step e at a temperature, T, and for a time, t, effective for forming a solution increased in solubilized collagen; (d) adding additional water and insoluble collagen to the solution of step (c) and mixing; (e) separating at least some of the solution of step d containing solubilized collagen from the insoluble collagen, whereby at least a portion of the insoluble collagen and proteolytic enzyme is recycled to step c, and a separated solution containing solubilized collagen is withdrawn as product. Another typical embodiment does not employ the recycle step but uses the solubilized collagen directly without removal of enzyme. Typically step c may be repeated two, three, four or more times. Additional enzyme may be added to the recycled insoluble collagen from step e that substantially replaces enzyme removed with the withdrawal of product or when the rate of reaction on recycling decreases below a predetermined level. In one typical embodiment, the method is operated as a continuous process.

The reaction may typically be stopped by adjusting the pH to that where the proteolytic enzyme is substantially inactive; and/or by reducing the temperature to that where the proteolytic enzyme is substantially inactive. In another typical embodiment in step a, the liquid or solids content of the wet ground slurry is preferably adjusted so that the solids are at a concentration of about 0.1 to about 1.0 wt %; in step c the temperature, T, is preferably about 5° C. to about 30° C., and more preferably about 15° C. to about 28° C. In another preferred embodiment the solids concentration is between about 0.3 to 0.35 wt % and the reaction of step c is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C. Typically, at least 80 wt % of the insoluble collagen is converted to soluble collagen with a number average molecular weight 300,000 daltons and above; while more preferably at least 90 wt % of the insoluble collagen is converted to soluble collagen and the number average molecular weight is above 1,000,000 daltons.

A further typical embodiment of the invention includes a method for producing an aqueous solution of solubilized collagen by the steps of (a) providing an aqueous ground slurry of insoluble collagen; (b) adjusting the water or solid content of the wet ground slurry whereby the insoluble collagen is at a concentration that promotes substantially maximum solubilized collagen concentration in a final product; (c) adjusting the pH of the slurry from step b to obtain activity for a proteolytic enzyme added in step d; (d) adding and mixing the proteolytic enzyme with the pH adjusted slurry; (e) reacting the slurry of step d and or the recycled insoluble collagen of step g at a temperature, T, and for a time, t, effective for forming a solution comprising solubilized collagen derived from the insoluble collagen particles; (f) adding additional water and insoluble collagen to the solution containing solubilized collagen in step e and mixing; (g) separating at least some of the solution of step f containing solubilized collagen from the insoluble collagen and returning the insoluble collagen to step e, whereby at least a portion of the proteolytic enzyme is recycled, and a separated solution containing solubilized collagen is withdrawn as product. Another typical embodiment does not employ the recycle step but uses the solubilized collagen directly without removal of enzyme. Typically step e may be repeated two, three, four or more times. Additional enzyme may be added to the recycled insoluble collagen from step e that substantially replaces enzyme removed with the withdrawal of product or when the rate of reaction on recycling decreases below a predetermined level. In one typical embodiment, the method is operated as a continuous process. The reaction may typically be stopped by adjusting the pH to that where the proteolytic enzyme is substantially inactive; and/or by reducing the temperature to that where the proteolytic enzyme is substantially inactive. In another typical embodiment in step b, the liquid or solids content of the wet ground slurry is preferably adjusted so that the solids are at a concentration of about 0.1 to about 1.0 wt % in step e the temperature, T, is preferably about 5° C. to about 30° C., and more preferably about 15° C. to about 28° C. In another preferred embodiment the solids concentration is between about 0.3 to 0.35 wt % and the reaction of step e is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C.

Typically, at least 80 wt % of the insoluble collagen is converted to soluble collagen and the number average molecular weight is above 300,000 daltons; while more preferably at least 90 wt % of the insoluble collagen is converted to soluble collagen.

Another embodiment of the invention is a method for producing an aqueous solution of solubilized collagen by the steps of providing an aqueous ground slurry of insoluble collagen; adjusting the water or solid content of the wet ground slurry whereby the insoluble collagen is at a concentration that promotes substantially maximum solubilized collagen concentration that is adapted to strengthen paper in a final product; adjusting the pH of the slurry from Step b to obtain activity for a proteolytic enzyme added in Step d; adding the proteolytic enzyme to the pH adjusted slurry and reacting at a temperature, T, and for a time, t, effective for forming solubilized collagen from the insoluble collagen particles; controlling the reaction conditions for obtaining a high concentration of soluble collagen by measuring the concentration of solubilized collagen and the molecular weight of the solubilized collagen, whereby the reaction is complete when the number average molecular weight fraction above 300,000 daltons and the concentration are substantially maximized; and withdrawing the aqueous solution of solubilized collagen as product.

Feed material for the process can typically come from a variety of sources as long as the feed is relatively clean and has collagen containing material of relatively small particle size, see for example the method of Komanowsky et al discussed below. One typical method for preparing the feed material of a wet ground slurry of insoluble collagen from animal tissues includes the steps: (a) providing soft animal tissues containing collagen; (b) cleaning the collagen containing tissues to remove hair, fat, carbohydrates, and other contaminants; (c) cutting the cleaned collagen containing tissues into small pieces; (d) mixing the small pieces with water to obtain a slurry; (e) adjusting the pH of the slurry substantially near the isoelectric point of collagen from the tissues; (f) wet grinding the resulting pH adjusted slurry to obtain a slurry of insoluble collagen. The pH of this method is typically about 3 to about 7. The invention further encompasses the unique aqueous solutions of solubilized collagen produced by the above methods.

A yet further embodiment of the invention includes a method for making a collagen strengthened cellulosic sheet by the steps of: (a) providing a cellulosic pulp slurry; (b) adding solubilized collagen to the pulp slurry, and mixing for a time effective for interaction of the cellulosic pulp slurry and solubilized collagen; (c) forming the interacted cellulosic pulp slurry and solubilized collagen into a sheet; and (d) drying the sheet. Typically the formed sheet may be a sheet such as paper. Another embodiment includes a method for using solubilized collagen for strengthening paper by mixing the solubilized collagen with a cellulosic pulp slurry, molding the mixture and drying.

A still further embodiment includes a strengthened cellulosic pulp composition of a dried reaction product of a mixture of solubilized collagen and cellulosic pulp. Another typical embodiment is a strengthened paper product of paper prepared from a mixture of solubilized collagen and cellulosic pulp.

Yet another typical embodiment includes a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and caustic, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) adding between about 0.1 dry wt % to about 2 dry wt % soluble collagen (based on dry weight of cellulosic material) to the diluted pulp slurry, and mixing at a shear rate and a time effective for interaction of the diluted pulp slurry solids and soluble collagen, whereby at least a substantial portion of the soluble collagen is bound to the paper pulp to form a collagen-pulp slurry; (d) diluting the collagen-pulp slurry to between about 0.1 dry wt % and 1 dry wt % consistency; (e) forming the collagen-pulp slurry into a sheet and drying the sheet. Typically the mixing in step c is for about 15 minutes. The pH may be adjusted with an acid selected from the group consisting of muriatic acid, HCl, $HNO_3$, $H_2SO_4$, and acetic acid. If desired the method may include the additional step of coating the sheet of step e with sizing prior to drying. Typically the sizing further may be a collagen hydrolyzate having a number average molecular weight of 100,000 daltons or less. The dried sheet may be calendered. Typically the caustic of step a can be a NaOH solution with a concentration of about 0.25 wt % to about 1.00 wt % based on dry weight of cellulosic pulp solids, and a pH range 10–14.

Typically the solubilized collagen has a number average molecular weight above 300,000 daltons, and most preferably above about 1,000,000 daltons. The mixing shear rate and other conditions are adapted to promote collagen-pulp interactions without denaturation of the collagen triple helical structure. In some applications the collagen-paper slurry preferably has a consistency of about 0.5 dry wt %. If desired an alum/rosin additive is added after pulping in step a or after dilution in step b or after refining. Also after forming the sheet in Step e, the formed sheet can be wet pressed to a preselected thickness prior to drying.

In one typical embodiment, when only water is selected in step a, the additional step of refining the pulp/water slurry from Step a is preferred to fibrillate cellulose fibers in order to obtain a selected degree of freeness upon forming a sheet in Step e. When substantially reclaimed newsprint is selected, the degree of freeness is preferably between about 100 CSF and about 150 CSF and when substantially reclaimed carton container is selected the degree of freeness is preferably between about 300 CSF and about 400 CSF.

A yet further embodiment includes the steps of a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) adding an alum/rosin additive to the pulp slurry after Step a or to the diluted pulp slurry after Step b; (d) forming the diluted pulp slurry containing alum rosin into a sheet; (e) coating one or both sides of the sheet with collagen hydrolyzate having a number average molecular weight of 100,000 daltons or less; and drying the sheet.

Another typical embodiment includes a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) providing an aqueous ground slurry of insoluble collagen; (d) adjusting the water or solid content of the wet ground slurry whereby the insoluble collagen is at a concentration that promotes substantially maximum solubilized collagen concentration and molecular weight in a final product; (e) adjusting the pH of the slurry from Step d to obtain activity for a proteolytic enzyme added in Step f; (f) adding the proteolytic enzyme to the pH adjusted slurry and reacting at a temperature, T, and for a time, t, effective for forming a solution of high molecular weight solubilized collagen from the insoluble collagen particles; (g) controlling the reaction to obtain a high degree of solubilization of collagen and a molecular weight of the solubilized collagen where the collagen is capable of binding with cellulosic pulp by simultaneously measuring the concentration of solubilized collagen and the molecular weight of the solubilized collagen, whereby the reaction is complete when the molecular weight and the concentration are substantially maximized; (h) adding and insoluble collagen with or without additional water to the solution containing high molecular weight solubilized collagen in Step f and mixing; (i) separating at least some of the solution containing high molecular weight solubilized collagen from the insoluble collagen and returning the insoluble collagen to Step d, whereby at least a portion of the proteolytic enzyme is recycled, and the separated solution containing high molecular weight soluble collagen is withdrawn; (j) adding the separated solution of Step i. comprising between about 0.1 dry wt % to about 2 dry wt % soluble collagen (based on dry weight of cellulosic material) to the diluted pulp slurry, and mixing at a shear rate and a time effective for interaction of the diluted pulp slurry solids and soluble collagen, whereby at least a substantial portion of the soluble collagen is bound to the paper pulp to form a collagen-pulp slurry; (k) diluting the collagen-pulp slurry to between about 0.1 dry wt % and 1 dry wt % consistency; (l) forming the collagen-pulp slurry into a sheet; and drying the sheet.

A still further embodiment includes a method for producing a collagen strengthened sheet by the steps of: (a) providing an aqueous ground slurry of insoluble collagen and adjusting the pH of the slurry to obtain activity for a proteolytic enzyme added in Step b; (b) adding the proteolytic enzyme to the pH adjusted slurry; (c) reacting the slurry and enzyme of Step b or Step e at a temperature, T, and for a time, t, effective for forming a solution increased in high molecular weight solubilized collagen; (d) adding insoluble collagen with or without additional water to the solution of Step c and mixing; (e) separating at least some of the solution of Step d containing high molecular weight solubilized collagen from the insoluble collagen, whereby at least a portion of the proteolytic enzyme is recycled to Step c, and the separated solution containing high molecular weight solubilized collagen is withdrawn as product; (f) mixing a cellulosic material selected from the group consisting of virgin paper pulp, broke, reclaimed newsprint, reclaimed carton container, or a mixture thereof with a solution comprising water, or water and caustic, and mechanically pulping until a pulp slurry is formed having a consistency of about 3 to about 6 wt % based on dry pulp solids; (g) diluting the pulp slurry to a consistency of about 1 to about 3 wt % based on dry pulp solids and adjusting pH to about 3.5 to about 7.0; (h) adding soluble collagen from Step e to the diluted pulp slurry in an amount from between about 0.1 to about 2 dry wt % soluble collagen (based on dry weight of cellulosic material), and mixing at a shear rate and a time effective for interaction of the diluted pulp slurry solids and soluble collagen, whereby at least a substantial portion of the soluble collagen is bound to the paper pulp to form a collagen-pulp slurry; (i) diluting the collagen-pulp slurry to between about 0.1 dry wt % and 1 dry wt % consistency; and (j) forming the collagen-pulp slurry into a sheet and drying.

Another typical embodiment includes a method for producing an aqueous solution of high molecular weight solubilized collagen by the steps of: (a) providing an aqueous ground slurry of insoluble collagen; (b) adjusting the water or solid content of the wet ground slurry whereby the insoluble collagen is at a concentration that promotes substantially maximum solubilized collagen concentration and molecular weight in a final product; (c) adjusting the pH of the slurry from Step b to obtain activity for a proteolytic enzyme added in Step d; (d) adding and mixing the proteolytic enzyme with the pH adjusted slurry; (e) reacting the slurry of Step d at a temperature, T, and for a time, t, effective for forming a solution comprising high molecular weight solubilized collagen derived from the insoluble collagen particles; (f) adding additional water and insoluble collagen to the solution containing high molecular weight solubilized collagen in Step e and mixing; (g) separating at least some of the solution of Step f containing high molecular weight solubilized collagen from the insoluble collagen and returning the insoluble collagen to Step e, whereby at least a portion of the proteolytic enzyme is recycled, and the separated solution containing high molecular weight solubilized collagen is withdrawn as product; (h) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 to about 6 wt % based on dry pulp solids; (i) diluting the pulp slurry to a consistency of about 1 to about 3 wt % based on dry pulp solids and adjusting pH to about 3.5 to about 7.0; (j) adding soluble collagen from Step e to the diluted pulp slurry in an amount from between about 0.1 to about 2 dry wt % soluble collagen (based on dry weight of cellulosic material), and mixing at a shear rate and a time effective for interaction of the diluted pulp slurry solids and soluble collagen, whereby at least a substantial portion of the soluble collagen is bound to the paper pulp to form a collagen-pulp slurry; (k) diluting the collagen-pulp slurry to between about 0.1 dry wt % and 1 dry wt % consistency; and (l) forming the collagen-pulp slurry into a sheet and drying.

A further embodiment of the invention includes a method for making a collagen strengthened cellulosic sheet by the steps of: (a) providing a cellulosic pulp slurry; (b) adding solubilized collagen to said pulp slurry whereby said cellulosic pulp and said solubilized collagen have a consistency above about 2 wt %, and mixing for a time effective for interaction of said cellulosic pulp slurry and solubilized collagen and whereby said mixing is at a temperature above about 35° C., or more preferably above 40° C; (d) forming said interacted cellulosic pulp slurry and solubilized collagen into a sheet; and (e) drying said sheet.

DETAILED DESCRIPTION OF THE INVENTION

Figure 1B:
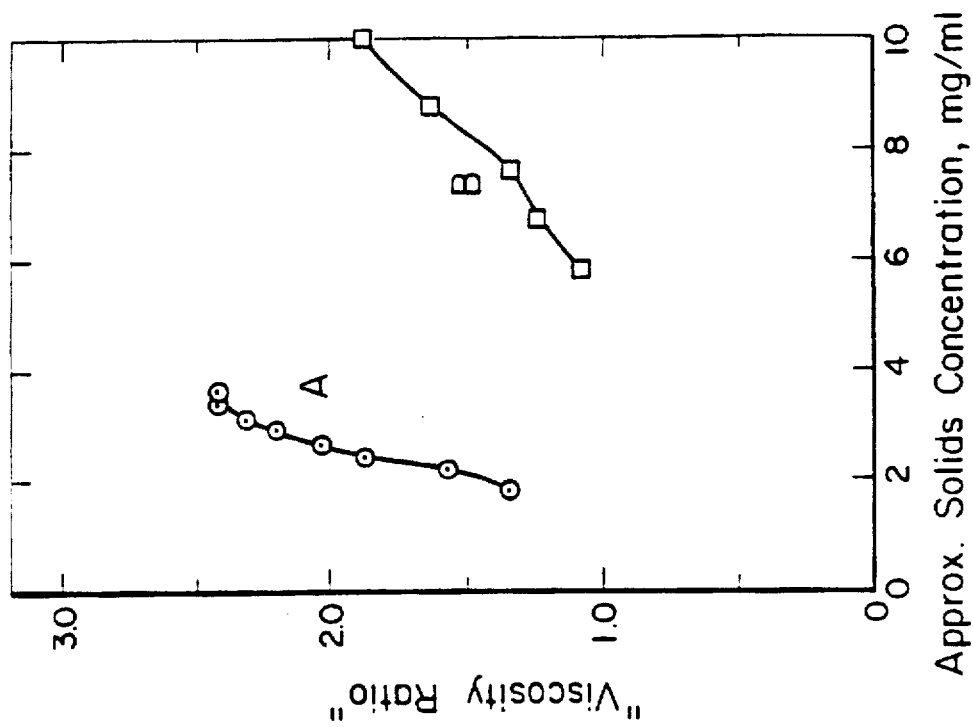
FIG. 1B is a plot showing the ratio of the viscosity determined at 20 rpm to the viscosity at 100 rpm, termed here the "viscosity ratio". The data is calculated from the data in FIG. 1A for both solubilized collagen of the invention (A) or the BA-1 collagen solutions (B). The viscosity ratio is plotted in the ordinate (vertical scale) and the approximate solids concentration, in mg/mL, is plotted in the abscissa (horizontal scale).

It was recognized that solubilized collagen material, added to a cellulose pulp prior to the papermaking process (i.e, mixed with the cellulose pulp fibers in the machine chest), resulted in a significant increase in strength of the paper-collagen composite. This result is surprising since the prior art teaches that larger insoluble aggregates of collagen, such as those produced by mechanical diminution of bovine hides, are necessary. One reason that the use of soluble collagen in papermaking may not have been considered is that soluble collagen can be expected to thermally denature at the fluids temperatures employed in papermaking (greater than about 40° C.). Denatured collagen is not expected to be as useful as native collagen aggregates. It is further surprising since one would expect that the cellulose pulp could best be bound together by larger size particles such as those of the scale of the cellulose pulp itself and not those that are soluble in water. As is demonstrated in the examples herein solubilized collagen that had been centrifuged at very high gravitational forces that would remove substantially all insoluble materials was very effective in increasing the strength of paper. Further, there is no current large-scale use or commercial source for a cost effective collagen solution of this type. Small-scale applications for soluble collagen exist in the food, cosmetic and pharmaceutical industries, for which the products are much higher priced than will be economically acceptable in the cellulose pulp and paper applications of the invention.

The basis for the subject invention is the observed strong interaction between soluble collagen and a variety of cellulosic pulp fibers, which leads for example to enhanced paper strength when collagen is added to the papermaking process. Other observations made during the investigation of soluble collagen-containing paper further suggest that other beneficial effects to the papermaking process may result from the addition of soluble collagen. Such benefits include, but are not limited to, increased first pass retention of pulp material, reduced BOD in the whitewater suggesting the potential to reduce soluble organic residue in paper mill effluents, and improved processability of short-fiber pulps, such as recycled fibers, leading to increased machine speed, improved pulp drainage, and decreased steam usage in the dryer section. These general observations, although not completely quantified at this time, suggest a much broader role for the use of soluble collagen in papermaking, especially when short-fiber pulps, such as secondary (recycled) fibers and/or virgin fibers from intrinsically short-fiber sources, are formed into paper, either alone or in blends with other pulp fiber.

Many non-cellulosic chemicals are used in the production of paper, including chemicals used in chemical pulping of wood, fillers, bleaching, deinking, and a variety of specialty chemicals and paper additives employed to improve product characteristics and/or to enhance performance of the papermaking process. A recent survey of chemicals used in the pulp and paper industry ("Industry Study 568: Pulp & Paper Chemicals, The Freedonia Group, Inc., Cleveland, Ohio, March, 1994) categorizes the specialty chemicals into the following categories: Dyes and Pigments; Wet Strength Resins; Biocides and Other Deposit Control Agents; Sizing Agents; Defoamers; Retention/Drainage Aids; Chelating Agents; and Thickening Agents. Based on the observed beneficial effects when soluble collagen is added to papermaking, we conclude that soluble collagen may find uses in many of these specialty chemical categories. The survey cited also frequently refers to the trend in papermaking to incorporate greater amounts of recycled fiber, and the resulting growing demand for specialty chemicals, which are required because of the problems resulting from the short fiber length and non-cellulosic contaminants generally found in these materials.

In particular, soluble collagenmay serve in the following applications in papermaking, as identified in the cited survey:

Chelating Agent.

Many chemical additives (aminocarboxylic acids, sodium tripolyphosphate, citrates) are used in papermaking to enhance bleaching operations by reducing bleach degradation, brightness reversion, and scale and pitch problems. These agents are employed to effectively remove common heavy metals, such as manganese, iron or copper ions, that interfere with the activity of added chemicals. Soluble collagen is a naturally occurring multivalent polyelectrolyte molecule that has the potential to bind/chelate divalent metal cations.

Retention/Drainage Aid.

Soluble collagen is believed to interact with cellulosic fibers to promote increased effective fiber particle size. This property has been observed to result in higher first-pass retention of recycled fiber, and it should enable the use of soluble collagen as an effective retention aid in papermaking. Similarly, use of soluble collagen in papermaking should promote improved drainage of water from the pulp during formation of the sheet, thereby, for example, improving pulp processability and increasing machine speed.

Internal Sizing Agent.

Incorporation of soluble collagen into the wet end of the papermaking process has been demonstrated to enhance burst and tensile strength of the resulting paper. Other beneficial effects may also include limiting the rate of water penetration, improving the paper feel, reducing lint on the paper surface, and/or improving print quality.

Thickening Agent.

Soluble collagen has been observed to increase fiber-to-fiber bonding and to improve paper strength. A related beneficial effect of soluble collagen addition may be to increase the viscosity of pulp slurries, thereby helping to maintain pulp stability during the papermaking process.

Wet Strength Resin.

Soluble collagen has been observed to increase fiber-to-fiber bonding and to improve dry paper strength. A related beneficial effect of soluble collagen addition may be to enhance retention of tensile strength after complete aqueous saturation of the paper.

Definitions

The following definitions will be useful in reading the disclosure herein:

Acidified collagen—collagen that has been treated with an acid or extracted by an acid solution.

Beating—mixing paper pulp at a relatively high shear rate in order to separate and expand the size of pulp fibers.

Broke—scrap paper from the papermaking process.

Calendering—process of creating surface smoothness and hardness in paper typically by on-line compression between (counter-rotating) cylinders.

Cellulosic pulp—fibers from cellulosic materials that could be wet or dry and produced by mechanical, chemical or other means.

Chelating agent—chemical additives used in papermaking to enhance bleaching operations by reducing bleach degradation, brightness reversion, and scale and pitch problems.

Collagen gel—collagen that exists in its native molecular state in a continuous, highly hydrated fibrillar network.

Collagen sizing—collagen added as a coating after paper sheet has been made.

Degree of freeness—a measure of how easily (freely) water will drain from a paper sheet during production, performed in a standardized test apparatus; one industry recognized standard is Canadian Standard Freeness (CSF).

Drainage aid—chemical additives used in papermaking to promote improved drainage of water from the pulp during formation of the sheet, thereby, for example, improving pulp processability and increasing machine speed.

Internal size—chemical additives incorporated in the wet end of the papermaking process to limit the rate of water penetration, enhance burst and tensile strength, improve the paper feel, reduce lint on the paper surface, and/or improve print quality.

Mechanically pulping—mechanical separation of cellulosic fibers by specially designed high-shear mixers.

Mechanically working—mechanical shearing of collagen-rich materials to reduce particle size and initiate gel formation.

Mixing collagen and cellulosic (e.g. paper pulp)—mixing is at a relatively lower shear rate (as compared to beating) that is conducive to the reaction of higher molecular weight collagen with cellulosic pulp so as to obtain interaction of solubilized collagen and cellulosic pulp.

Molecular weight—this term as used herein is intended to refer to number average molecular weight unless otherwise specified.

Natural or native collagen—collagen molecules that retain the normal triple-helical assembly of alpha-chains.

Old corrugated container—secondary cellulosic fiber from recycled corrugated container or similar Kraft pulping process sources.

Old newsprint—secondary fiber from recycled newspapers and similar sources.

Pulp slurry—cellulosic material, selected from the group consisting of virgin paper pulp, reclaimed newsprint, reclaimed carton container, or the like, or mixtures thereof, that have been mechanically pulped to form a suspension of pulp fibers.

Reclaimed paper—paper as received from recycling operations.

Recycled paper—reclaimed paper that has been reprocessed and made into new usable paper.

Refining—a pretreatment for the paper pulp that expands and separates cellulosic pulp fibers.

Retention aid—chemical additives used in papermaking to enhance retention of pulp fibers and other fillers and additives during the formation of paper. Increased use of recycled fibers has resulted in greater demands for retention aids because of the shorter fibers in recycled pulps.

Sizing agents—chemical additives used in papermaking to limit the rate of water penetration, enhance burst and tensile strength, improve the paper feel, reduce lint on the paper surface, and/or improve print quality. Sizing agents may be incorporated either by "internal" (added to the wet end of the papermaking process) or "surface" (applied to the paper after the sheet is formed) methods.

Solubilized collagen—collagen that has been treated to separate the collagen fibrils to render them soluble while retaining the normal triple-helical assembly of native collagen; covalent bonds between collagen fibrils are broken so that smaller collagen molecules can go into solution; this is in comparison to mechanically worked and or acid treated collagen that merely makes the collagen pieces physically smaller but does not break the covalent bonds between fibrils; the solubilized collagen used herein has been solubilized by an enzymatic treatment that breaks the covalent bonds between collagen fibrils.

Thickening agent—chemical additives used in papermaking to increase fiber-to-fiber bonding and improve strength by increasing the viscosity of liquid mixtures. These chemicals may also help to maintain pulp stability because of their emulsifying properties.

Viscosity ratio—the ratio of two viscosity measurements of a solution at two different shear rates. This is one typical way to follow the increase or decrease of viscosity due to an increase or decrease of solubilized collagen being produced from a slurry of insoluble collagen. Another typical method would be to use only the viscosity measurement to follow the increase or decrease of solubilized collagen.

Wet strength resin—chemical additives used in papermaking to enhance retention of tensile strength after complete aqueous saturation of the paper.

A. First General Embodiment

One typical embodiment of the first general embodiment achieves lower costs of operation by utilizing recycle steps to recapture and reuse enzyme that would normally be lost on removal of soluble collagen product solutions. Another typical embodiment of the first general embodiment also has low costs of operation but does not utilize the recycle steps to recapture enzyme. In this latter embodiment the solubilized collagen is sent directly to its end use, such as in papermaking, with no attempt to remove enzyme or otherwise purify the solubilized collagen.

Advantages of the first general embodiment of the invention are in: (1) minimizing the cost of preparing soluble collagen by processing directly from ground skin material to the maximum amount of soluble macromolecules; and (2) at the same time, maximizing the degree of conversion to soluble collagen material capable of binding to cellulosic pulp and controlling the molecular weight of the soluble collagen material in order to enhance the binding effect to the pulp fibers, thereby maximizing the resulting tensile strength and/or other mechanical properties of the paper product. Another major advantage of using solubilized collagen over the insoluble larger aggregates of the prior art, in the production of cellulosic products such as paper, is greater uniformity in the distribution of collagen in the cellulosic pulp.

Bovine skin was selected as the collagen source in the examples described here because collagen preparation methods from skin have been widely reported, and the material is a high volume by-product of the major industries of beef production and leather manufacture; however, it is expected that collagen obtained from other sources (e.g. tendon) will work in the process also.

Collagen solubilization of skin has been accomplished by an enzymatic hydrolysis process with an animal stomach enzyme (e.g. pepsin) and several other enzymes without any other purification steps. The process results in nearly complete solubilization of ground hide preparations in 10–30 hours at room temperature in acidic solutions. Other (untested) enzymes may yield faster or cheaper conversion of collagen-containing tissues, and the process has not necessarily been optimized to minimize enzyme requirements and production time. To date, the process has been scaled to produce approximately 500 gallons of 0.3–0.4% collagen solution, and it has been demonstrated to be relatively easy to control.

EXAMPLES

The following examples, illustrative of the novel compositions and the novel methods of preparing them, are given without any intention that the invention be limited thereto.

Materials

The pepsin used was a crude (relatively unpurified) powder from pig stomach mucosa (Cat. No. P7125) purchased from Sigma Chemical Company, St. Louis, Mo. Lot # 070H0437 of this product, used in the examples, contains approximately 15% protein (by UV), with an activity of 91 pepsin units/mg solids and 620 units/mg protein. Residual solids in the preparation appear to be a combination of precipitation salts, buffer salts and/or carbohydrates. Crystallized pepsin has a maximum specific activity of about 3500 units/mg protein.

Additional tests were performed with pepsin, crude powder, from Sigma Chemical Company; AFP 2000, acid fungal protease from a strain of *Aspergillus niger*, from Solvay Enzymes; Newlase A from a strain of *Aspergillus niger*, and Newlase II (from a strain of *Rhizopus niveus*, from Amano Enzyme U.S.A.; Quest AP, quest acid protease from a strain of *Aspergillus niger*, from Quest International; EDC-APA, an EDC acid protease A, and EDC-APB, an EDC acid protease B, from Enzyme Development Corporation.

The collagen slurry used herein for Examples 1A–6A was prepared from ground limed-splits of bovine skin. The collagen was supplied by Teepak's Sandy Run Plant, Columbia, S.C. Typical analyses for the material of Example 6A are pH=6.4; solids content=15.67%; gelatin content= 2.62%; fat content=2.1%. A 1974 USDA report by Komanowsky, M., et al, "Production of Comminuted Collagen for Novel Applications", *J. American Leather Chem. Assoc.*, 6, 410–422 (1974), describes techniques for pre-slicing, acidifying and wet-grinding of limed splits to produce five "comminuted" (ground) collagen products, classified by extent of grinding and the resulting particle size and texture. A subsequent 1978 paper by Turkot, et al, "Comminuted Collagen: Estimated Costs of Commercial Production", *Food Tech.*, 48–57 (April, 1978), presents an economic analysis of the production costs for these same five products. The output from this plant closely approximates the ground limed-split material used as a source for collagen in the examples herein.

For Examples 7A to 11A unless otherwise provided the enzymatic collagen solubilization was performed as follows. The collagen source (either ground whole hides or ground limed splits) ground as described in Example 7A with an 0.06 inch cutting head and in a water slurry was spun at 4° C. in a Beckman J2-21 Centrifuge (JA-20 rotor) at 10,000 rpm for 20 minutes to remove excess liquid. This centrifuge provided a ratio of rpm to gravitation force of about 1:1, thus at 10,000 rpm the G forces were about 10,000×gravity. The supernatant liquid was removed and the centrifuged solids (7.5 g) were added to a one liter Erlenmeyer flask that contained deionized water (750 mL). The suspension was stirred with a two inch magnetic stir bar and the pH was adjusted using concentrated hydrochloric acid. The enzyme was then added to the flask, which was placed in an incubator set to the desired temperature. Viscosity measurements were made by pouring approximately 100 mL of each reaction mixture into a beaker and bringing to room temperature. The viscosity was measured with a Brookfield Synchro-lectric Viscometer model RVT. Measurements were made at 20 rpm and 100 rpm with spindle No. 3. Three readings were taken at each speed and averaged for the calculation of viscosity in centipoise. Aliquots were removed for viscosity measurements at specified times and then returned to their original flasks.

A collagen solution ("BA-1"), used as a control solution in the examples, was supplied as the soluble skin product, Secolan BA-1, by Kensey Nash Biomaterials, Exton, Pa. The collagen solution is typically a white milky color; pH=3.1–3.3; total solids=1%±0.2%; active collagen>0.67% (nominally 1% in the examples). This product is sometimes found to be slightly gelled upon receipt. However, based on the pattern observed after electrophoretic analysis, it is believed that the BA-1 is produced by an acid-extraction process, not by an enzymatic reaction as practiced in the present invention.

It was found that the solubilization of collagen-containing solids can be effectively monitored by periodic measurement of the solution viscosity Fluid viscosities can be conveniently measured by a variety of relatively simple methods, such as the Brookfield Model #RVT Viscometer (#3 Spindle) used with the examples. In this Brookfield system, the force exerted by a fluid upon a disk, which is rotated at constant rotational speed in the fluid, is used to estimate the fluid viscosity. In the collagen solutions described herein, the fluid viscosity will be strongly dependent on the concentration of dissolved collagen, the molecular weight distribution of the soluble collagen and the fluid temperature, and, to a lesser extent, fluid pH and ionic strength.

When the viscosity is independent of the applied force (shear), then the fluid is said to be "Newtonian". For solutions of many macromolecules, including the rod-like collagen molecules considered here, the solution viscosity is very dependent on the force applied to the liquid, and the liquid is said to be "non-Newtonian". When the dissolved macromolecules are highly elongated, and the shear rate (proportional to the rotational speed) is sufficiently high, the molecules tend to orient with the streamlines of the fluid and their effect on the fluid velocity tends to decrease in a manner that is strongly dependent on the shear rate.

Figure 1A:
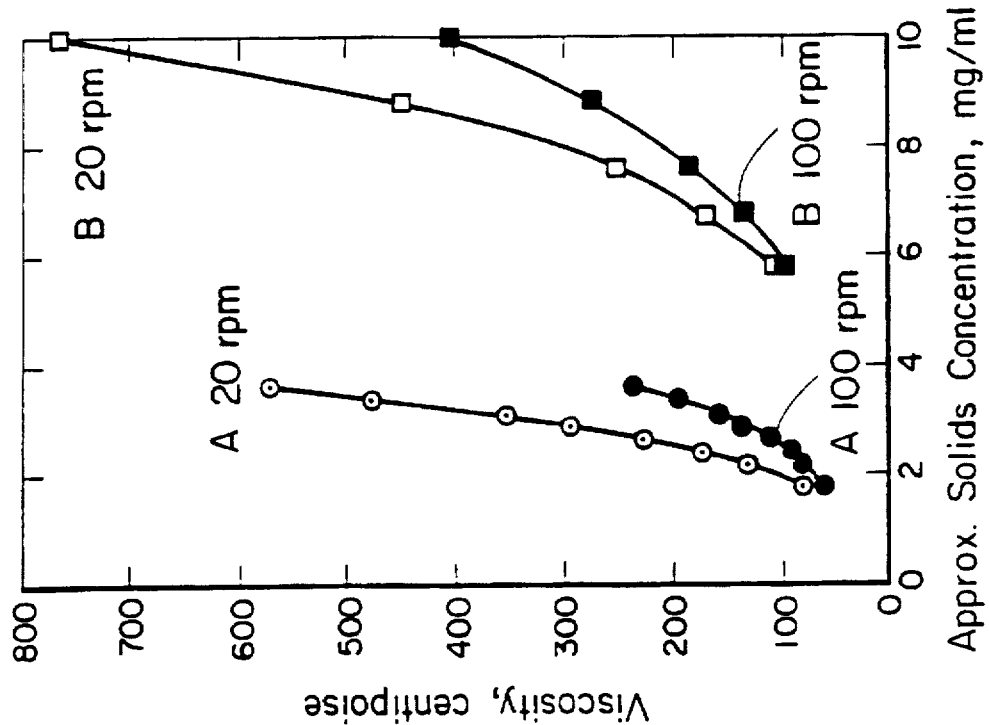
FIG. 1A is a plot showing the non-Newtonian behavior of the collagen solutions. Viscosity of diluted solutions of solubilized collagen of the invention (A) and BA-1 collagen solutions (B) at two shear rates (20 and 100 rpm). Viscosity, in centipoise, is plotted in the ordinate (vertical scale) and the approximate solids concentration, in mg/mL, is plotted in the abscissa (horizontal scale).

The non-Newtonian behavior of collagen solutions is demonstrated in the experiments summarized in FIG. 1A, in which the viscosity of preparations of solubilized collagen and BA-1 were determined at room temperature as the solutions were progressively diluted with distilled water. Some uncorrected increase in solution pH may have occurred in this experiment as the samples were diluted; however, the trend for the data is valid.

For each solution, the viscosity was determined at two rotational speeds, 20 and 100 rpm. The open circles (-○-) and filled circles (-●-) represent data for solubilized collagen of the invention at 20 rpm and at 100 rpm, respectively. The open squares (-□-) and the filled squares (-■-) represent the data for the BA-1 collagen control at 20 rpm and 100 rpm respectively. Both solutions were more viscous at the lower rotational rate, as expected. The viscosities of the collagen produced in the examples and BA-1 preparations were substantially different, with the produced collagen solution having a much higher viscosity at lower collagen concentrations and a steeper slope. These effects appear to be primarily due to the difference in the average molecular weights of the collagen molecules in the two solutions, with the collagen solution of the invention having the larger number average molecular size. The comparison shows that the method of the invention was successful in making a higher viscosity collagen material at a lower concentration thus showing the number average molecular weight was higher.

The ratio of the viscosity determined at 20 rpm to the viscosity at 100 rpm, termed here the "viscosity ratio", is a convenient measure of this non-Newtonian, molecular-weight-dependent effect. This is illustrated in FIG. 1B, in which the viscosity ratio is higher for collagen solutions of the invention than for BA-1. In FIG. 1B the open circles (-○-) represent data from the solubilized collagen of the invention and the open squares (-□-) represent data from the BA-1 collagen solution. The viscosity ratio used herein is a measure of the "degree of conversion" of solid collagen materials to soluble collagen molecules, and also a measure of molecular weight, where higher values of the viscosity ratio will correlate with the desired higher number average molecular weights of the dissolved collagen. In FIG. 1B it is important to note that since the material is being diluted, an increase in viscosity ratio is measuring the increase in concentration of soluble collagen since the molecular weight of the material remains the same. In tests of the examples below, changes in the viscosity and viscosity ratio will be measuring changes in concentration. If desired the peak soluble collagen content can be measured by chromatographic and electrophoretic techniques.

Alternatively, analysis of solubilized collagen composition was routinely performed by SDS polyacrylamide gel electrophoresis (PAGE) that used a 3% stacking gel; 6% running gel, following denaturation by boiling with β-mercaptoethanol. Some irreversible precipitation occurs during the denaturation process. Gels were stained by Coomassie Blue dye and destained in staining buffer only.

PAGE results from this technique demonstrate (results not shown here) that BA-1 solutions contain predominately tropocollagen monomer (300,000 daltons) aggregates. Collagen solutions produced by the present process that had acceptable paper binding properties appeared to have a number average molecular weight of at least 300,000 daltons, with some components having the intact triple helix of alpha, beta and gamma chains as evidenced by PAGE, other preparations may have had a disrupted helix.

Analysis of solubilized collagen composition was also routinely performed by SDS polyacrylamide gel electrophoresis (PAGE) with the Pharmacia PhastGel System. PhastGel Gradient 4–15% polyacrylamide gels were used. The buffer system in the gel is 0.112M Tris acetate, pH 6.4. PhastGel SDS Buffer Strips that contain, at pH 8.1, 0.2M Tricine, 0.2M Tris, and 0.55% SDS were used to run the gels. The separation method was from the PhastSystem Separation Technique File No. 130, Table 2.

Samples were prepared for Gel Electrophoresis by the addition concentrated stock solutions of SDS (20%) and buffers (5×stock). The final concentrations were 10 mM Tris/HCl (pH 8.0), 1 mM EDTA, 2–2.5% SDS, and 0.01% bromophenol blue. Each sample was then heated at 100° C. for 5 minutes and approximately 1 μL was applied to the gel. In some early experiments, 2-mercaptoethanol (a reducing agent) was added to the sample before heating. The addition of the 2-mercaptoethanol had no effect on the gel pattern.

At the completion of the electrophoresis, the gel(s) were stained with the Pharmacia Silver Kit. The staining method used was from the PhastSystem Silver Kit Instruction Manual, Table 2. The Development time and Background Reduction time were doubled for better visibility on the gels.

The SDS detergent in the gels disperses all non-covalent collagen aggregates leaving only covalently joined molecules. The degree to which these molecules migrate on a gel is related to their molecular weights and approximate molecular weights have been assigned to the collagen bands by co-electrophoresis of molecular weight standards on the same gels. PAGE analysis of solubilized collagen indicates bands at ~100,000 daltons (alpha-collagen), ~200,000 daltons (beta-collagen), ~300,000 daltons (gama-collagen), and bands >300,000 daltons. The intensity of the bands is in inverse order of their molecular weights.

Analysis for soluble or insoluble collagen was typically performed by first measuring the amount of hydroxyproline in the sample, then correlating this concentration with the collagen. Hydroxyproline was measured on 0.1 mL samples that were dried in polypropylene tubes at 125° C. The samples were dissolved in 0.05 mL 4M sodium hydroxide, capped, and then autoclaved for 30 minutes. Citric acid (0.05 mL of a 1.4M solution) and chloramine T reagent (1 mL of a solution that contained 1.41 g chloramine T, 10 mL 1-propanol, 10 mL deionized water, and 30 mL of a pH 6 citric acid/acetic acid buffer) were added to each tube which was then incubated for 20 min. at room temperature. PDAB solution (1 mL of a solution that contained 15 g p-dimethylaminobenzaldehyde, 62 mL isopropyl alcohol, and 26 mL 60% perchloric acid) was then added. The samples were incubated at 65° C. for 20 minutes, after which time 0.2 mL of each sample was transferred to a micro-titer plate reader and the absorbance read at 570 um. A sample of purified collagen (Vitrogen 100™; Celtrix) that contained 3.0 mg/mL collagen was found to contain 0.33 mg/mL hydroxyproline. Using this collagen preparation as a standard, multiplication of the hydroxyproline concentration by a factor of 9.1 will yield the collagen concentration.

High pressure liquid chromatography (HPLC) was performed to analyze the intact soluble collagen molecular weight distribution. HPLC was performed with a TOSOHAAS TSK-GEK G6000PW column (30 cm×7.8 mm) on a Waters 650 Advanced Protein Purification System. Absorbance was monitored at 220 nm with a flow rate of 0.25 mL/Min. (unless noted otherwise). The mobile phase contained 10 mM hydrochloric acid. A column prefilter was used with a 10 um frit.

Eluent fractions containing the HPLC peaks were analyzed by PAGE electrophoresis to determine the size of the constituent collagen molecules. The SDS in the gels disrupts the collagen aggregates so that only the molecular weights of covalently attached molecules can be determined by this method. The first eluting peak (Peak 1) contains molecules with number average molecular weights greater than 300,000 daltons as well as molecules with number average molecular weights of approximately 200,000 daltons and approximately 100,000 daltons. The smaller molecules appear to be constituents of larger aggregates that were disrupted by the SDS. The second eluting peak (Peak 2) contained molecules with number average molecular weights of approximately 300,000 daltons, approximately 200,000 daltons and approximately 100,000 daltons. The 200,000 dalton and 100,000 dalton molecules appear to be part of 300,000 aggregates that were disrupted by the SDS detergent. The third eluting HPLC peak (Peak 3) contains collagen fragments with number average molecular weights less than approximately 100,000.

In the examples below, it was determined that ground limed splits of beef hide can be nearly completely solubilized when they are subjected to pepsin hydrolysis at pH in the range of 2.0–2.2. Batch reaction times are typically 10–30 hours at room temperature (22°–26° C.). The maximum concentration of soluble collagen typically produced in this process is approximately 0.30–0.40% (3–4 mg dissolved collagen/ml). The process has been demonstrated at up to 2.0 liter-scale and, using essentially the same recipe, at approximately 500-gal scale, as discussed below. Microbial proteases gave similar results as discussed below.

Example 1A

Approximately 15 g of wet Teepak collagen solids were suspended by magnetic stirrer in 750 ml of Columbus, Ohio tap water at room temperature. The solution pH was adjusted to 2.1 with concentrated hydrochloric acid (HCl)— approximately 65–70 drops. Crude pepsin powder (0.38 g) was then added with stirring into the collagen suspension to initiate the reaction. The suspension was stirred overnight, during which heating of the solution to 26°–27° C. or higher sometimes occurred due to conduction from the stirrer plate. The viscosity of the solution was measured (20 & 100 rpm) periodically during the second day of the reaction until a maximum in the viscosity ratio was achieved, at which time the solution was stabilized by increasing the pH to 3.0–3.5 and/or by placing the solution in the refrigerator. Increasing the pH above 4.0 may initiate irreversible gelation of the collagen solution.

Figure 2:
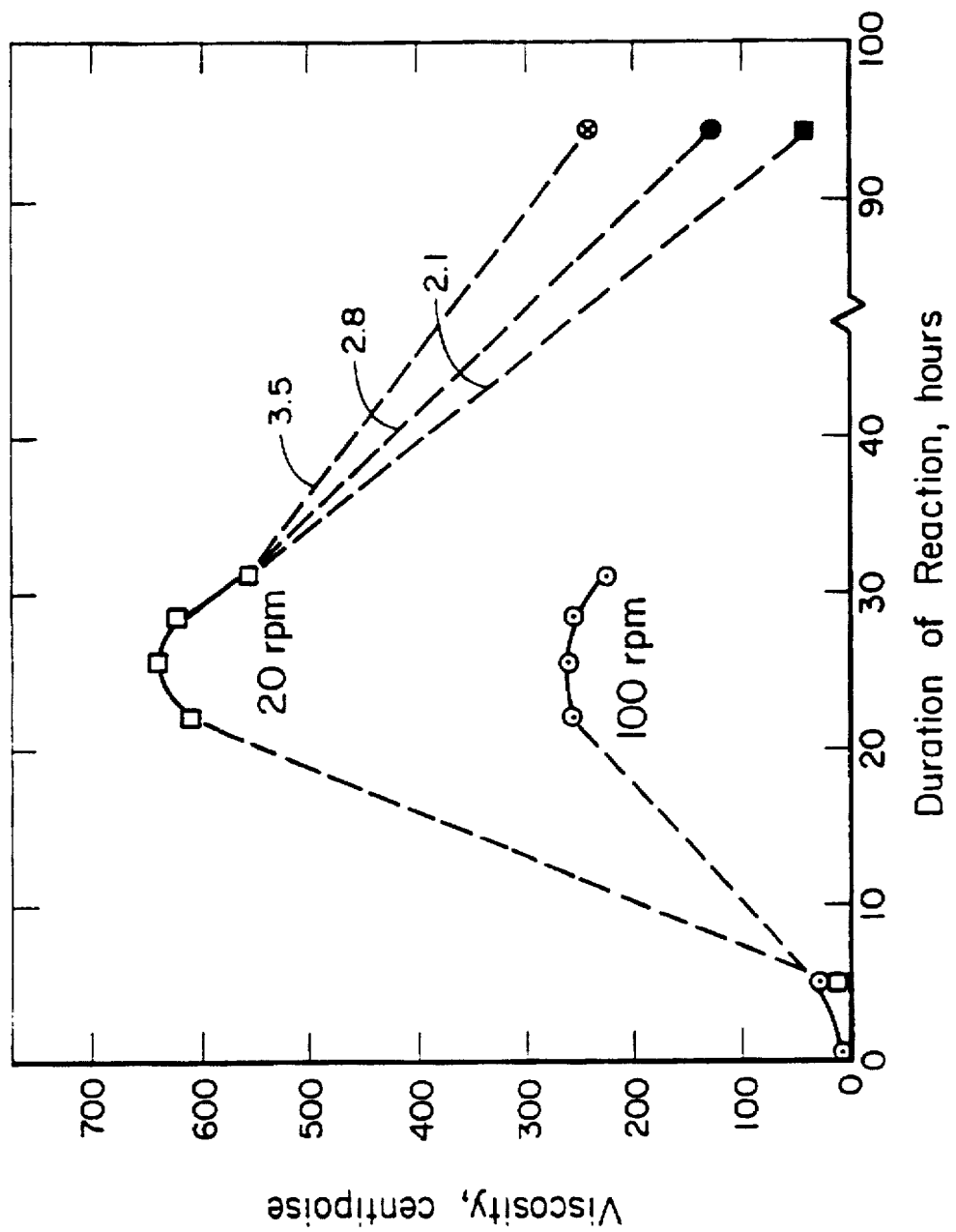
FIG. 2 is a plot of the data for Example 1A showing the viscosity at 20 rpm and 100 rpm. Viscosity, in centipoise, is plotted in the ordinate (vertical scale) and the duration of the reaction, in hours, is plotted in the abscissa (horizontal scale).

Results for Example 1A are plotted in FIG. 2. FIG. 2 shows a plot of viscosity, (in centipoise) as a function of time reaction (in hours). Viscosity measurements were taken at 20 rpm (squares) and 100 rpm (circles). After completion of the reaction at pH 2.1, three samples were taken and the pH adjusted to 2.1 (-■-), 2.8 (-●-), and 3.5 (-⊛-). Viscosity tests at 20 rpm taken several days later confirmed that the samples at pH=3.5 were indeed more stable and retained more of the original viscosity than those at pH=2.1.

Example 2A

Hydrolysis of Teepak collagen at temperatures between 30°–35° C. was investigated in a series of approximately 10 experiments to determine the potential for minimizing pepsin usage in the solubilization process. Typically, enzyme-catalyzed reaction rates will double with every 5°–10° C. increase in temperature. In these experiments, a 4-liter stainless steel beaker was wrapped with heating tape, then insulated with asbestos tape. The solution temperature was controlled by a Variac in line with the heating tape to about ±1°–2° C. The process above was scaled to 2 liters of reaction volume, and a range of lower pepsin concentrations and heating profiles was investigated. In nearly all cases, complete solubilization of the Teepak solids was accomplished in 10–15 hours, and in no case was substantial viscosity developed in the solubilized product.

Typical of the ten experiments is the following: 2 liters of water were added to a beaker, to which was added 40 g of Teepak collagen, then the pH was adjusted to 2.13 with concentrated HCl, and finally 1.0 g crude pepsin was added. Initially the bath temperature was 30.0° C., about 2.5 hours later the temperature was 33° C. and the viscosity at 100 rpm was 19 cps, and about 5.5 hours later the temperature was 36.5° C. with a viscosity of 8 cps. The sample was completely solubilized in less than 8 hours at 33°–36° C. with no increase in viscosity indicating the production of a higher molecular weight material. These experiments demonstrate that it is expected to be more difficult to conserve pepsin in this process by operating at higher reaction temperatures, even early during the hydrolysis process. The maximum feasible temperature for accumulating this particular large molecular weight collagen appears to be about 30° C.

Example 3A

Figure 3:
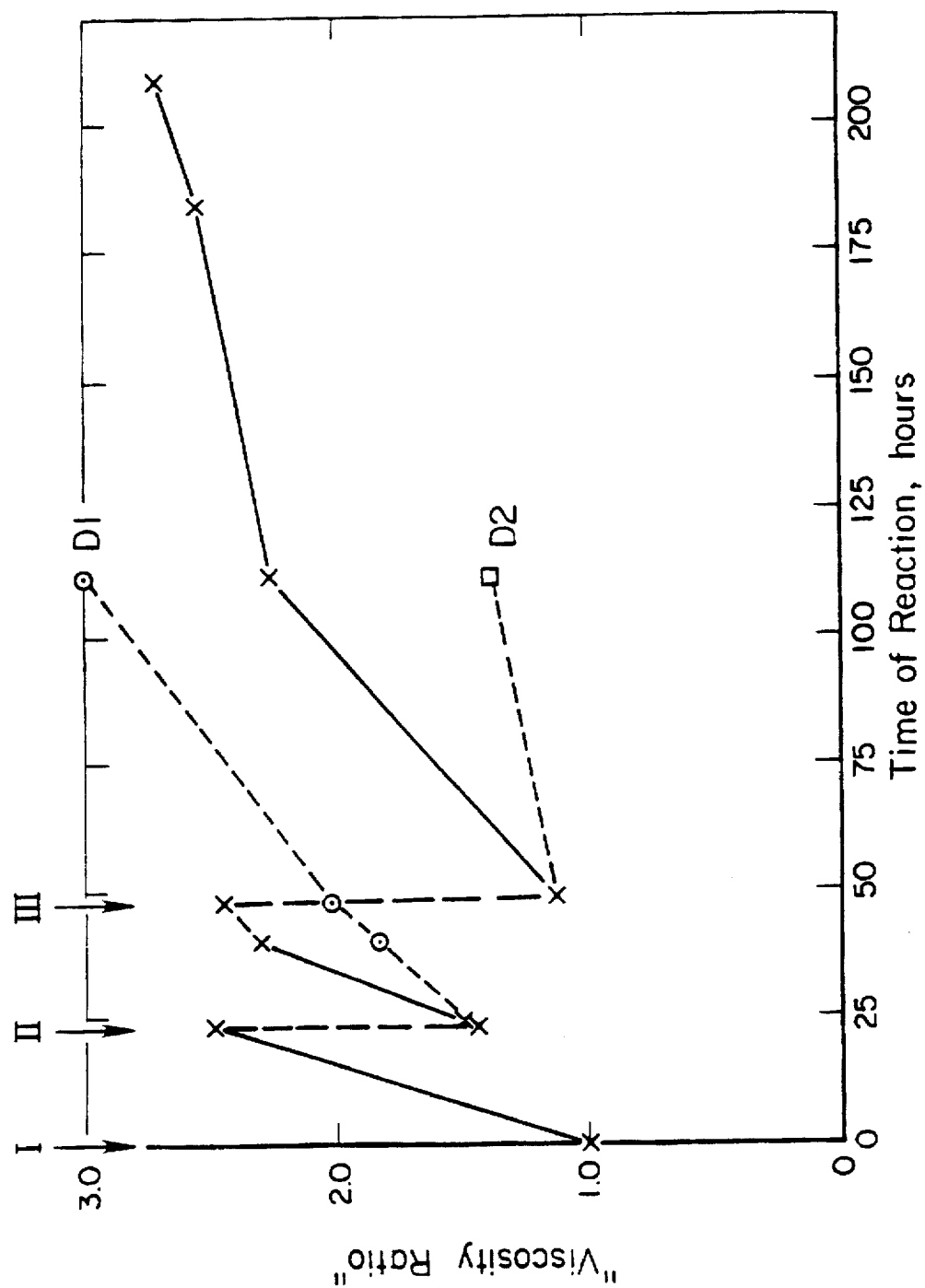
FIG. 3 is a plot of a small-scale batch collagen solubilizing reaction demonstrating the pepsin recycle of Example 3A. The viscosity ratio is plotted in the ordinate (vertical scale) and the time of reaction, in hours, is plotted in the abscissa (horizontal scale).

Another approach for minimizing pepsin usage in the process is illustrated by the experiment summarized in FIG. 3. In this experiment, the recipe above (750 ml Columbus, Ohio tap water, 15.5 g teepak collagen, 0.38 g pepsin, pH=2.1) was mixed on Day 0 to initiate the reaction in a 2-liter flask at room temperature (Roman numeral I). After approximately 1 day, an additional 750 ml of water and another charge of Teepak collagen solids (16.1 g) were added, but no additional pepsin was added to the reactor (Roman numeral II). The flask was stirred for about 5 minutes to mix the contents and the pH was readjusted with 30 drops of concentrated HCl, then the stirrer was turned off and the solids were permitted to settle out. After approximately 30 minutes, 750 ml of supernatant, "Day 1" supernatant (D1), was decanted into another flask, and stirring of both flasks was resumed. The Day 1 Supernatant contained some fine collagen particles, but it contained a much lower suspended solids load than the bottom fraction. The same process of dilution (755 ml water), collagen solids addition (15.2 g Teepak collagen), pH adjustment with 30 drops concentrated HCl (Roman numeral III), and supernatant decanting of "Day 2"supernatant (D2) was repeated in the first flask after approximately 2 days of reaction.

The progression of the hydrolysis reaction is illustrated by the solid lines (-x-) in FIG. 3. The circles (-o-) show a plot of the progression hydrolysis reaction of the Day 1 supernatant while the squares (-□-) show a plot of the Day 2 supernatant. In this example three typical charges of Teepak collagen were hydrolyzed by a single charge of pepsin, although the rate of hydrolysis appears to be decreasing with each cycle. Because the viscosity ratios of both the Day 1 and Day 2 supernatants appeared to increase after they were decanted from the main reactor, it was apparent that some pepsin and insoluble collagen was transported along with the supernatant. However, it appears that the pepsin has a higher affinity for solid collagen particles than for soluble collagen, thus most of the enzyme can be recycled several times before it is removed from the system, thereby minimizing the cost of this reagent. Preferably better separation of liquid and solids is obtained if the supernatant is separated from the insoluble collagen by centrifugation.

Most preferably a steady state in the processing recycle steps is desired. This is achieved by adding additional enzyme after the product removal step, when the rate of reaction in the recycle steps decreases below a predetermined level. Most preferably, additional enzyme is added that just replaces that lost with the removal of product.

Example 4A

An experiment was conducted in which 750 ml whitewater (recycle water from a papermaking process) was substituted for the tap water in the standard recipe of Example 3A above. Then 15.5 g Teepak collagen were added, the pH was adjusted to 2.14 with 40 drops of concentrated HCl, and 0.375 g of pepsin were added. Because the room temperature was elevated during this experiment, the reaction was conducted at 29°–31° C., and the solubilization appeared to proceed more quickly than standard reactions at 25°–26° C. In this single reaction, good viscosity was developed, the solids were nearly completely solubilized, and there appeared to be no problem with conducting the process in this solution (see Table 1A). Recycling whitewater from a papermaking process in this way will greatly diminish the amount of water introduced to the process.

TABLE 1A

Solubilized Collagen Made in Whitewater From Paper Making

| Time (Hours) | Viscosity 20 rpm | Viscosity 100 rpm | Viscosity Ratio |
|---|---|---|---|
| 0 | — | — | — |
| 18.5 | 415 | 177 | 2.34 |
| 22 | 440 | 186 | 2.37 |
| 26.7 | 365 | 166 | 2.20 |
| 42 | 280 | 136 | 2.06 |

Example 5A

In this example, 500 gal of Savannah, Ga. tap water was delivered to a double-paddle, 600 gal. stainless steel tank, and 75# of Teepak collagen (13.5# solids @ 18% solids) was dispersed in the water. Approximately 1.4 liters of concentrated HCl was added to bring the pH to 2.14. Pepsin (1.01 kg; Sigma Lot #70H0437) was slowly added, then the tank was covered with polyethylene film and the tank was stirred overnight. After approximately 20 hours, hydrolysis was incomplete (viscosity ratio=1.32). Because the liquid and room temperatures were relatively low (approximately 20° C.), it was decided to attempt to raise the liquid temperature by putting live steam onto the outside bottom of the tank. The steam was used for about 2.5 hours, by which time the liquid temperature was 23° C., the viscosity ratio was 2.15, and the steam heating was discontinued.

At approximately 31 hours, the viscosity ratio was 2.43, which is relatively high for this reaction. It was decided to adjust the pH in the tank to approximately 3.0, by the addition of approximately 450 grams of NaOH flakes, in order to stabilize the solution (slow/stop the pepsin reaction) for use in paper the next day. Approximately 55 gal of the pH=2.1 solution were saved in 5-gal containers prior to the pH adjustment. Because the viscosity ratio dropped slightly overnight for the pH=2.1 solution (open circles, -o-, in FIG. 4 and denoted by A) compared to the pH=3.0 solution (closed circles, -●-), it is concluded that pH adjustment is helpful in maintaining the highest possible molecular weight in the product during storage at room temperature.

After approximately 24 hours of reaction, some floating solid material (presumed to be fat because of its low density) was observed on the upper surface of the collagen solution near the mixer shaft. Although no attempt was made in this experiment to remove this residue, it can be easily skimmed from the preparation if the residual fat was found to be detrimental to collagen performance.

Prior to using the collagen solution made in this example and in Example 6A, described below, the solution was filtered by passing it through a knitted plastic screen with openings approximately 1×3 mm, in order to remove a small number of very slowly degrading skin particles. These particles are characteristically the last material to be dissolved by pepsin and can often be found in the 3–5 mm size range. A large sample of these residual particles was filtered from the collagen solution and their dry weight was measured. Based on projecting this sample to the entire batch of collagen solution, it was estimated that more than 95% of the initial solids were solubilized in this process.

Example 6A

Figure 4:
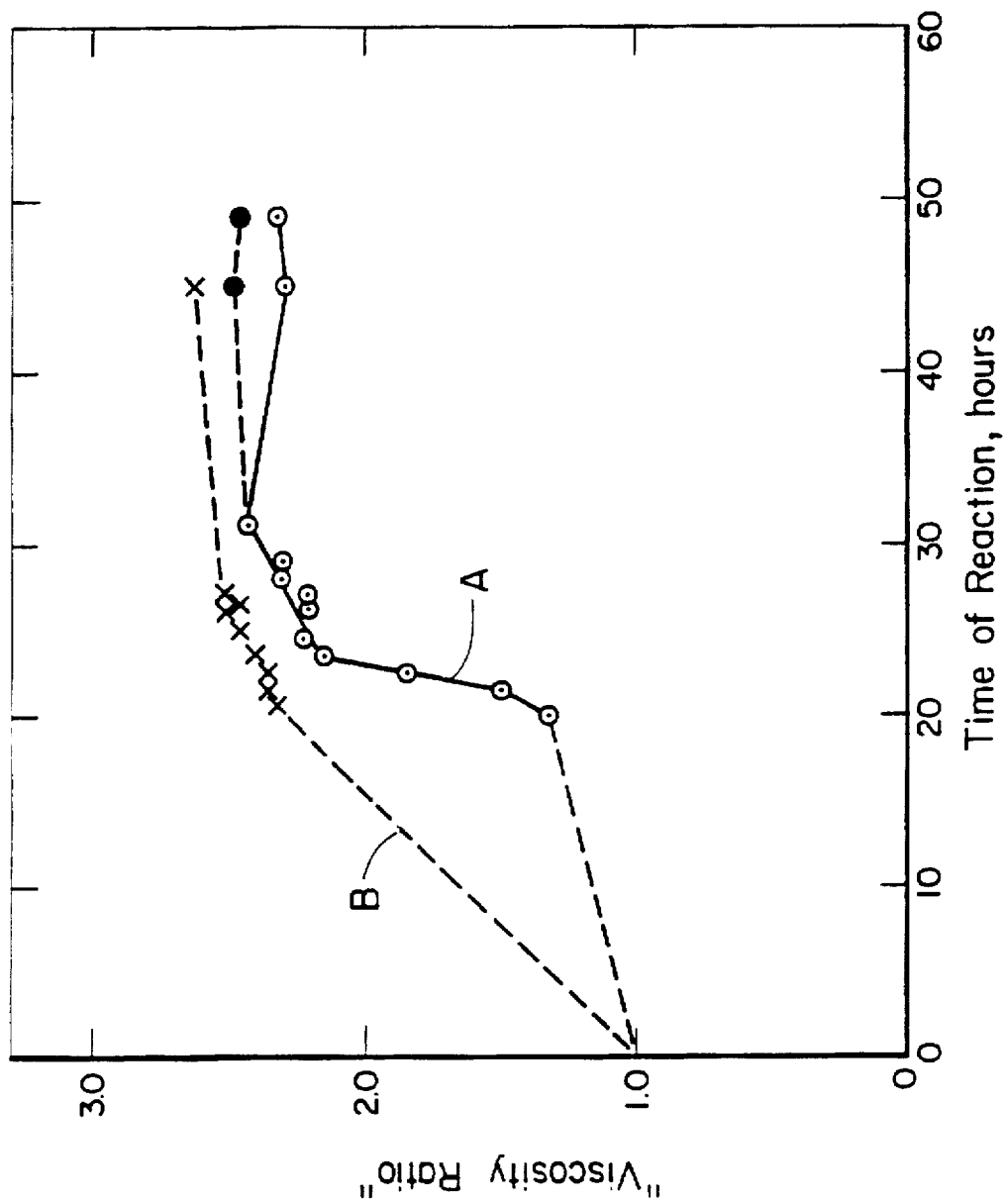
FIG. 4 is a plot of the development of viscosity ratios in Examples 5A (denoted by A) and 6A (denoted by B). The viscosity ratio is plotted in the ordinate (vertical scale) and the time of reaction, in hours, is plotted in the abscissa (horizontal scale).

In this example, the same tank was filled with 500 gal of Savannah, Ga. tap water, which in January was very cold—about 11° C. Teepak collagen (79.5#; 12.5# of solids at 15.67% dry wt.) was dispersed in this water, then 1.5 liters of concentrated HCl was added to bring the pH to 2.18. Pepsin (1.01 kg; Sigma Lot #70H0437) was slowly added, then the tank was covered with polyethylene film. Live steam was placed on the outer bottom of the tank for approximately 4 hours to raise the liquid temperature from 11.5° to 25° C. At this time the pH was 2.40; an additional 0.4 liters of concentrated HCl was added to bring the pH down to 2.29. The tank was draped with polyethylene film to insulate the tank overnight. After approximately 28 hours the viscosity ratio was 2.51, with the temperature at about 22° C. at pH=2.46. Approximately 600 g of flaked NaOH was added to bring the tank contents to pH=2.98, the tank was covered as before and stirred overnight. The final viscosity ratio was 2.61. Results are shown in FIG. 4 at B (-x-).

Since the collagen solution in Example 6A was produced at about a 2°–3° C. higher reaction temperature during the first day than that in Example 5A, the reaction appears to have progressed more rapidly, reaching completion about 4–5 hours sooner. When the pH was adjusted to about 3.0 the final solution appears to have slowed the enzymatic reaction so that little degradation of the soluble product was observed overnight.

The process is intended to produce nearly complete conversion of beef hides to a collagen solution using an enzymatic hydrolysis reaction. Objectives for the process are production of soluble collagen product at the maximum yield, while conversion costs and fixed capital expenditures are minimized. The process is not intended to produce food or medical-grade soluble collagen, and therefore requirements for production of clean solutions are minimal, and no purification of the soluble collagen is anticipated. No attempt has been made to remove the remnants of the other skin components (fat, proteoglycans, other proteins, salts, etc.), which are present in the ground-split feedstock at concentrations lower than collagen.

The process will require a series of cutters and grinders to reduce the feedstock limed splits to a shredded material that can be readily converted to soluble collagen. As cited above, the "front end" of the process will likely look similar to the USDA process for producing comminuted collagen. Depending on the pretreatment of the hides employed to prevent microbial growth, the hides may need to be delimed or acidified to remove residual calcium salts or other biocides. The ground solids are then mixed with process water (perhaps a reduced-solids whitewater stream from a paper plant), the pH is titrated to 2.0–2.2, and enzyme is added to begin the solubilization process. Following conversion, the soluble solids can be pumped directly to a paper making process and mixed with refined pulp solids or stabilized and stored.

In small-scale tests, maximum interaction between collagen and pulp solids appears to result if the pH of the solution is about 4.0 or less and the pulp consistency is 1.0% or lower. Therefore, adjustment of the pulp in the holding tank to about pH 4.0 or less appears to be beneficial although a typical run was at pH 5–6 because the paper was more stable.

Example 7A

"USDA" feed collagen materials were prepared using the method of Komanowsky et al., cited herein, as follows. Two limed splits and one dehaired and limed hide were rolled up and cut to yield 12 inch wide strips. These strips were passed through a strip cutter and then through a rotary knife cutter. An acidic solution was prepared by dissolving 102.15 g of benzoic acid in 1021.5 g of propionic acid. Acidification was carried out in 55 gallon stainless steel tumbling drums by adding 203 lbs of water and 521 g of the above acid solution to the material from the limed hide splits and 235 lb of water and 603 g of acid solution to the whole hide material. The drums were tumbled 15 minutes per hour for four hours. The final pH values were 5.1 and 5.2, respectively. Finally, part of both materials was passed through a 0.06 inch cutting head of the Urschel Comitrol. The remaining part was passed through an 0.200 inch cutting head. The products were poured into small plastic bags and placed into a freezer at −20° C. for later use.

Example 8A

USDA ground limed splits were centrifuged at 4° C. for 20 minutes at 10,000 rpm. The supernatant liquid was removed and the centrifuged limed splits (15 g) were added to a 2 L Erlenmeyer flask that contained deionized water (1500 mL). The suspension was stirred with a magnetic stirrer (2 inch stir bar) and the pH was adjusted to pH 2.1 with concentrated hydrochloric acid. Pepsin (0.76 g) was added to the flask, which was then stirred in an incubator set to 18° C. Aliquots of the reactions (100 mL) were removed at different times and analyzed for viscosity (Table 2A). The pH of each aliquot was adjusted to between pH 3 and pH 3.5 and the samples were stored at 4° C. After the last aliquot was taken (50 hours), analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline as shown in Table 2A.

Larger samples of the different fractions (50 mL) were combined with pH 3.5 acetic acid (100 mL) and centrifuged at 20,000 rpm for 4 hours at 4° C. The samples were stored at 4° C. for 9–10 days when they were used to make paper.

TABLE 2A

Summary of Results for Example 8A

| Sample Time (hrs) | Viscosity (20 rpm) (cps) | Hydroxy-Proline in Supernatant (mg/mL) | Hydroxy-Proline in Pellet (mg/mL) | ΔTS (% change from Control with no Addition) |
|---|---|---|---|---|
| 3 | 35 | 0.10 | 0.28 | 15 |
| 7 | 400 | 0.15 | 0.18 | 17 |
| 11 | 1055 | 0.23 | 0.12 | 21 |
| 15 | 1030 | 0.28 | 0.06 | 31 |
| 26 | 800 | 0.29 | 0.05 | 35 |
| 30 | 745 | 0.26 | 0.05 | — |
| 50 | 605 | 0.27 | 0.04 | 27 |

This data demonstrates that collagen was increasingly solubilized in this reaction up to approximately 15 hours. This was evidenced by the increase in hydroxyproline in the supernatant, the decrease in the pellet size and hydroxyproline content on centrifugation, and by the initial increase in viscosity. The increase in soluble collagen was correlated with an increase in the tensile strength of the paper to which the collagen was added, where ΔTS represents the % increase in tensile strength above the control paper with no added collagen.

Example 9A

Teepak limed splits were centrifuged at 4° C. for 20 minutes at 10,000 rpm. The supernatant liquid was removed and the centrifuged limed splits (35 g) were added to a 4 L Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 20.5° C. Aliquots of the reactions (200 mL) were removed at different times and analyzed for viscosity (Table 2A). The pH of each aliquot was adjusted to between pH 3 and pH 3.5 and the samples were stored at 4° C. until they were used to make paper.

After 27 hours at 20.5° C., one third of the incubated collagen sample was removed and stirred at room temperature. The temperature of the incubator was then adjusted to 30° C. and the remainder of the sample was stirred at this temperature. At specified times, 200 ml samples were removed, the pH adjusted, and the samples store at 4° C. as described above. After the last aliquot was taken, analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline content. The supernatants were also analyzed by size exclusion HPLC as shown in Table 3A.

Example 10A

Two preparations of solubilized collagen were combined as follows. Each preparation was made from Teepak limed splits that were centrifuged at 4° C. for 20 minutes at 10,000 rpm. The supernatant liquid was removed and the centrifuged limed splits (35 g) were added to a four liter Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 19° C. One preparation was incubated for 31.5 hours (final viscosity at 20 rpm was 1160 cps) and the other preparation was incubated for 21 hours (final viscosity at 20 rpm was 1025 cps). The two preparations were stored at 4° C., with no pH adjustment, for 6 days, then one and a half liters of each preparation were combined in a 4 liter flask, stirred to mix, and then rapidly heated to about 30° C. in a water bath. The flask was then stirred in a 32° C. incubator and, at specified

TABLE 3A

Summary of Results for Example 9A

| Incubation Time (hrs) | Peak Area | | | Viscosity (cps at 20 rpm) | Hydroxyproline in Supernatant (mg/mL) | ΔTS* (%) | |
|---|---|---|---|---|---|---|---|
| | Peak 1 −31 min. | Peak 2 −34 min. | Peak 3 ~45 min. | | | ONP | OCC |
| 5.5 | 9.0 | 14.9 | 5.7 | 25 | 0.09 | 14 | 27 |
| 21 | 17.5 | 21.0 | 9.5 | 375 | 0.17 | 27 | 42 |
| 23 | 16.4 | 24.7 | 10.1 | 425 | 0.17 | — | —f |
| 27 | 9.9 | 24.7 | 9.8 | 650 | 0.21 | 28 | 46 |
| 30a | 12.6 | 20.9 | 8.7 | 840 | 0.23 | 32 | 42 |
| 45.5b | 15.9 | 23.4 | 0.7 | 1095 | 0.28 | 37 | — |
| 30c | 18.5 | 30.2 | 40.2 | 750 | 0.20 | 26 | 43 |
| 45.5d | 18.4 | 24.5 | 54.4 | 45 | 0.30 | 36 | 46 | aThis sample was incubated for 27 hours at 20.5° C. and for 3 hours at rt.
bThis sample was incubated for 27 hours at 20.5° C. and for 18.5 hours at rt.
cThis sample was incubated for 27 hours at 20.5° C. and for 3 hours at 30° C.
dThis sample was incubated for 27 hours at 20.5° C. and for 18.5 hours at 30° C.
*ΔTS = % increase in Tensile Strength of paper over control (no collagen) made with 1% soluble collagen added to pulps made from Old News Print (ONP) or Old Corrugated Containers (OCC).
f(—) indicates analysis not performed.

This data illustrates an increase in soluble collagen throughout the reaction as shown by increases in viscosity and hydroxyproline concentration in the supernatant fraction. The increase in soluble collagen is correlated with an increase in the tensile strength of paper to which the collagen was added. Samples kept at 30° C. after 27 hours of reaction demonstrated progressive conversion of high molecular weight collagen to degradation products (increase in HPLC peak 3), but in this case the lower molecular weight did not result in a similar decrease in tensile strength of papers to which it was added. This latter effect indicated that the collagen has a positive effect on the paper even when some of the material has been digested to relatively low molecular weights. Gel electrophoresis indicates the presence of significant concentrations of approximately 200,000 dalton collagen and approximately 100,000 dalton collagen even after reaction at 30° C. for 18.5 hours. Thus, in the absence of detergent there may be significant amounts of 300,000 or higher molecular weight material. Substantial high molecular weight collagen was present as evidenced by the high areas of HPLC peaks 1 and 2 in samples indicated by footnotes c and d.

times, 200 ml samples were removed, the pH adjusted to between 3.0 and 3.5, and the samples stored at 4° C. The results fr s reaction and the results of tensile tests run on papers made with these materials are shown in Table 4A below.

This data demonstrates that, although not all of the collagen was initially soluble (hydroxyproline measurements increased throughout the reaction), there was a rapid decrease in collagen number average molecular weight throughout the course of the 30° C. reaction period as indicated, for example, by the viscosity decrease and increase in HPLC peak 3 area. This decrease in molecular weight did not effect the gain in tensile strength until all of HPLC peak 1 (number average molecular weight>300,000 daltons) and nearly all of HPLC peak 2 (number average molecular weight ~300,000 daltons) were converted to smaller fragments. Gel electrophoresis indicated the presence of a small amount of ~100,000 dalton molecular weight collagen even after 25.5 hours at 32° C. Most of the collagen has been converted to fragments with number average molecular weights less than 100,000 daltons by this time. HPLC analysis of this sample, which is done in the absence of detergent, indicates no peak 1 and a small of peak 2. The remaining 100,000 dalton number average molecular weight fragments seen on the gel presumably aggregate in the absence of detergent to form the 300,000 dalton triple helix seen as HPLC peak 2. It is this triple helical collagen that appears to impart the enhanced properties to the paper.

TABLE 4A

Summary of Results for Example 10A

| Incubation Time (hrs) | Peak Area | | | Viscosity (cps) | Hydroxyproline in Supernatant (mg/mL) | ΔTS (% Change From Control) |
|---|---|---|---|---|---|---|
| | Peak 1 ~31 min. | Peak 2 ~34 min. | Peak 3 ~45 min. | | | |
| 0 | 2.1 | 29.1 | — | 1260 | 0.28 | +48 |
| 2 | 25.8 | 25.6 | 12.5 | 705 | 0.27 | — |
| 3 | 26.8 | 24.9 | 19.3 | 520 | 0.29 | — |
| 4 | 20.4 | 31.1 | 37.2 | 215 | 0.32 | +46 |
| 5 | 18.8 | 28.8 | 46.1 | 165 | 0.29 | — |
| 6 | 19.9 | 31.7 | 65.3 | 75 | 0.34 | +37 |
| 7 | 13.3 | 28.8 | 72.2 | 35 | 0.35 | +41 |
| 8 | 14.7 | 23.8 | 83.9 | 20 | 0.37 | +41 |
| 9 | 10.6 | 22.1 | 93.9 | 15 | 0.37 | +47 |
| 12.5 | 6.5 | 16.7 | 105.5 | 10 | 0.39 | +41 |
| 25.5 | 0 | 5.0 | 127.6 | 5 | 0.38 | +30 |

Example 11A

Reactions of microbial proteases with the collagen from limed splits as described above were as summarized in Tables 5A and 6A:

Microbial proteases were reacted with ground limed splits from two sources at 17° C. A summary of the optimum results with regards to protease concentration and pH is shown in Table 5A.

TABLE 5A

Reaction of Microbial Proteases with Ground Limed Splits

| Enzyme | pH | Maximum Viscosity (20 rpm) | Hrs. to Maximum Viscosity |
|---|---|---|---|
| Newlase II (0.08 g) | 2.6 | 1840 | 18 |
| Quest AP (0.08 g) | 2.6 | 1535 | 22 |
| AFP 2000 (0.08 g) | 2.6 | 1415 | 22 |
| EDC-APA (0.08 g) | 2.5 | 1085 | 18 |

TABLE 6A

Reaction of Microbial Proteases with Teepak Limed Splits

| Enzyme | pH | Maximum Viscosity (20 rpm) | Hrs. to Maximum Viscosity |
|---|---|---|---|
| Newlase II (0.075 g) | 2.6 | 1386 | 19 |
| Quest AP (0.08 g) | 2.6 | 945 | 24 |
| EDC-APA (0.08 g) | 2.5 | 745 | 20 |
| Newlase A (0.04 g) | 2.6 | 665 | 23 |
| AFP 2000 (0.08 G) | 2.6 | 515 | 41 |
| EDC-APB (0.08 g) | 3.0 | 435 | 39 |

All of the microbial proteases produce significantly viscous collagen solutions, demonstrating their use for solubilizing collagen from ground limed splits.

Collagen solutions prepared by the above examples appear to be stable at room temperature for 12–24 hours, and stability can be enhanced by increasing solution pH to 3.0–3.5 and/or by reducing the solution temperature to 5°–10° C.

The process has demonstrated the feasibility of production of a low-cost soluble collagen product by the substantially complete solubilization of beef hide collagen (ground limed-splits). The process can be conducted at near-ambient conditions and is relatively easy to control. Of particular interest is the recycle method that reduces the cost of the relatively expensive proteolytic enzymes.

Example 12A

Preparation of Ground Limed Splits At High pH.

The "USDA" procedure for producing ground limed splits, described in Example 4A, was modified to simplify and to reduce the cost of this process. For example, approximately 660 pounds (wet weight) of limed splits were processed without titrating to the isoelectric point as in Example 4A. The splits were cut into approximately 12 inch wide strips, which were passed through a strip cutter and then through a rotary knife cutter, as before. However, all of this material, at approximately pH 11, was then passed directly through the Urshel Comitrol with a 0.06 inch cutting head. During the Comitrol grinding, approximately 1.5 parts of Philadelphia, Pa. tap water was added to 1.0 part of splits to reduce temperature rise during the grinding. The resulting ground splits were solubilized by adding the entire batch to approximately 7350 gallons of Claremont, NH tap water at approximately 22° C., adding the contents of a total of 9×6-pound bottles of concentrated HCl and 7×500-gram bottles of crude pepsin. After approximately 37 hours, the collagen was nearly completely hydrolyzed to yield a solution of approximately 0.27% collagen solids, at pH of approximately 2.38, and with a viscosity of approximately 875 cps, as measured with the Brookfield viscometer, Model LVF with a #2 spindle. Thus, grinding the limed splits at high pH had no detrimental effect on the resulting properties of the collagen solution, as was taught by the work of Komanowsky et al., cited herein.

B. Second General Embodiment

The second general embodiment typically utilizes the solubilized collagen produced in the first general embodiment or if desired solubilized collagen can be obtained from other methods. One major advantage of using the solubilized collagen of the first general embodiment is of course the low cost of the material so produced. This cost factor is a major advantage in the paper making art.

The invention improves the strength of recycled paper, conventional paper, and mixtures thereof. The invention is especially useful in producing recycled paper because recycled paper made from recycled cellulosic fibers is generally weaker than paper made from virgin cellulose fibers. As used herein the feedstocks in the invention typically are: virgin paper pulp which is paper pulp made from nonrecycled materials; broke which is scrap at the papermaking plant; reclaimed newsprint which is recycled newspaper and similar paper; reclaimed corrugated container which is recycled old corrugated container and similar material; similar cellulose based papers; and mixtures thereof.

The invention discloses the use of collagen solubilized with enzymes to improve the strength and other properties of paper type products made from cellulose fibers. Typically the method for making a collagen strengthened paper comprises mixing feedstock with water, or water and caustic (e.g. NaOH), and mechanically pulping until a pulp slurry is formed. Preferably the pulp slurry has a consistency of about 3 to about 6 wt % based on dry pulp solids. The pulp slurry is then diluted to a consistency of about 1 to about 3 wt % based on dry pulp solids and adjusted to a pH of about 3.5 to about 7.0. Between about 0.1 to about 2 dry wt % solubilized collagen is added to the diluted pulp slurry, and the resulting slurry is mixed at a shear rate and a time effective for interaction of the diluted pulp slurry solids and soluble collagen, whereby a substantial portion of the solubilized collagen is bound to the paper pulp to form a collagen-pulp slurry. The collagen-pulp slurry is then diluted, preferably to between about 0.1 and 1 dry wt % consistency, and finally the collagen-pulp slurry is formed into a sheet and dried.

Example 1B

Collagen solutions as a coating.

The old newsprint (ONP) or the old corrugated container (OCC) was shredded and soaked in a 1 percent sodium hydroxide solution overnight.

The shredded material was pulped in a Tappi disintegrator for 15 minutes. The pulp was mixed with additional water and a sheet was formed in a Noble and Wood headbox with a Duotex 162-DD-226 forming fabric. The sheet was wet-pressed on the Noble and Wood and then calendered to increase density (blotter paper was used on each side and the gap on the calender rolls was set at 0.76 mils). The sheet was dried on a hot plate surface temperature of about 100° C. under tension for 1 minute. Collagen hydrolysate (MW<2000 daltons) supplied by Secol (Exton, Pa.) or soluble native collagen (MW>300,000 daltons) supplied by Gattefosse' Corp. (Elmsford, N.Y.) were applied to the sheets of recycled paper using either a No. 10 or No. 20 wire-wound rod. The coated sheets were dried either in a forced air oven at 100° F. for 10 minutes or allowed to dry at ambient conditions overnight. The coated sheets were evaluated for basis weight, burst strength, and tensile properties as reported in Table 1B. This table also details amount of pulp and coating weight used.

Gains of tensile strength were observed in all samples tested, ranging from about 125–300 percent over the appropriate control without collagen. While ONP and OCC controls were only approximately 25% as strong as the Kraft paper standard, several coated samples were as strong or stronger than the Kraft standard.

TABLE 1B

Collagen Applied as a Coating

| | Sheet Composition | | | | Physical Characteristics | | | Tensile Properties | | |
|---|---|---|---|---|---|---|---|---|---|---|
| Sample No. | Gms. Fiber | Fiber | Collagen Solution/% | Rod | Drying Technique | Basis Weight kg/279 m² | Mullen Burst Strength MPa | Caliper mm | TS/BW | TS MPa | % Change from Control |
| CC-1 | 5.5 | Kraft | None | — | — | 13.1 | .159 | .11 | 1.30 | 17.01 | — |
| CC-2 | 5.5 | ONP | None | — | — | 12.5 | .034 | .18 | 0.33 | 4.08 | — |
| CC-4 | 5.5 | ONP | Hydrolysate | 20 | oven | 17.6 | .108 | .13 | 1.27 | 22.34 | +289 |
| CC-5 | 5.5 | ONP | " | 20 | air | 17.1 | .109 | .13 | 1.06 | 18.20 | +151 |
| CC-6 | 5.5 | ONP | " | 10 | air | 15.3 | .092 | .12 | 1.32 | 20.24 | +304 |
| CC-7 | 5.5 | ONP | " | 10 | oven | 16.8 | .108 | .13 | 1.15 | 19.38 | +253 |
| CC-8 | 5.5 | ONP | Native | 10 | air | 13.3 | .102 | .11 | 1.11 | 14.71 | +238 |
| CC-9 | 5.5 | ONP | " | 10 | oven | 14.0 | .109 | .12 | 1.02 | 14.22 | +211 |
| CC-10 | 5.5 | ONP | " | 20 | air | 14.4 | .112 | .12 | 1.09 | 15.76 | +235 |
| CC-11 | 5.5 | ONP | " | 20 | oven | 13.8 | .098 | .12 | 1.10 | 15.22 | +238 |
| CC-12 | 4.5 | OCC | None | — | — | 14.4 | .055 | .19 | 0.38 | 5.50 | — |
| CC-14 | 4.5 | OCC | Hydrolysate | 20 | oven | 18.2 | .178 | .14 | 1.47 | 26.68 | +283 |
| CC-15 | 4.5 | OCC | " | 20 | air | 18.8 | .137 | .15 | 1.09 | 20.45 | +185 |
| CC-16 | 4.5 | OCC | " | 10 | air | 17.7 | .161 | .14 | 1.47 | 25.98 | +284 |
| CC-17 | 4.5 | OCC | " | 10 | oven | 17.2 | .161 | .13 | 1.54 | 26.41 | +302 |
| CC-18 | 4.5 | OCC | Native | 10 | air | 13.8 | .124 | .12 | 1.02 | 14.01 | +166 |
| CC-19 | 4.5 | OCC | " | 10 | oven | 13.8 | .13 | .12 | 1.12 | 15.5 | +194 |
| CC-20 | 4.5 | OCC | " | 20 | air. | 14.0 | .12 | .13 | 0.86 | 12.1 | +126 |
| CC-21 | 4.5 | OCC | " | 20 | oven | 14.0 | .13 | .13 | 0.93 | 13.0 | +146 |

Example 2B

Native collagen Added to Pulp in Headbox

The ONP or OCC was shredded and soaked in a 1 percent sodium hydroxide solution overnight. The material was pulped in a Tappi disintegrator for 15 minutes. The pulp was put in the headbox of the Nobel and Wood, and water at various temperatures (14°–17° C. or 36°–38° C.) was added. The pH of the slurry was 7. Various amounts of native collagen solution (0.3% solids) were added. The slurry was allowed to settle and stand for 4 to 10 minutes. The sheet was formed on a Duotex 162-DD-226 forming fabric. The sheet was wet-pressed on the Noble and wood and then calendered to increase density. (Blotter paper was used on each side and the gap on calender rolls was set at 0.762 mm). The sheet was dried on a hot plate for 1 minute. The formed sheets were evaluated for basis weight, burst strength, and tensile properties as reported in Table 2B. This table also details the amount of pulp and collagen additive used. Gains of tensile strength were observed in all samples tested, ranging from about 140–350% over the appropriate control without solubilized collagen. While ONP and OCC controls were approximately 25% as strong as the Kraft paper standard, several samples were stronger than the Kraft standard. No correlation was observed between the amount of collagen added and the tensile strength improvement.

machine's dryer section consists of two banks of 91 cm diameter dryer cans, seven cans in the first section and five cans in the second section. Between the dryer sections is a size press arrangement which can be

TABLE 2B

Collagen Added to Pulp

| | Sheet Composition | | | | Physical Characteristics | | | | | |
|---|---|---|---|---|---|---|---|---|---|---|
| | | | Native Collagen | | Slurry | Basis | Mullen Burst | | Tensile Properties | |
| Sample No.* | Gms Fiber | Fiber | Added % | Headbox Time | Temp. °C. | Weight kg/279 m² | Strength MPa | Caliper mm | TS/BW | TS MPa | % Change from Control |
| CP-1 | 5.5 | Kraft | — | — | — | 13.1 | .159 | .11 | 1.30 | 16.97 | — |
| CP-2 | 5.5 | ONP | — | — | — | 12.5 | .034 | .18 | 0.33 | 4.07 | — |
| CP-5 | 5.5 | ONP | 1 | 4 | 17.1 | 14.3 | .092 | .13 | 1.11 | 15.82 | +240 |
| CP-6 | 5.5 | ONP | 1 | 4 | 35.9 | 13.1 | .071 | .12 | 1.01 | 13.19 | +210 |
| CP-7 | 5.5 | ONP | 2 | 4 | 15.4 | 13.3 | .103 | .11 | 1.48 | 19.70 | +353 |
| CP-8 | 5.5 | ONP | 2 | 4 | 15.4 | 13.9 | .081 | .12 | 0.98 | 13.62 | +201 |
| CP-9 | 5.5 | ONP | 1 | 10 | 37.6 | 13.2 | .089 | .12 | 1.08 | 14.20 | +231 |
| CP-10 | 5.5 | ONP | 10 | 10 | 35.7 | 16.2 | .110 | .14 | 1.07 | 17.33 | +227 |
| CP-11 | 4.5 | OCC | — | — | — | 14.4 | .055 | .19 | 0.38 | 5.48 | — |
| CP-14 | 4.5 | OCC | 1 | 4 | 14.5 | 13.0 | .132 | .11 | 1.48 | 19.24 | +289 |
| CP-15 | 4.5 | OCC | 1 | 4 | 38.3 | 13.5 | .111 | .12 | 0.90 | 12.18 | +138 |
| CP-16 | 4.5 | OCC | 2 | 4 | 14.9 | 13.2 | .146 | .11 | 1.79 | 23.68 | +371 |
| CP-17 | 4.5 | OCC | 2 | 4 | 37.1 | 12.4 | .089 | .11 | 1.06 | 13.13 | +179 |
| CP-18 | 4.5 | OCC | 1 | 10 | 35.3 | 12.7 | .096 | .11 | 1.10 | 13.91 | +189 |

*All samples except CP-1 were soaked in NaOH.

Example 3B

The examples below illustrate: (1) fiber stocks prepared from old corrugated containers (OCC) and old newsprint (ONP); (2) the addition of 1% solubilized collagen to those stocks either before or after the paper sheet is formed. The feedstocks were used to prepare a lightweight, 13.6 kg/279 m², basis weight paper. Some stocks were treated with caustic soda at ambient water temperature. Solubilized collagen was added to the stock chest before paper production in the ratio of 1% of the dry pulp solids, and mixed for at least 15 min. at a temperature of less than 39° C. The papers were produced as follows:

A. Materials

1. Solubilized collagen prepared as in Example 5A.
2. Post consumer old newsprint (ONP).
3. Liner board (rolls) used as old corrugated container (OCC) did not contain corrugated medium—Stone Container, Savannah, Ga. The pulped material is, however, the as if corrugated materials had been used.
4. Concentrated HCL (31%).

B. Equipment:

1. Black Clawson 2.4 m HCVY Hydrapulper 61 cm bottom Vokes rotor and drive assembly—7570 liter capacity.
2. Sprout-Waldron 30 cm Twin-Flow refiner—1770 rpm equipped with plates D5B053 motor end and D5B054 control end.
3. Sandy Hill Corporation manufactured (1967) Four-drinier type paper machine with a 97 cm wire width. The table has a forming length of 44.3 meters. The slice width is 84 cm and the machine was operated with edge curls. The machine's press section consisted of two presses, the first one being a straight through double felted and the second being a bottom-felted reversed press. Each press nip is limited to 2.06 MPa. The bottom press rolls have rubber venta nip covers. The top roll in the second press has a stonite cover. The operated as a horizontal or a vertical unit. With proper rolls installed, the unit can also be used as a breaker stack. Following the second dryer section is an eight roll, seven nip calender stack. Rolls up to 102 cm in diameter can be wound on the reel.

C. Paper stock:

100% OCC/530 kg (oven dried)

Old corrugated container was dispersed in ambient temperature water using pulper No. 1. The dispersed old corrugated container stock was pumped to a 26,500 liter refiner chesstandard freenfrom 644 Canadian standard freeness (CSF) to 325 CSF in 145 minutes.

100% ONP/552 kg (oven dried)

Old newsprint was dispersed in 66° C. water using pulper No. 1. The dispersed old newsprint stock was pumped to a 26,500 liter refiner chest and refined from 135 CSF to 107 CSF in 30 minutes.

100% OCC/854 kg (oven dried)

1. Dispersed old corrugated container in ambient temperature water using pulper No. 1.
2. Pumped dispersed stock to 26,500 liter refiner chest.
3. Refined stock from 638 CSF to 353 CSF in 200 minutes.

100% ONP/871 kg (oven dried)

1. Dispersed ONP in 66° C. temperature water using pulper No. 1.
2. Pumped dispersed stock to 7000 gallon refiner chest.
3. Refined stock from 119 CSF to 99 CSF in 42 minutes.

D. Paper Machine Operations:

Stock from the paper machine chest was pumped via a Fischer-Porter flow controller to the suction side of a fan pump. The thick stock was then diluted with white water to operate the stock flow system. Production rate on the machine was controlled by the amount of the thick stock flowing into the fan pump. The stock was then pumped through an explosion chamber manifold into the primary headbox. The headbox was operated under vacuum with a top holey roll. Machine speed was approximately 175 ft/min. resulting in a paper throughput of about 300 lbs./hr.

Wire Set-Up

The forming fabric on the 91 cm Fourdrinier paper machine was a design 463 Monoflex JDL 145×120 mesh double layer with: forming Board, three 7.6 cm diameter table rolls, five foil boxes with four foils each, four flat boxes with adjustable vacuum.

Paper property (e.g. tensile strength, tear strength, burst strength) improvements obtained from the 1% solubilized collagen additions (Table 4B). For the mixed fiber stocks, machine direction tensile strength improvements were in the range of 25–30% while improvements in the 100% old corrugated containers and old newsprint stocks were in the range of 15–20%.

Biological oxygen demand (BOD) effects from the addition of the solubilized collagen to the mixed fiber were essentially improved over the plain fiber papers themselves, indicating increased retention of paper solids when solubilized collagen was added.

Surface pH measurements of all the papers produced during the trials were acidic even though the water at the papermaking facilities averaged pH 7 for the month of January, which is typical for the water supply. The solubilized collagen-containing papers showed somewhat lower pHs (more acidic) than the other papers. For some eventual end-use applications, it may eventually be desirable to bring the pHs of the solubilized collagen-containing papers to a more neutral level, after the papers have been formed.

TABLE 3B

Properties of Control Papers from Example No. 3B[1]

| Sample No. | Paper Identification | pH | BW | Tensile St. MD | Tensile St. CD | TS/BW | Tear MD | Tear CD | Caliper | Mullen Burst | BOD |
|---|---|---|---|---|---|---|---|---|---|---|---|
| | | | | Control Papers | | | | | | | |
| 16A | 100% OCC | — | 14.2 | — | — | 1.68 | 71.3 | 76.1 | .10 | .189 | 380 |
| 19A | 75/25 OCC/ONP | — | — | — | — | 1.49* | — | — | — | .151 | — |
| 17CA | 50/50 OCC/ONP | — | 14.1 | — | — | 1.23 | 53.7 | 58.8 | .12 | .113 | 170 |
| 18A | 25/75 OCC/ONP | — | — | — | — | 1.08* | — | — | — | .105* | — |
| 15A | 100% ONP | — | 14.3 | — | — | .93 | 37.1 | 41.1 | .14 | .096 | 190 |

[1]Abbreviations and units are as follows:
BW = Basis Wt., kg/279 m² (lbs./3000 ft²) of paper;
TS = Tensile Strength, MPa;
MD = Machine Direction;
CD = Cross Direction;
Tear = Tear Strength, grams;
Caliper, mm;
Mullen Burst, MPa;
BOD = Biological Oxygen Demand, mg/liter.
*Estimates used for comparison of additives in Table 4B.

TABLE 4B

Properties of Experimental Papers from Example No. 3B[1]

| Sample No. | Paper Identification | pH | BW | Tensile MD | Tensile CD | TS/BW | MD ΔTS/BW | Tear[2] MD | Tear[2] CD | Caliper | Mullen Burst[2] | BOD[2] |
|---|---|---|---|---|---|---|---|---|---|---|---|---|
| | | | | Experimental Papers with 1% solubilized collagen | | | | | | | | |
| 16 | 100% OCC | (3.9) | 13.3 | 25.79 | 11.9 | 1.94 | 15% | 54.0 (24%) | 71.4 (6%) | .10 | .170 (10%) | 260 32% |
| 19 | 75/25 OCC/ONP | (3.9) | 13.3 | 25.87 | 10.73 | 1.91 | 29% | 58.8 | 68.6 | .11 | .145 (4%) | — |
| 17C | 50/50 OCC/ONP | (3.9) | 13.9 | 22.52 | 11.02 | 1.62 | 32% | 56.4 5% | 60.0 2% | .12 | .133 18% | 160 6% |
| 18 | 25/75 OCC/ONP | (3.9) | 14.1 | 19.01 | 9.14 | 1.35 | 25% | 47.6 | 51.2 | .13 | .122 17% | — |
| 15 | 100% ONP | (3.9) | 14.2 | 15.49 | 8.08 | 1.09 | 18% | 37.6 1% | 40.8 (1%) | .13 | .111 16% | 150 21% |

[1]Abbreviations and units are as follows:
BW = Basis Wt., kg/279 m² (lbs./3000 ft²) of paper;
TS = Tensile Strength, MPa;
MD = Machine Direction;
CD = Cross Direction;
Tear = Tear Strength, grams;
Caliper, mm;
Mullen Burst, MPa;
BOD = Biological Oxygen Demand, mg/liter.
Basis weight is the paper weight in kg/279 m² (lbs. per 3000 sq. ft.) of paper
[2]Percentage numbers shown in these columns indicate that the data from the experimental papers were increased/decreased from the data of the equivalent daily control papers.

Example 4B

Mixing of Soluble Collagen and Pulp Fiber Prior to Headbox

Seven aliquots of solubilized collagen samples, prepared as described in Example 8A and collected after 16 or 20 hours, were pooled to yield a collagen solution with approximately 3.5 mg collagen solids/ml and a viscosity of 1150 cps at 20 rpm. Aliquots of this solution were diluted either 8-, 4-, or 2-fold with distilled water, or used undiluted, to give a range of concentrations of approximately 0.44, 1.75 and 3.5 mg collagen solids/ml.

Pulp slurries were prepared from ONP and OCC paper stocks at 3% consistency by shredding the materials, soaking them in 1% NaOH overnight, rinsing the soaked solids in tap water, and pulping the rinsed solids in a Tappi disintegrator for 15 minutes.

The pulp slurry was heated on a hot plate with manual stirring to approximately 120°–125° F. An aliquot of the heated pulp slurry (183 g) was combined with an aliquot of one of the diluted collagen solutions (63 g), and the combined collagen-pulp slurry was stirred by a blade-type mixer for 15 min. The resulting consistency of the pulp in the slurry was about 2.2%. The collagen solids to pulp solids ratio for these experiments therefore were approximately 0.5%, 1%, 2% and 4%. The initial temperature of the pulp-collagen slurry was approximately 106° F.+/–3° F. (41° C.+/–2° C.), and this temperature decreased to approximately 95° F. by the end of the stirring period.

At the end of the mixing period, the collagen-pulp slurry was put in the headbox of the Nobel and Wood handsheet system and collected by drainage through a Duotex 162-DD-226 forming fabric. The formed sheet was wet pressed, then calendered between blotter paper with the calender gap set at 30 mils. The sheet was then dried on a hot plate under tension for 1 min. Handsheets were equilibrated overnight in a controlled environment room (72° F./50% RH), then evaluated for basis weight (BW) and tensile strength (TS). Three sheets were prepared and tested for each sample condition. Results are summarized in Table 5B.

This example illustrates that increasing concentrations of dissolved collagen, when added to constant amounts of secondary pulp fiber, generally results in increases in tensile strength of sheets formed from the combination. The only exception in the data of Table 4B was for the OCC sheets with 0.5% added collagen, which yielded a corrected average Tensile Strength (TS/BW) slightly lower than the OCC control Tensile Strength (–8.1%). This apparently inconsistent value is believed to have resulted from the consistently higher Basis Weights of the papers containing collagen (approximately 15% higher than control for the OCC sheets), which is believed to have resulted from the increased retention of pulp fines (small pulp fibers) in these samples. More fines, which would generally produce weaker papers, would tend to suppress the strength of the resulting paper, as in the 0.5%/OCC datum cited. This data clearly illustrates the general property of the collagen additive as a retention aid in paper formation.

As more collagen was added to either pulp slurry, the resulting paper strength increased, but the gain of strength was not linearly proportional to the amount of collagen added; the strength enhancement tended to decrease with increasing collagen/pulp ratio. This observation is consistent with a process of interaction of soluble collagen molecules with pulp fibers that results in saturation of the fiber surfaces with adsorbed collagen molecules. The strength enhancement observed in this binding process is believed to result from inter-fiber bridges formed by soluble collagen molecules; saturation of the fiber surfaces with bound collagen would tend to limit the extent of such inter-fiber bridges, and thereby limit the maximum strength enhancement imparted by this process.

In the example cited, the apparent saturation process observed is interpreted as confirmation that interactions between soluble collagen molecules and pulp fiber surfaces is the predominate mechanism of strength enhancement, as opposed to the directly additive strength enhancement behavior that would be anticipated if these were no interactions between two populations of insoluble fibers mixed int he same proportions. In the examples summarized in Table 5B, the OCC fibers appeared to saturate at a lower collagen-to-pulp-solids ratio than did the ONP fibers.

This example also illustrates that the strength enhancement due to interactions between soluble collagen and pulp fibers can occur at temperatures above 40° C., above which collagen molecules would generally be expected to denature thermally. Previous citations have indicated that collagen addition to paper must be made below this denaturation temperature (G. Sauret et al, Le collagne ans la fabrication du papier, Revue A.T.P.I., Vol 33, No. 8, Octobre 1979, pp 374–365). In a preliminary series of experiments (data not included herein), it was observed that if the pulp slurry and collagen solution were mixed at about 40° C. or above at low pulp slurry consistencies (e.g., 0.5% pulp solids), then the collagen tended to precipitate from solution before binding to the pulp fibers, leading to unsatisfactory (speckled) paper surfaces and no significant enhancement of tensile strength. On the other hand, if the pulp slurry and collagen solutions were mixed at higher pulp consistencies (e.g., 2.2% pulp solids as in Table 5B), the collagen does not precipitate and is successfully bound to the pulp fibers.

An additional example on the effect of temperatures in excess of 30° on collagen preparation is provided by the following example. USDA ground limed splits (0.06 inch cutting head) were centrifuged at 4° C. for 20 minutes at 10,000×g and the supernatant liquid was removed. The centrifuged limed splits were added in 7.5 g portions to two 1 L Erlenmeyer flasks that each contained deionized water 750 mL). The suspensions were stirred with a magnetic stirrer (2 inch stir bar), the pH was adjusted to pH 2.1 using concentrated hydrochloric acid, and 0.19 g pepsin was added to each flask. One flask was stirred at 19° C. and the other flask was stirred at 32° C. After 60 hours, the pH of the flasks were adjusted to Proximately 3.5 and the viscosities were measured at 20 rpm. The viscosity of the 19° C. reaction was 620 cps and the viscosity of the 32° C. reaction was 10 cps.

Both collagen preparations were added to pulp (collagen is approximately 1% of pulp) and the ability of these preparations to improve the properties of paper were mea-

TABLE 5B

Summary of Handsheet Properties for Example 4B Tests

| Pulp | Collagen Added % | Avg. BW* (lb/3000 ft²) | Avg. TS* | Avg. TS/BW* | ΔTS (%) |
|---|---|---|---|---|---|
| OCC | 0** | 31.0 | 1330 | 42.9 | — |
| OCC | 0.5 | 36.3 | 1430 | 39.4 | –8.1 |
| OCC | 1 | 35.2 | 1790 | 50.9 | +19 |
| OCC | 2 | 34.9 | 1840 | 52.7 | +23 |
| OCC | 4 | 35.7 | 1930 | 54.1 | +26 |
| ONP | 0** | 28.0 | 1370 | 48.9 | — |
| ONP | 0.5 | 32.7 | 1740 | 53.2 | +8.8 |
| ONP | 1 | 33.2 | 1930 | 58.1 | +19 |
| ONP | 2 | 31.8 | 2020 | 63.5 | +30 |
| ONP | 4 | 34.1 | 2400 | 70.4 | +44 |

*Average of 3 handsheets
**Control handsheets
BW = basis weight, lbs/3000 sq. ft. of paper;
TS = tensile strength sured. The preparation made at 19° provided no tensile strength/basis weight enhancement.

This shows that completely hydrolyzed soluble collagen does not appear to contribute to enhancement of tensile strength. The measurement of viscosity below about 20 cps does not appear sufficient to predict the degree of strength enhancement of paper mode with these solutions.

While the various examples above have focused on papermaking the invention could also be used in the making of various products such as molded products or paperboard where a cellulosic pulp can be bonded by solubilized collagen.

Various types of water such as Columbus, Ohio tap water; Savannah, Ga. tap water; whitewater from the papermaking process; and whitewater reduced in solids content were used; thus, it appears that the type of water is not critical in the invention for either the collagen making process or the papermaking process and a wide latitude for water supplies is possible.

The following examples illustrate the use of the claimed inventions in a large-scale papermaking process and the benefits to be achieved thereby. In particular, it has been observed that the use of soluble collagen as disclosed herein in a papermaking process not only increases properties of the resultant paper product, but also soluble collagen allows for certain process improvements such as higher recovery of fines, higher machine speeds, higher drainage rates and decreased BOD values. Soluble collagen may be of value not only as a strengthening additive, but also as a retention aid, sizing additive, thickening agent, etc.

Example 5B

A trial was run at APC paper to establish the safety of adding pepsin solubilized collagen to a papermaking system; to scale up pepsin solubilized collagen production using Teepak ground splits; and to establish procedures for adding pepsin solubilized collagen to a papermaking process. This trial was the first attempt at large scale use of pepsin solubilized collagen and logistics for future trials were established.

Standard 30 lb. basis weight paper was produced on APC's paper machine at about 750 fpm. Twenty-six hundred (2600) gallons of pepsin solubilized collagen were produced from 450 lbs. of Teepak ground limed splits. The pepsin solubilized collagen was pumped from the tank to the machine chest where it mixed with the pulp.

The following is a description of the process. Furnish was made with the normal level of polymer additions and standard fiber furnish at a pH of 6.2. APC polymer addition was then decreased by 50%. When the machine was stabilized, pepsin solubilized collagen was added to the system at 1% of the dry pulp weight. When the machine thereafter stabilized, the pH was adjusted to 4.0. When the machine had stabilized at pH 4.0, the pepsin solubilized collagen was run out and the machine was stabilized (with 50% APC polymer addition).

The paper samples were sent for testing in the form of four 30" rolls for each set (labeled A,B,C & D). The testing focused on the machine direction tensile strengths of the samples. Table 6B provides the results from all of the samples. The results show a good cross machine profile of all the sets with the "A" samples coming from the "near" side of the paper machine. Basis weights are given in pounds per three thousand square feet (lbs./3000 ft$^2$). Caliper, or thickness, is measured in thousandths of an inch (0.001"). Tensile results are shown in pounds of load per inch of width (lbs./in). Tensile Index is a measure of the tensile strength of the paper adjusted for its basis weight and is in units of Newton meters per gram (Nm/g). The machine direction tensile index was the primary indicator of the effectiveness of the pepsin solubilized collagen to add strength to the paper.

TABLE 6B

Trial 1 Sample Test Results

| Sample | | Basis Weight | Caliper | MD Tensile | MD Tensile Index |
|---|---|---|---|---|---|
| 2 Begin | A | 29.5 | 3.49 | 18.3 | 68.5 |
| | B | 31.0 | 3.66 | 19.1 | 68.1 |
| | C | 30.4 | 3.53 | 18.0 | 65.5 |
| 2 Middle | A | 30.8 | 3.46 | 18.3 | 65.7 |
| | B | 30.6 | 3.59 | 16.7 | 60.4 |
| | C | 31.2 | 3.45 | 18.2 | 64.6 |
| 2 End | A | 30.9 | 3.63 | 18.1 | 64.9 |
| | B | 31.2 | 3.60 | 18.4 | 65.2 |
| | C | 30.0 | 3.59 | 17.7 | 65.3 |
| 3 Begin | A | 31.5 | 3.74 | 18.2 | 63.8 |
| | B | 30.7 | 3.76 | 17.2 | 62.0 |
| | C | 31.7 | 3.68 | 17.6 | 61.3 |
| 3 Middle | A | 31.9 | 3.83 | 19.2 | 66.5 |
| | B | 30.4 | 3.66 | 17.0 | 61.7 |
| | C | 32.0 | 3.73 | 17.8 | 61.5 |
| 3 End | A | 31.8 | 3.66 | 18.5 | 64.4 |
| | B | 30.3 | 3.64 | 17.5 | 63.8 |
| | C | 31.5 | 3.65 | 16.8 | 58.9 |
| 4 Begin | A | 32.5 | 4.01 | 19.3 | 65.8 |
| | B | 31.4 | 3.96 | 17.5 | 61.6 |
| | C | 32.5 | 3.95 | 19.7 | 66.9 |
| 4 Middle | A | 31.2 | 3.84 | 17.9 | 63.5 |
| | B | 31.2 | 3.70 | 19.3 | 68.4 |
| | C | 30.6 | 3.69 | 16.8 | 60.9 |
| 4 End | A | 30.6 | 3.69 | 17.3 | 62.6 |
| | B | 30.4 | 3.64 | 18.2 | 66.1 |
| | C | 30.6 | 3.61 | 18.1 | 65.6 |
| 4 Begin | AA | 32.1 | 3.78 | 19.8 | 68.2 |
| | BB | 30.8 | 3.65 | 17.7 | 63.5 |
| | CC | 31.8 | 3.78 | 19.8 | 69.0 |
| 4 Middle | AA | 31.6 | 3.83 | 18.8 | 65.7 |
| | BB | 29.7 | 3.70 | 16.5 | 61.4 |
| | CC | 31.1 | 3.69 | 18.8 | 66.8 |
| 4 End | AA | 32.0 | 3.80 | 19.0 | 65.8 |
| | BB | 30.8 | 3.90 | 17.5 | 62.8 |
| | CC | 32.3 | 3.88 | 18.2 | 62.3 |
| 5 Begin | A | 31.4 | 4.16 | 17.9 | 63.2 |
| | B | 31.3 | 4.10 | 17.8 | 62.9 |
| | C | 31.9 | 4.15 | 18.9 | 65.5 |
| 5 Middle | A | 30.5 | 3.75 | 16.7 | 60.4 |
| | B | 31.3 | 3.69 | 17.9 | 63.1 |
| | C | 31.1 | 3.68 | 17.9 | 63.5 |
| 5 End | A | 30.8 | 3.71 | 17.4 | 62.6 |
| | B | 30.6 | 3.68 | 17.7 | 64.1 |
| | C | 30.4 | 3.68 | 17.1 | 62.2 |

There were no changes observed in tensile strength with the addition of pepsin solubilized collagen, most likely because of the high quality of fiber used (100% OCC-bag kraft), or the dynamic nature of the paper machine, which was difficult to stabilize.

Example 6B

Another trial was run at APC in order to produce the pepsin solubilized collagen from limed splits ground at the USDA and to remove completely APC's polymer additives from the system when the pepsin solubilized collagen was added.

Standard 30 lb basis weight paper was produced. Twenty-five hundred (2500) gallons of pepsin solubilized collagen were made from 470 pounds of neutralized and frozen limed splits ground at the USDA. The pepsin solubilized collagen was pumped from its tank to the machine chest where it mixed with the pulp. About 10 to 15 minutes of mixing time was allowed.

The following is a description of the trial. The trial was started with standard fiber furnish and no additives at a pH of 7.0–7.2. The pH was lowered to 5.5. The pepsin solubilized collagen was introduced into the machine. The pH was increased from 5.3 to 5.9. The pH was adjusted to 5.5–6.0, while pepsin solubilized collagen was emptied from the system. No additives were in the system at the end of trial.

The paper samples were sent for testing in the form of four 30" rolls for each set (Sets A,B,C & D). Like the first trial, the testing focused on the machine direction tensile strengths of the paper. Table 7B summarizes the sample test results. The results show a good cross machine profile of the samples with the "A" sample coming from the near side of the paper machine.

The pepsin solubilized collagen produced for this trial was made at about 14° C. Because the reaction proceeded slower at this lower temperature, all of the splits did not become digested. Only a minimum increase in viscosity occurred after two days. This may have been the primary reason that no improvements were observed in tensile strength. As can be seen in Table 8B, Sample 3 had an average tensile index of 64.8, as compared to 67.6 and 65.7 for the controls. Another reason for the lack of improvement in tensile strength is that the controls contained no additives which aid in the retention of fines. The controls may have had less fines and more "quality" fibers, which could have yielded greater tensile values for those samples. The X samples were taken during a transition period when the pepsin solubilized collagen was emptying, and the pH was fluctuating. Results for the X samples were included in Tables 7B and 8B only for comparison purposes.

TABLE 7B

Trial 2 Sample Test Results

| Sample | | Basis Weight | Caliper | MD Tensile | MD Tensile Index |
|---|---|---|---|---|---|
| 3 | A | 30.9 | 3.7 | 17.4 | 62.3 |
| | B | 30.9 | 3.7 | 18.5 | 66.2 |
| | C | 31.7 | 3.7 | 18.6 | 64.9 |
| | D | 31.8 | 3.7 | 18.9 | 65.7 |
| x | 1 | 32.2 | 3.7 | 17.7 | 60.9 |
| | 2 | 31.4 | 3.7 | 17.2 | 60.7 |
| | 3 | 32.2 | 3.7 | 16.3 | 55.9 |
| | 5 | 32.0 | 3.6 | 20.8 | 72.0 |
| | 6 | 31.0 | 3.5 | 18.3 | 65.2 |
| | 7 | 32.5 | 3.6 | 20.2 | 68.7 |
| 1 | A | 31.2 | 3.6 | 19.0 | 67.2 |
| | B | 30.7 | 3.6 | 20.0 | 72.1 |
| | C | 30.7 | 3.6 | 18.7 | 67.2 |
| | D | 32.1 | 3.7 | 18.6 | 64.0 |
| 1 | A^2 | 31.1 | 3.7 | 18.7 | 66.7 |
| | B^2 | 31.4 | 3.6 | 19.5 | 68.7 |
| | C^2 | 31.7 | 3.7 | 18.6 | 64.8 |
| | D^2 | 31.9 | 3.6 | 18.0 | 62.6 |

TABLE 8B

Trial 2 Test Results Summary

| Sample | Description | Basis Weight | Caliper | MD Tensile | MD Tensile Index | Padpak Grade |
|---|---|---|---|---|---|---|
| 3 | OCC, Ph = 5.3–5.9, pepsin solubilized collagen | 3.13 | 3.7 | 18.3 | 64.8 | 9 |
| x | OCC, pH = 5.5–6.0, pepsin solubilized collagen | 31.9 | 3.6 | 18.4 | 63.9 | 10 |

TABLE 8B-continued

Trial 2 Test Results Summary

| Sample | Description | Basis Weight | Caliper | MD Tensile | MD Tensile Index | Padpak Grade |
|---|---|---|---|---|---|---|
| 1 | OCC, pH = 7.0–7.2, Control | 31.2 | 3.6 | 19.0 | 67.6 | 10 |
| 1^2 | OCC, pH - 7.0–7.2, Control | 31.5 | 3.7 | 18.7 | 65.7 | 5 |

The following conclusions and observations were made from Trial 2: APC's polymer additive was successfully removed from the system without any operating problems; pepsin solubilized collagen was then added to the APC system with no problems; limed splits ground at the USDA were a suitable source of collagen. In addition, it was found that if the temperature of the pepsin solubilized collagen was too low an incomplete reaction resulted (no significant viscosity was developed); and the low quality pepsin solubilized collagen yielded no tensile strength increases. Again, a 100% OCC pulp was used. The handsheet studies showed that the greatest strength increases in tensile occurred when ONP or other weaker fibers were in the furnish.

Since the temperature of the water in the pepsin solubilized collagen mixing tank was too low to complete the reaction, during winter months, it would be advantageous to either install a heat exchanger or to fill the tank a week in advance to allow the water to warm up.

Example 7B

The objectives of this trial were to establish procedures for running mixed OCC/ONP furnish and to scale up pepsin solubilized collagen production using limed splits ground at the USDA.

Standard 30 lb. basis weight paper was produced at about 825 fpm. Thirty-nine hundred (3900) gallons of pepsin solubilized collagen were produced in a ~9000 gal. mixing tank. From there, the pepsin solubilized collagen was pumped into a 3000 gal. tank with dilution water being pumped into the machine chest to mix the pulp.

The following is a description of the trial. Standard furnish was on the machine with APC's polymer additive. ONP was introduced onto the machine shortly after the commencement of the trial. Approximately 20% ONP/80% OCC furnish was on the machine with APC's polymer additive. APC's polymer additive was cut off, and the machine was stabilized with no polymer. Pepsin solubilized collagen was pumped in at the machine chest, and the machine speed was turned up to 840 fpm. The pepsin solubilized collagen subsequently ran out.

Alternative physical testing was carried out at another location. A wider range of tests were run to see how the samples' properties were overall. The focus was still on machine direction tensile strength. A summary of the properties and their units can be seen in Table 9B.

TABLE 9B

Paper Properties and Units

| Property | Units |
|---|---|
| Basis Weight | 1 g/3000 ft$^2$ |
| Caliper | 0.0001" |

TABLE 9B-continued

| Paper Properties and Units | |
|---|---|
| Property | Units |
| Tear | 100* grams force |
| Tear Index | 100 gf/(g/m$^2$) |
| Tensile | lb/in |
| Tensile Index | (N/m)/(g/m$^2$) |
| Burst | psi |
| Burst Index | kPa/(g/m$^2$) |
| Porosity | s/100 ml |

Table 10B shows the test results of all the paper samples. Samples 1A and 1D were the standard 30 lb. paper normally used. Samples 1, 2 and 3 were 80% standard furnish (consisting of 100% OCC) and 20% news blank (ONP), with pepsin solubilized collagen. Samples 5, 6 and 7 had the identical furnish with no additives, as did 9, 11 and 12, which contained APC's polymer additive. Sample 4C was the same as 1, 2 and 3, except that this sample was taken after the machine speed was increased to 840 fpm. Results from samples within the same group were consistent with the first two trials.

Some wet end tests were run on the stock going to the headbox and the whitewater. These included headbox and whitewater consistencies, first pass retention, BOD, pH and cationic demand. Only a few data points were taken, and the results were extremely inconsistent. For this reason, they are not presented herein. Because these tests are important in the papermaking process, more samples were planned to be taken at the next trial to ensure consistency.

TABLE 10B

Trial 3 Sample Test Results

| | Basis | | Tear | | Tensile | | | |
|---|---|---|---|---|---|---|---|---|
| Sample | Weight | Caliper | MD | CD | MD | CD | Burst | Porosity |
| 1A | 31.5 | 3.7 | 48 | 52 | 18.4 | 6.7 | 20.7 | 32.7 |
| 1D | 31.5 | 3.5 | 39 | 53 | 18.7 | 7.2 | 22.8 | 30.0 |
| 1 | 30.6 | 3.6 | 37 | 48 | 18.8 | 7.3 | 20.6 | 23.3 |
| 2 | 30.6 | 3.9 | 39 | 50 | 16.4 | 6.5 | 20.9 | 24.8 |
| 3 | 30.6 | 3.7 | 42 | 53 | 17.2 | 6.5 | 20.5 | 28.2 |
| 5 | 30.5 | 3.5 | 36 | 46 | 17.8 | 6.3 | 19.3 | 25.4 |
| 6 | 30.5 | 3.5 | 37 | 49 | 16.7 | 6.2 | 19.4 | 28.4 |
| 7 | 30.5 | 3.5 | 40 | 49 | 16.9 | 7.0 | 21.5 | 30.5 |
| 9 | 30.2 | 3.4 | 37 | 49 | 17.4 | 7.3 | 18.5 | 25.0 |
| 11 | 30.2 | 3.7 | 42 | 49 | 16.8 | 6.6 | 20.7 | 22.5 |
| 12 | 30.2 | 3.5 | 36 | 48 | 17.1 | 6.8 | 20.0 | 18.3 |
| 4C | 32.5 | 4.2 | 44 | 46 | 16.6 | 7.9 | 20.3 | 24.0 |

The results on the paper are summarized in Table 11B. Much like the previous trials, there were no increases in machine direction tensile strength. All of the results were remarkably similar, except 4C. The paper became more "square" when the machine speed was increased. The MD tensile decreased, while the CD tensile increased. In addition, the tear results for each direction become closer in value. All of the samples containing the ONP maintained strength properties nearly that of the 100% OCC standard. One factor that prevented direct comparisons between samples is that the pH was not held constant throughout the trial. It was not known precisely how much, if at all, that the pH affected tensile strength.

TABLE 11B

Trial 3 Sample Test Results

| | | Basis | | Tear Index | | Tensile Index | | Burst | |
|---|---|---|---|---|---|---|---|---|---|
| Sample | Description | Weight | Caliper | MD | CD | MD | CD | Index | Porosity |
| 1A, 1D | OCC, pH = 6.3, APC poly | 31.5 | 3.6 | 85 | 102 | 65.1 | 24.4 | 29.2 | 31 |
| 1, 2, 3 | 80/20, pH = 3.6, pepsin solubilized collagen | 30.6 | 3.7 | 79 | 101 | 63.2 | 24.5 | 2.86 | 25 |
| 5, 6, 7 | 80/20, pH = 5.1 | 30.5 | 3.5 | 76 | 97 | 62.1 | 23.6 | 2.79 | 26 |
| 9, 11, 12 | 80/20, pH = 6.7, APC poly | 30.2 | 3.5 | 78 | 99 | 62.7 | 25.3 | 2.77 | 22 |
| 4C | 80/20, pH = 4.4 | 32.5 | 4.2 | 83 | 87 | 56.5 | 26.9 | 2.65 | 24 |

The following conclusions were drawn from Trial 3. Adding 20% ONP to the furnish did not affect tensile strength. The machine had no operating problems with the ONP in the furnish. No improvements occurred with the addition of pepsin solubilized collagen. The pepsin solubilized collagen could be prepared successfully with limed splits at a high pH (not neutralized prior to grinding). It was difficult to control at low pH, especially when adding pepsin solubilized collagen, on APC's paper machine. Adding 20% ONP to the furnish did not lessen the quality of the resultant paper. The ONP that was added to the furnish was not the lower quality pulp that it was thought to be. A much higher level of news could probably be added with very little effect on the strength of the sheet. Not many wet end samples were taken in this trial. More samples should have been taken throughout the trial, perhaps every ten to fifteen minutes. There was also some difficulty in controlling pH, especially when the pepsin solubilized collagen was added. Running at a higher pH (6 to 7) should allow for better control.

Example 8B

The objectives of this trial were to study the effects of increasing the amount of ONP in the furnish; to carry out a complete wet end analysis on the APC system; and to study the machine parameters controlled by APC's Measurex system. Standard 30 lb. paper was produced at about 855 fpm. Sixty-three hundred (6300) gallons of pepsin solubilized collagen were produced from 580 lb. of limed splits ground at the USDA. The pepsin solubilized collagen was produced in a 9000 gal. mixing tank. From there, the pepsin solubilized collagen was pumped into a 3000 gal. tank with dilution water, before being pumped into the machine chest to mix with the pulp. Wet end samples were taken approximately every 15 minutes. Measurex data was printed out every 15 minutes.

The following is a description of the trial. Furnish with 30% ONP and APC's polymer additive reached the paper machine. The machine was stabilized with 30% ONP and APC's polymer additive. APC's polymer additive was then cut off. Pepsin solubilized collagen was pumped into the machine chest. About 33% ONP was present in the furnish initially. About 37% ONP was present in the furnish later, and increased to about 45% ONP. Pepsin solubilized collagen ran out, and APC's polymer additive was pumped in.

Table 12B summarizes selected key machine parameters used in the triused in the trial. The basis weight held relatively constant throughout, even when the pepsin solubilized collagen was added. The pepsin solubilized collagen addition increased the stock flow from 590 gpm to 680 gpm, a 15% increase in flow. The pepsin solubilized collagen also had an effect on the pH of the thick stock in the machine chest. The pH of the stock started out at 6.8 and got as low as 5.7 before finishing the trial at 6.6. This was expected since the pepsin solubilized collagen entered the machine chest at a pH of 2.1. It could not be determined how the main steam changed when the pepsin solubilized collagen was added, as it fluctuated throughout the trial.

water pH reacted much the same that the thick stock pH did, except that it had a much wider range, from as high as 7.19 down to 5.05.

The first pass retention of samples containing pepsin solubilized collagen were generally about the same as those samples containing APC's polymer. APC's polymer yielded results from 80.6 to 84.5% over time. The retention dropped off at 8:15 to 75.1% with no additives in the system. The samples with pepsin solubilized collagen had retentions as high as 87.0%, although they averaged 81 to 82%. Because the range of retention results was relatively large (72.6 to 87.0%), more samples should be taken and the tests should be run in duplicate.

TABLE 12B

Trial 4 Measurex Data from Paper Machine

| Time | Reel Basis Wt. | Stock flow | Thick Stock pH | Pepsin Solubilized Collagen Flow | Thick Stock Consistency | Machine Speed | Main Steam |
|---|---|---|---|---|---|---|---|
| 7:35 AM | 30.3 | 591.0 | 6.8 | 0.0 | 2.6 | 855.9 | 9.8 |
| 7:50 | 30.3 | 590.7 | 6.7 | 0.0 | 2.6 | 856.0 | 9.8 |
| 8:17 | 30.7 | 599.4 | 6.5 | 0.0 | 2.6 | 855.8 | 10.5 |
| 8:53 | 29.3 | 643.4 | 5.7 | 0.0 | 2.5 | 855.4 | 6.3 |
| 9:26 | 20.7 | 689.4 | 5.9 | 130.1 | 2.4 | 856.0 | 8.2 |
| 9:33 | 31.3 | 692.8 | 6.0 | 127.7 | 2.4 | 856.2 | 8.6 |
| 10:08 | 31.8 | 679.2 | 6.0 | 126.9 | 2.4 | 855.9 | 10.0 |
| 10:19 | 30.4 | 681.7 | 5.9 | 122.8 | 2.4 | 855.7 | 8.2 |
| 10:29 | 32.1 | 687.9 | 5.9 | 0.0 | 2.4 | 855.4 | 8.4 |
| 10:44 | 32.6 | 641.6 | 6.1 | 0.0 | 2.6 | 856.0 | 12.0 |
| 11:17 | 32.0 | 603.9 | 6.5 | 0.0 | 2.6 | 856.0 | 9.8 |

To indicate the dynamics of the system, Table 13B summarizes the wet end parameters. The pepsin solubilized collagen, which was acidic and cooler than the thick stock, lowered the whitewater temperature and pH. The temperature dropped about 3.5° C., from 41.0 to 37.5. The white-

TABLE 13B

Trial 4 Wet End Summary

| Time of Sample | Whitewater Temperature (C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 7:50 AM | — | 6.79 | 3750 | 580 | 84.5 | 886 | 6.5 |
| 8:00 | 41.1 | 7.19 | 3420 | 590 | 82.7 | 954 | 6.4 |
| 8:15 | 40.9 | 6.96 | 3528 | 878 | 75.1 | 980 | 7.2 |
| 8:30 | 42.0 | 5.38 | 4568 | 658 | 85.6 | 800 | 6.0 |
| 8:45 | 40.3 | 5.09 | 3742 | 910 | 75.7 | 837 | 5.5 |
| 9:00 | 39.5 | 5.05 | 3524 | 712 | 79.8 | 550 | 5.2 |
| 9:15 | 38.3 | 5.68 | 4014 | 520 | 87.0 | 428 | 5.5 |
| 9:30 | 38.3 | 6.02 | 3224 | 496 | 84.6 | 537 | 5.3 |
| 9:45 | 38.0 | 6.08 | 3572 | 534 | 85.1 | 464 | 5.5 |
| 10:15 | 37.4 | 5.73 | 3272 | 896 | 72.6 | 733 | 5.0 |
| 10:40 | 38.2 | 5.43 | 3944 | 528 | 86.8 | 518 | 5.4 |
| 11:15 | 37.3 | 6.36 | 3378 | 654 | 80.6 | 770 | 6.8 |

The BOD analyses from the system whitewater dropped from 800 to 900 mg/l down to about 500 to 600 mg/l. The cationic demand of the stock going to the headbox also appeared to drop when the pepsin solubilized collagen was in the system, decreasing from 6.5 to 5.0. This was a measure of how well the pepsin solubilized collagen was "attaching" to the stock, so that it would not fall through the forming wire while the water drained during the paper formation. Results closer to zero indicate a strong interaction with the fibers. These wet end factors were considered while studying the results of the physical testing.

TABLE 14B

Trial 4 Sample Test Results

| Sample | | Basis Weight | Caliper | Tear | | Tensile | | Burst | Porosity |
|---|---|---|---|---|---|---|---|---|---|
| | | | | MD | CD | MD | CD | | |
| 1 | A | 30.17 | 3.7 | 40 | 47 | 18.2 | 7.4 | 20.3 | 27 |
| 7:50 AM | B | 30.17 | 3.5 | 35 | 45 | 19.4 | 7.7 | 19.8 | 19 |
| | C | 30.17 | 3.6 | 35 | 43 | 19.4 | 7.9 | 21.6 | 24 |
| | D | 30.17 | 3.7 | 40 | 43 | 18.5 | 7.2 | 20.1 | 25 |
| 2 | A | 30.24 | 3.6 | 39 | 48 | 19.6 | 7.1 | 21.4 | 36 |
| 8:20 | B | 30.24 | 3.6 | 34 | 44 | 21.2 | 7.6 | 20.8 | 37 |
| | C | 30.24 | 3.5 | 34 | 47 | 21.0 | 7.7 | 22.4 | 40 |
| | D | 30.24 | 3.6 | 39 | 47 | 18.1 | 7.1 | 19.5 | 37 |
| 3 | A | 30.36 | 3.7 | 38 | 48 | 19.2 | 7.3 | 19.8 | 12 |
| 8:45 | B | 30.36 | 3.6 | 34 | 42 | 19.7 | 7.3 | 20.7 | 10 |

TABLE 14B-continued

Trial 4 Sample Test Results

| Sample | | Basis Weight | Caliper | Tear | | Tensile | | Burst | Porosity |
|---|---|---|---|---|---|---|---|---|---|
| | | | | MD | CD | MD | CD | | |
| | C | 30.36 | 3.6 | 42 | 42 | 18.4 | 7.3 | 21.1 | 12 |
| | D | 30.36 | 3.6 | 35 | 45 | 19.8 | 7.7 | 20.0 | 11 |
| 4 | A | 28.97 | 3.5 | 31 | 40 | 19.0 | 8.0 | 21.1 | 17 |
| 9:10 | B | 28.97 | 3.5 | 32 | 39 | 17.8 | 7.4 | 19.9 | 14 |
| | C | 28.97 | 3.7 | 34 | 36 | 18.5 | 7.4 | 19.6 | 13 |
| | D | 28.97 | 3.9 | 37 | 45 | 20.0 | 7.7 | 18.7 | 13 |
| 5 | A | 30.77 | 4.1 | 35 | 46 | 19.1 | 7.0 | 19.1 | 17 |
| 10:20 | B | 30.77 | 4.0 | 32 | 40 | 19.3 | 7.6 | 19.4 | 17 |
| | C | 30.77 | 4.1 | 35 | 45 | 20.5 | 8.5 | 18.8 | 17 |
| | D | 30.77 | 4.1 | 44 | 49 | 17.8 | 8.0 | 18.4 | 14 |
| 6 | A | 32.11 | 4.2 | 41 | 52 | 19.2 | 7.3 | 20.1 | 20 |
| 11:15 | B | 32.11 | 4.1 | 40 | 49 | 20.1 | 7.6 | 20.4 | 20 |
| | C | 32.11 | 4.1 | 43 | 42 | 19.8 | 7.6 | 19.7 | 22 |
| | D | 32.11 | 4.1 | 44 | 48 | 18.5 | 7.1 | 19.7 | 19 |

The physical test results of all the samples are shown above in Table 14B. Rolls A through D have the same designation as for Trials 1 and 2 (Examples 5B and 6B). Like the previous trials there is a good cross machine profile consistency with all of the samples. Most of the samples were comparable to the standard 100% OCC paper that Ranpak typically receives from APC. Up to 45% ONP has now been used with minimal decreases in tensile and tearing strengths.

There appeared to be no tensile strength increases due to the pepsin solubilized collagen addition, which may have resulted from the relatively high quality of fiber used. Handsheet studies have shown that pepsin solubilized collagen was beneficial to the weaker, lower quality fibers. Deinked newsprint may be a better source of weaker fibers than the news blank that was used for Trial 3 (Example 7B) and this trial.

Table 14B summarizes the physical test results from Trial 4. The greatest changes occurred with caliper and porosity. At 45% ONP, the caliper went up to 4.1 from 3.6 at the start of the trial. This occurred with both the pepsin solubilized collagen sample and APC polymer sample. The porosity results for the paper dropped significantly, from 24 sec/100 ml at the start down to 11 sec/100 ml with the first pepsin solubilized collagen sample, indicating the paper was more porous when pepsin solubilized collagen was added.

TABLE 14B

Trial 4 Test Results Summary

| Sample | Description | Basis Weight | Caliper | Tear Index | | Tensile Index | | Burst Index | Porosity |
|---|---|---|---|---|---|---|---|---|---|
| | | | | MD | CD | MD | CD | | |
| 1 | 70/30, APC Polymer | 30.2 | 3.6 | 76 | 91 | 69.2 | 27.7 | 2.87 | 24 |
| 2 | 70/30, no additive | 30.2 | 3.6 | 74 | 95 | 73.1 | 27.0 | 2.94 | 38 |
| 3 | 67/33, <1% pepsin solubilized collagen | 30.4 | 3.6 | 75 | 90 | 70.2 | 27.0 | 2.85 | 11 |
| 4 | 63/37, 1% pepsin solubilized collagen | 29.0 | 3.7 | 71 | 85 | 71.9 | 29.1 | 2.90 | 14 |
| 5 | 55/45, 1% pepsin solubilized collagen | 30.8 | 4.1 | 73 | 90 | 68.9 | 27.9 | 2.60 | 16 |
| 6 | 55/45, APC Polymer | 32.1 | 4.1 | 80 | 91 | 66.8 | 25.5 | 2.63 | 20 |

The following conclusions were reached based on the information from Trial 4. Machine direction tensile strength did not increase with the addition of pepsin solubilized collagen. Adding up to 45% news blank (ONP) in the furnish slightly decreased tensile results. The news blank used in Trials 3 and 4 was almost as good as the OCC used at APC, in terms of the resulting paper tensile strength. First pass retention with pepsin solubilized collagen was as good as with APC's polymer. Cationic demand decreased when pepsin solubilized collagen was added to the system. The BOD of the whitewater decreased about 200 to 300 mg/l when pepsin solubilized collagen was in the system. The porosity results of the pepsin solubilized collagen samples were significantly lower than for all the other samples, indicating that the paper was more porous. Unless there is strict control of the system pH, adding pepsin solubilized collagen lowers the pH and lessens the control over it.

A difficulty in analyzing the data was that there were too many variables changing simultaneously. The furnish composition was changing, pH was fluctuating and the chemicals added to the system were changing. There was little time for the system to completely stabilize. No direct comparisons can thus be made between the samples.

Example 9B

The objectives for this trial were to study the effects of neutral vs. acid conditions on the APC system; to study the effects of pH on the tensile strength of the paper when pepsin solubilized collagen is added; to use a lower quality ONP source—deinked news; and to take more frequent samples for the physical testing and wet end analysis.

At this trial, it was decided to change as few variables as possible. The furnish composition was held constant at 60% OCC and 40% deinked news (ONP).

Standard 30 lb. basis weight paper was produced at about 840 fpm. Five thousand (5000) gallon of pepsin solubilized collagen were made from 570 lb. of limed splits ground at the USDA. Although the viscosity of the pepsin solubilized collagen was good (1100 cps at 20 rpm), there were many large undissolved particles present, probably resulting from contaminating particles that had not passed through the Comitrol during grinding. As before, the pepsin solubilized collagen was pumped to a dilution tank before being pumped into the machine chest. Wet end samples were taken and Measurex data was printed out every 15 minutes. Fifteen minute rolls were made on the winder to send for rewinding and testing.

The following is a description of the trial. The machine was stabilized at 60/40 furnish, with APC's polymer additive, and at pH=7. APC's polymer additive was then cut off. The machine was stabilized with no additives. The pepsin solubilized collagen was introduced at the machine chest, the pH set point was lowered to 6.0, followed by a lowering to 5.0. The pepsin solubilized collagen flow was cut off. The machine was stabilized with no additives. APC's polymer additive was pumped back into the system. The mixed furnish was cut off, and the pH set point was raised back to 7 at the end of trial.

lar effects occurred on the system as the last trial. (Example 8B) The stock flow increased about 15% when the pepsin solubilized collagen was added. The pH changes (as described above) can be observed. The set point was lowered to 6.0 at 12:45, and it took about one half of an hour to reach a pH of 6.1. At 1:15, the pH set point was lowered to 5.0, and it took another half of an hour to reach that point. Once the set point was increased back to 7.0, the system pH rose quickly. There appeared to be a lowering of the main steam when the system was at a low pH. Between 1:15 and 1:45, the main steam averaged 5.1. The main steam was primarily between 7 and 9 when APC's polymer was used, or when there were no additives used. Lowering of the steam usage could be a significant savings.

Table 16B displays the wet end analysis for this trial. The pH curve of the whitewater was nearly identical in shape to the thick stock pH, except that the range was much greater. The thick stock pH followed the set point changes, whereas the whitewater pH started out higher at 7.7 and went down to 3.6 by 1:45. The relationship between the two pH measurements was similar to the last trial. The cationic demand of the headbox stock appeared to follow the whitewater pH curve. It began at 7.6, and dropped to 3.0 by 1:45. The cationic demand seems to be affected both by the pH and the polymers' interactions with the stock.

The first pass retention results were similar to the last trial. There was still some significant inconsistency in the results. Retentions for the samples containing pepsin solubilized collagen were mostly above 80%, with one result as low as 66.6%. This was most likely an operator error during analysis. Unlike the previous trials, the BOD results were not lowered at the time of pepsin solubilized collagen addition. All samples averaged around 700 mg/l. Once again, cold pepsin solubilized collagen brought the temperature of the whitewater down from 35.5° to 30.5° C.

TABLE 15B

Trial 5 Measurex Data from Paper Machine

| Roll | Reel Basis Wt. | Stock Flow | Thick Stock pH | Pepsin Solubilized Collagen Flow | Thick Stock Consistency | Machine Speed | Main Steam |
|---|---|---|---|---|---|---|---|
| 11:15 AM | 31.4 | 595.5 | 7.2 | 0.0 | 2.60 | 836.9 | 9.0 |
| 11:30 | 31.6 | 592.5 | 7.3 | 0.0 | 2.61 | 837.2 | 7.6 |
| 11:45 | 31.1 | 589.9 | 7.2 | 0.0 | 2.60 | 837.8 | 6.4 |
| 12:00 PM | 30.8 | 595.7 | 7.0 | 110.7 | 2.57 | 840.3 | 6.1 |
| 12:15 | 30.6 | 608.3 | 6.9 | 100.2 | 2.57 | 839.8 | 6.3 |
| 12:30 | 30.6 | 615.3 | 6.9 | 113.9 | 2.40 | 839.8 | 7.8 |
| 12:45 | 30.9 | 619.8 | 6.9 | 110.3 | 2.48 | 839.3 | 6.3 |
| 1:00 | 29.1 | 642.8 | 6.3 | 118.7 | 2.42 | 840.4 | 5.2 |
| 1:15 | 30.5 | 665.8 | 6.1 | 111.1 | 2.38 | 840.4 | 4.4 |
| 1:30 | 31.4 | 674.9 | 5.4 | 106.4 | 2.38 | 840.6 | 4.9 |
| 1:35 | 30.6 | 683.4 | 5.2 | 95.7 | 2.35 | 839.0 | 4.8 |
| 1:45 | 32.4 | 684.4 | 5.0 | 104.9 | 2.34 | 840.0 | 6.4 |
| 2:00 | 33.4 | 643.7 | 6.1 | 0.0 | 2.54 | 841.1 | 8.3 |
| 2:15 | 33.5 | 613.0 | 6.9 | 0.0 | 2.57 | 840.1 | 8.7 |
| 2:30 | 31.7 | 607.1 | 6.9 | 0.0 | 2.54 | 836.3 | 6.5 |
| 2:45 | 32.2 | 591.5 | 7.1 | 0.0 | 2.63 | 839.2 | 7.1 |

There was better control over the system during this trial. Table 15B summarizes selected machine parameters. Simi-

TABLE 16B

Trial 5 Wet End Summary

| Roll | Whitewater Temperature (C.) | Whitewater pH | Headbox consistency (mg/l) | Whitewater Consistency (mgl) | First Pass Retention (%) | Whitewater BOD (mg/l) | Cationic Demand |
|---|---|---|---|---|---|---|---|
| 11:15 AM | 35.6 | 7.7 | 3517 | 684 | 80.6 | 696 | 7.6 |
| 11:30 | 35.3 | 7.7 | 3892 | 939 | 75.9 | 785 | 7.6 |
| 11:45 | 35.4 | 7.7 | 3882 | 904 | 76.7 | 696 | 7.8 |
| 12:00 PM | 35.0 | 7.5 | 3815 | 912 | 76.1 | 703 | 7.0 |
| 12:15 | 35.0 | 7.0 | 3853 | 651 | 83.1 | 704 | 6.9 |
| 12:30 | 35.0 | 7.0 | 3934 | 1315 | 66.6 | 614 | 6.2 |
| 12:45 | 32.1 | 7.5 | 3632 | 698 | 80.8 | 757 | 6.0 |
| 1:00 | 31.8 | 6.8 | 3225 | 651 | 79.8 | 688 | 5.8 |
| 1:15 | 31.4 | 6.0 | 4307 | 630 | 85.4 | 698 | 4.8 |
| 1:30 | 31.0 | 4.5 | 3456 | 679 | 80.4 | 693 | 4.2 |
| 1:35 | 30.4 | 3.9 | 4241 | 784 | 81.5 | 710 | 3.4 |
| 1:45 | 30.6 | 3.6 | 4586 | 1068 | 76.7 | 744 | 3.0 |
| 2:00 | 31.8 | 5.0 | 3915 | 1243 | 68.3 | 646 | 5.0 |
| 2:15 | 32.4 | 6.8 | 3889 | 752 | 80.7 | N/A | 6.6 |
| 2:30 | 33.0 | 6.9 | 4059 | 977 | 75.9 | N/A | 6.8 |
| 2:45 | 33.6 | 7.1 | 3913 | 1198 | 69.4 | N/A | 7.1 |

A summary of the results on the paper can be seen in Table 17B. The 11:15 sample was at a pH of 7.0 with APC's polymer. The next two samples contained no additives. The 12:00 through 12:45 samples contained pepsin solubilized collagen at a pH of 7.0. The 1:00 and 1:15 samples had a pH set point at 6.0, and the 1:30 and 1:45 samples had a set point of 5.0. The 2:00 and 2:15 samples contained no additives at a variable pH. The last two samples contained APC's polymer, and the pH was nearing 7.0.

The tensile results were encouraging. The 1:00 and 1:15 samples, which had a pH of about 6 and contained pepsin solubilized collagen, yielded the highest machine direction tensile indices, by 3 to 7%, as compared to the samples with APC's polymer additive. Although this is only a slight increase, it was important to find an optimal pH at which to run the system. The TEA measurements were highest at the low pH set point of 5.0, but still showed increases of a few percent at a pH of 6.0.

TABLE 17B

Trial 5 Test Results Summary

| Sample | Basis Weight | Caliper | Tear Index MD | Tear Index CD | Tensile Index MD | Tensile Index CD | TEA MC | TEA CD | Burst Index | Porosity |
|---|---|---|---|---|---|---|---|---|---|---|
| 11:15 AM | 31.7 | 3.6 | 64 | 82 | 73.1 | 33.2 | 3.35 | 2.84 | 3.08 | 30 |
| 11:30 | 3.20 | 3.5 | 67 | 89 | 76.9 | 32.6 | 3.47 | 2.92 | 2.91 | 37 |
| 11:45 | 3.17 | 3.6 | 60 | 75 | 74.2 | 30.6 | 3.33 | 2.71 | 2.82 | 37 |
| 12:00 PM | 30.9 | 3.6 | 66 | 85 | 74.3 | 30.0 | 3.28 | 2.70 | 2.83 | 30 |
| 12:15 | 31.1 | 3.6 | 67 | 85 | 72.9 | 31.5 | 3.29 | 2.76 | 2.81 | 33 |
| 12:30 | 31.5 | 3.6 | 73 | 89 | 75.7 | 31.2 | 3.45 | 2.86 | 2.85 | 45 |
| 12:45 | 31.3 | 3.6 | 63 | 76 | 73.0 | 32.5 | 3.31 | 2.50 | 2.82 | 43 |
| 1:00 | 29.4 | 3.5 | 79 | 89 | 79.7 | 32.3 | 3.47 | 2.29 | 2.84 | 23 |
| 1:15 | 30.4 | 3.5 | 75 | 93 | 77.5 | 32.3 | 3.60 | 2.63 | 2.82 | 20 |
| 1:30 | 30.5 | 3.6 | 70 | 83 | 74.5 | 32.6 | 3.40 | 2.58 | 2.80 | 18 |
| 1:45 | 30.1 | 3.5 | 65 | 81 | 78.8 | 32.9 | 3.81 | 2.54 | 2.83 | 21 |
| 2:00 | 33.8 | 3.8 | 82 | 95 | 72.9 | 32.3 | 3.26 | 2.62 | 2.61 | 22 |
| 2:15 | 33.7 | 3.7 | 66 | 84 | 73.6 | 31.6 | 3.19 | 2.37 | 2.68 | 34 |
| 2:30 | 31.8 | 3.6 | 72 | 89 | 76.0 | 31.5 | 3.61 | 2.23 | 2.66 | 32 |
| 2:45 | 32.2 | 3.7 | 75 | 90 | 75.3 | 32.7 | 3.46 | 2.69 | 2.7 | 29 |

All physical testing was the same as Trials 3 and 4 (Examples 7B and 8B), except the tensile testing was done on a new tester from Thwing-Albert Instrument Co. This instrument measured elongation and tensile energy absorption (TEA) of the samples, in addition to measuring the load at break. TEA, the total energy required to break the sample, is a calculation of the area under the elongation/load curve.

The overall quality of all the samples was nearly as good as typical 100% OCC paper. The deinked news print appeared to have properties equal to the news blank that was used in previous trials. It was learned that the deinking process rids the pulp of many fines and only longer and stronger fibers are left. From this, it was determined that the use of eucalyptus fibers should be investigated in future trials.

The porosity results of the low pH samples (1:00 through 1:45) were significantly lower than for the pepsin solubilized collagen samples at neutral pH, indicating that the paper was more porous. The porosity results went from 30 sec/100 ml with APC's polymer additive, up to 38 sec/100 ml during the pepsin solubilized collagen addition at pH 7.0, down to 20 sec/100 ml at a pH of 5.0. This behavior was much like that in Trial 4 (Example 8B), when the porosity dropped from 24 sec/100 ml with APC's polymer down to 11–16 sec/100 ml with the pepsin solubilized collagen. No other significant changes were observed with any of the other properties.

The following conclusions were made from Trial 5. The deinked news print was as good as the news blank used in previous trials in terms of the tensile strength of the resultant paper. Adding 40% deinked news into the furnish did not significantly decrease the strength of the finished paper. Machine direction tensile index increased slightly (3 to 7%) with the addition of pepsin solubilized collagen. Indicatinga more porous paper than with the normal APC polymers, the porosity results decreased at low pH's with the addition of pepsin solubilized collagen. First pass retention with pepsin solubilized colladen was as good as with APC's polymer. The cationic demand curve mimicked the pH curve. BOD results were unaffected by the pH change or the addition of pepsin solubilized collagen.

These were the most consistent results of any of the previous trials. Even so, not enough data points were taken under stable conditions to assure consistency. Samples were taken every fifteen minutes from the start of the trial to the end. Most of the samples were taken during the transition periods and were not necessary. At most, there were only two points for each stable condition. Five data points for each condition was deemed desirable.

Example 10B

The objectives of this trial were to study the effect of adding the pepsin solubilized collagen at the machine chest and at the center screen; to hold the pH of the stock as constant as possible at pH 6.0; and to increase the number of samples taken at each period of stability.

Based on Trial 5 (Example 9B), a pH of 6.0 was chosen to be the optimal pH at which to run. Maintaining a constant pH throughout the trial allowed for more consistent results. As with Trial 5, the furnish consisted of 60% OCC and 40% deinked newsprint (ONP). The two addition points chosen were the machine chest, where the pepsin solubilized collagen had been added before, and the center screen, just before the headbox where APC pumps in their polymer. Pumping the pepsin solubilized collagen into the machine chest provided about ten to fifteen minutes of mixing time with the stock, while putting it in just before the headbox, gave only a few seconds of mixing time before it reached the forming wire.

Standard 30 lb. basis weight paper was produced at about 847 fpm. Sixty-three hundred (6300) gallons of pepsin solubilized collagen were produced from 675 lbs. of limed splits ground at the USDA. The pepsin solubilized collagen was made under cold conditions and developed a viscosity that was lower than desired. It was produced in a 9000 gal. mixing tank. From there, it was pumped into a 3000 gal. tank with dilution water. It was pumped from the dilution tank to the center screen for the first half of the pepsin solubilized collagen addition and to the machine chest for the second half.

The following is a description of the trial. The machine was stabilized with 60/40 furnish and APC's polymer additive, at pH 6.0. Samples were taken with APC's polymer. APC's polymer additive was turned off. Pepsin solubilized collagen flow was started to the center screen by slowly increasing flow rate. Pepsin solubilized collagen flow was maximized at the center screen at 85 gpm. Pepsin solubilized collagen flow was then diverted from the center screen to the machine chest (flow reached 128 gpm). Pepsin solubilized collagen flow was cut off. APC's polymer additive was turned back on.

There was better control over the APC system than in all previous trials. Table 18B shows how the machine parameters changed throughout the trial. The variance of the stock pH was a concern, but it varied only 0.6 of a pH unit from 6.4 to 5.8. The flow of the pepsin solubilized collagen was stepped up to about 85 gpm when it was added to the center screen. This was the maximum flow rate obtainable with the centrifugal pump used. A greater flow was achieved when pumping to the machine chest.

TABLE 18B

| | Trial 6 Measurex Data from Paper Machine | | | | | | |
|---|---|---|---|---|---|---|---|
| Sample | Reef Basis Wt. | Stock Flow | Thick Stock Consistency | Thick Stock pH | Pepsin Solubilized Collagen Flow | Machine Speed | Main Steam |
| 8:18 AM | 31.2 | 576.6 | 2.6 | 6.3 | 0.0 | 846.6 | 7.3 |
| 8:21 | 31.4 | 574.5 | 2.6 | 6.3 | 0.0 | 847.0 | 6.7 |
| 8:29 | 31.3 | 574.9 | 2.6 | 6.1 | 0.0 | 846.3 | 7.7 |
| 8:40 | 31.3 | 581.0 | 2.6 | 6.4 | 0.0 | 847.0 | 7.5 |
| 8:50 | 31.0 | 585.7 | 2.6 | 6.4 | 0.0 | 847.1 | 7.5 |
| 9:00 | 31.0 | 587.2 | 2.6 | 6.4 | 0.0 | 846.7 | 7.6 |
| 9:15 | 31.8 | 589.2 | 2.6 | 6.4 | 0.0 | 846.8 | 7.1 |
| 9:30 | 31.4 | 586.0 | 2.6 | 6.3 | 0.0 | 847.1 | 6.8 |
| 9:38 | 31.8 | 581.1 | 2.6 | 6.2 | 27.8 | 847.3 | 8.0 |
| 9:55 | 31.0 | 586.9 | 2.6 | 6.1 | 70.2 | 846.5 | 7.2 |
| 10:09 | 31.1 | 587.9 | 2.6 | 5.9 | 88.9 | 846.3 | 7.3 |
| 10:25 | 31.8 | 588.8 | 2.6 | 5.9 | 83.8 | 846.7 | 6.7 |
| 10:35 | 31.5 | 591.0 | 2.6 | 5.8 | 84.1 | 846.9 | 6.9 |
| 10:45 | 32.2 | 593.9 | 2.6 | 5.9 | 84.8 | 846.9 | 7.4 |
| 10:50 | 31.7 | 596.2 | 2.6 | 5.9 | 116.0 | 847.1 | 7.1 |
| 11:00 | 30.7 | 597.6 | 2.6 | 5.9 | 127.9 | 847.1 | 7.3 |
| 11:15 | 29.8 | 608.6 | 2.5 | 6.0 | 127.8 | 846.9 | 7.0 |
| 11:25 | 30.0 | 618.8 | 2.5 | 6.1 | 128.1 | 846.7 | 6.7 |
| 11:32 | 31.4 | 622.4 | 2.5 | 6.3 | 128.2 | 846.6 | 6.9 |
| 11:40 | 30.6 | 627.0 | 2.5 | 6.4 | 128.5 | 846.3 | 6.9 |
| 11:50 | 31.4 | 626.4 | 2.5 | 6.6 | 130.3 | 846.9 | 6.7 |

Because of the flow rate discrepancy, it was difficult to directly compare the two points. Much like Trial 5 (Example 9B), the main steam was not affected by the pepsin solubilized collagen. The stock flow showed less of an increase in flow than previous trials. The flow increased less than 10% even during the highest pepsin solubilized collagen flow rates.

Wet end samples were taken every five minutes during periods of stability on the machine. Five samples were taken for each condition on the machine. There were no samples representing the transition periods. Table 19B is divided into the three sampling conditions. The first five samples contained APC's polymer. The middle five contained pepsin solubilized collagen that was added at the center screen. The last five were taken when the pepsin solubilized collagen was added to the machine chest.

TABLE 19B

Trial 6 Wet End Summary

| Sample | Whitewater Temperature (C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 8:40 AM | 30.6 | 6.99 | 3536 | 396 | 88.8 | 840 | 5.0 |
| 8:45 | 30.6 | 6.99 | 3504 | 420 | 88.0 | 662 | 5.9 |
| 8:50 | 30.6 | 6.99 | 3468 | 458 | 86.8 | 675 | 5.4 |
| 8:55 | 30.6 | 6.99 | 3452 | 448 | 87.0 | 669 | 5.4 |
| 9:00 | 30.6 | 6.99 | 3526 | 650 | 81.6 | 647 | 5.5 |
| 10:25 | 28.5 | 6.20 | 3746 | 648 | 82.7 | 540 | 5.8 |
| 10:30 | 28.5 | 6.21 | 3742 | 606 | 83.8 | 605 | 5.5 |
| 10:35 | 28.4 | 6.22 | 4150 | 812 | 80.4 | 564 | 5.7 |
| 10:40 | 28.3 | 6.22 | 4110 | 624 | 84.8 | 551 | 5.7 |
| 10:45 | 28.3 | 6.23 | 3982 | 616 | 84.5 | 713 | 5.6 |
| 11:25 | 27.5 | 6.92 | 3376 | 650 | 80.7 | 558 | 5.6 |
| 11:35 | 27.5 | 7.02 | 3502 | 530 | 84.9 | 438 | 5.4 |
| 11:40 | 27.5 | 7.07 | 3490 | 522 | 85.0 | 290 | 5.2 |
| 11:45 | 27.5 | 7.12 | 3542 | 538 | 84.8 | 713 | 5.0 |
| 11:48 | 27.5 | 7.15 | 3444 | 604 | 82.5 | 447 | 5.3 |

The whitewater pH, more sensitive than the thick stock pH, varied up to 0.9 pH units. This was better pH control than had been previously accomplished. The whitewater temperature dropped about 3° C. when the pepsin solubilized collagen was added. The first pass retention results were by far the most consistent. There were no questionable low or high points. All samples had retentions between 80.4 and 88.8%. pepsin solubilized collagen appeared to have comparable retentions to APC's polymer (86 to 83%). The BOD of both pepsin solubilized collagen points was considerably lower than the samples with APC's polymer. APC's polymer gave BOD's of 700 mg/l, while the center screen samples averaged 595 mg/l and the machine chest samples averaged 490 mg/l. This was a significant decrease, and could prove to be a great advantage in using pepsin solubilized collagen. The cationic demand showed no great effects at any point and it did not follow the pH, as with Trial 5. This proves that within a small pH range, cationic demand is more affected by the additives to the system.

The physical testing was done, and the results can be seen in Table 20B. A and B samples were taken off the machine, not put into rolls as before. The samples were taken at ten minute intervals off the winder and folded so that they could be immediately tested. Samples were taken only during stable periods on the paper machine.

TABLE 20B

Trial 6 Sample Test Results

| Sample | | Basis Weight | Cal- iper | Tear MD | Tear CD | Tensile MD | Tensile CD | Burst | Por- osity |
|---|---|---|---|---|---|---|---|---|---|
| 1 | A | 31.4 | 3.6 | 40.4 | 47.8 | 16.7 | 7.5 | 17.6 | 18.1 |
| 8:40 AM | B | 31.4 | 3.5 | 36.9 | 44.6 | 19.6 | 8.2 | 19.3 | 24.3 |
| 2 | A | 31.8 | 3.9 | 40.6 | 48.5 | 17.6 | 7.2 | 19.7 | 18.0 |
| 8:50 | B | 31.9 | 3.6 | 39.1 | 48.6 | 18.4 | 8.0 | 19.5 | 18.6 |
| 3 | A | 32.4 | 3.8 | 41.5 | 50.8 | 17.0 | 7.4 | 19.9 | 16.2 |
| 9:00 | B | 32.5 | 3.7 | 40.0 | 47.9 | 18.9 | 7.5 | 20.8 | 17.0 |
| 4 | A | 32.2 | 3.6 | 41.5 | 49.0 | 19.0 | 7.7 | 20.7 | 27.4 |

TABLE 20B-continued

Trial 6 Sample Test Results

| Sample | | Basis Weight | Cal- iper | Tear MD | Tear CD | Tensile MD | Tensile CD | Burst | Por- osity |
|---|---|---|---|---|---|---|---|---|---|
| 10:25 | B | 32.0 | 3.5 | 39.4 | 47.5 | 20.7 | 8.7 | 23.2 | 24.5 |
| 5 | A | 32.1 | 3.8 | 41.0 | 45.7 | 18.5 | 8.2 | 20.5 | 25.8 |
| 10:35 | B | 31.2 | 3.4 | 39.3 | 48.9 | 20.6 | 8.6 | 21.9 | 22.5 |
| 6 | A | 31.6 | 3.6 | 41.0 | 52.3 | 20.4 | 7.8 | 22.2 | 23.3 |
| 10:45 | B | 31.3 | 3.6 | 37.0 | 46.1 | 19.9 | 8.4 | 23.2 | 27.6 |
| 7 | A | 31.5 | 3.6 | 35.4 | 45.0 | 20.8 | 7.9 | 21.4 | 32.2 |
| 11:25 | B | 30.5 | 3.4 | 34.6 | 43.1 | 20.4 | 8.3 | 22.8 | 29.1 |
| 8 | A | 31.6 | 3.6 | 41.3 | 46.5 | 21.3 | 8.1 | 22.7 | 19.7 |
| 11:40 | B | 30.7 | 3.4 | 33.6 | 44.5 | 18.7 | 8.3 | 21.4 | 22.7 |

Taking multiple samples under each condition allowed for greater reliability and confidence. Samples 1, 2 and 3 contained APC's polymer additive. Samples 4,5 and 6 had pepsin solubilized collagen added to the center screen. There were only two samples taken from the last set because of a sheet break on the paper machine. Each set covered a 15 to 20 minute span when the machine was stabilized. There were no significant changes in any paper properties between samples 1 and 3, 4 and 6 or 7 and 8.

Table 21B summarizes the three sets of data. The basis weights and calipers remained relatively constant and within specifications. Both the pepsin solubilized collagen sets showed increases in machine direction tensile strengths. Adding the pepsin solubilized collagen at the center screen produced a 10.6% increase and adding the pepsin solubilized collagen at the machine chest produced a 15.5% increase. Even the cross direction tensile strengths increased 8 to 9%. Burst results showed similar increases. The machine chest samples had slightly lower tears, but they were all within the specification limits. Porosity increased by 30 to 35% with the pepsin solubilized collagen samples.

TABLE 21B

Trial 6 Test Results Summary

| Sample | Description | Basis Weight | Caliper | Tear Index MD | Tear Index CD | Tensile Index MD | Tensile Index CD | Burst Index | Porosity |
|---|---|---|---|---|---|---|---|---|---|
| 1, 2, 3 | 60/40, w/APC's polymer | 31.9 | 3.7 | 77 | 93 | 62.5 | 26.4 | 2.58 | 19 |
| 4, 5, 6 | 60/40, pepsin solubilized collagen @ c. screen | 31.7 | 3.6 | 77 | 93 | 69.1 | 28.6 | 2.93 | 25 |
| 7, 8 | 60/40, pepsin solubilized collagen @ m. chest | 31.1 | 3.5 | 72 | 89 | 72.2 | 28.9 | 3.01 | 26 |

It could not be determined which addition point was "better". Since there were different flow rates at each point of addition, a further study was contemplated. Machine direction tensile strength throughout the trial was composed to the pepsin solubilized collagen flow rate. The tensile strength appeared to increase as the flow increased. These were the first significant increases in tensile strength of any of the trials, indicating success at converting a small scale operation into a large scale one.

The following conclusions were drawn from Trial 6: pepsin solubilized collagen added at the center screen increased machine direction tensile strength by 10.6%. Pepsin solubilized collagen added at the machine chest increased machine direction tensile strength by 15.5%. Adding pepsin solubilized collagen increased porosity results by over 30% The same flow rate could not be achieved by pumping to the center screen as compared to the machine chest. First pass retention with pepsin solubilized collagen was as good as with APC's polymer. Cationic demand was unaffected during the pepsin solubilized collagen addition. BOD results decreased 100 to 200 mg/l when pepsin solubilized collagen was used. The deinked newsprint continued to be as good a source of quality fiber as the OCC. pH control was better than any of the trials.

Fewer problems occurred. The main difficulty was in comparing the two pepsin solubilized collagen addition points, since the pepsin solubilized collagen was delivered at different flow rates to the two sites. Another problem was the number of sheet breaks during the pepsin solubilized collagen addition. It was not known what was the cause of the breaks, since this had not been a problem before.

For Examples 5B to 10B, the pepsin solubilized collagen was prepared in the same way. A minimum of 24 hours was given to produce each pepsin solubilized collagen batch. For Trial 1, the limed splits were purchased from Teepak. The remaining trials used pepsin solubilized collagenmade from limed splits bought at Seton Company and ground at the USDA.

Example 11B

The objectives of this trial were to reproduce the tensile strength increases of Trial 6; to determine the optimal flow rate and location of the pepsin solubilized collagen addition; and to use a 50% ONP/50% OCC furnish (the ONP contained ~25% OCC).

Trial 6 showed significant increases in machine direction tensile strength. It was necessary to attempt to duplicate these results by runninga nearly identical experiment. The only variation in this experiment was an added low flow to the center screen. A slightly higher percentage of ONP was used, but was believed to have had a negligible effect on the system.

Standard 30 lb. basis weight paper was produced at about 850 fpm. Sixty-five hundred (6500) gallons of pepsin solubilized collagen were produced from 725 lbs of limed splits ground at the USDA. It was produced in a 9000 gal. mixing tank. From there, it was pumped into a 3000 gal. tank with dilution water. At this point, it was pumped to the center screen towards the beginning of the trial and later diverted to the machine chest.

The following is a description of the trial. The machine was stabilized at 50/50 furnish and at 6.0 pH, with APC's polymer additive. The first set of controls was taken, then APC's polymer additive was cut off. Pepsin solubilized collagen flow was started to the center screen at 50 gpm. Sample set #2 was taken. Pepsin solubilized collagen flow was increased to 99 gpm at the center screen. Sample set #3 was taken, then pepsin solubilized collagen flow was increased to the machine chest at 134 gpm. Sample set #4 was taken, then pepsin solubilized collagen flow was cut off. APC's polymer additive was pumped back into system. Sample set #5 was taken, asthe second set of controls.

Much like Trial 6, there was good control over the system. One improvement of this trial was that a set of controls was taken at the end of the trial as well as at the beginning. Sufficient time was allowed to stabilize the paper machine after the pepsin solubilized collagen addition was shut off and transitioned with APC's polymer additive.

Table 22B summarizes the machine parameters as they varied throughout the trial. During sampling times, the thick stock pH held consistently between 5.7 and 6.3. This is as good a pH control as can be expected at APC. The main steam appeared to decrease significantly, from 9–11 down to 8–9. This drop in main steam could result in a faster machine speed and an increased production rate for APC.

TABLE 22B

Trial 7 Measurex Data from Paper Machine

| Sample | Reel Basis Wt. | Stock Flow | Thick Stock Consistency | Thick Stock pH | Pepsin Solubilized Collagen Flow | Machine Speed | Main Steam |
|---|---|---|---|---|---|---|---|
| 8:00 AM | 32.1 | 605.5 | 2.60 | 5.9 | 0.0 | 850.1 | 10.6 |
| 8:10 | 31.6 | 597.8 | 2.60 | 6.1 | 0.0 | 850.1 | 11.6 |
| 8:19 | 30.3 | 605.1 | 2.59 | 6.2 | 0.0 | 850.0 | 9.2 |
| 9:04 | 30.9 | 612.4 | 2.59 | 5.9 | 51.4 | 850.2 | 9.4 |
| 9:19 | 30.7 | 614.9 | 2.60 | 6.0 | 49.2 | 850.1 | 7.8 |
| 9:40 | 31.4 | 618.6 | 2.59 | 6.0 | 51.9 | 849.9 | 8.6 |
| 9:51 | 30.1 | 618.7 | 2.61 | 6.0 | 51.4 | 850.1 | 8.0 |
| 10:01 | 32.3 | 618.0 | 2.59 | 6.1 | 49.0 | 849.6 | 8.5 |
| 10:21 | 31.6 | 616.7 | 2.61 | 6.1 | 98.9 | 849.9 | 8.9 |
| 10:27 | 31.5 | 617.7 | 2.60 | 6.0 | 98.8 | 849.8 | 9.5 |
| 10:39 | 30.4 | 624.7 | 2.59 | 6.0 | 99.1 | 849.7 | 8.0 |
| 11:00 | 32.3 | 629.6 | 2.58 | 5.9 | 98.3 | 850.1 | 9.3 |
| 11:02 | 31.3 | 626.2 | 2.55 | 5.9 | 135.6 | 850.4 | 9.0 |
| 11:10 | 31.9 | 628.0 | 2.56 | 5.7 | 133.9 | 850.4 | 9.0 |
| 11:44 | 31.2 | 671.3 | 2.45 | 5.6 | 133.9 | 850.1 | 8.4 |
| 11:50 | 30.9 | 668.7 | 2.41 | 5.7 | 132.0 | 850.1 | 8.9 |
| 11:54 | 31.0 | 671.2 | 2.48 | 5.7 | 130.7 | 850.0 | 8.3 |
| 11:58 | 30.6 | 668.8 | 2.48 | 5.8 | 125.7 | 850.2 | 8.5 |
| 12:01 PM | 30.8 | 670.9 | 2.46 | 5.8 | 125.5 | 850.2 | 9.0 |
| 12:04 | 31.1 | 672.1 | 2.46 | 5.9 | 123.9 | 849.7 | 8.2 |
| 12:10 | 31.4 | 670.2 | 2.49 | 6.0 | 0.0 | 849.8 | 8.9 |
| 12:15 | 34.2 | 646.9 | 2.56 | 6.2 | 118.0 | 850.2 | 11.5 |
| 12:24 | 33.3 | 628.0 | 2.62 | 6.5 | 0.0 | 849.9 | 11.2 |
| 12:29 | 32.9 | 621.7 | 2.59 | 6.5 | 116.8 | 849.7 | 11.0 |
| 12:29 | 32.7 | 617.5 | 2.59 | 6.5 | 0.0 | 849.9 | 11.4 |
| 1:10 | 29.4 | 592.6 | 2.60 | 5.8 | 0.0 | 850.0 | 9.2 |
| 1:25 | 31.4 | 598.1 | 2.59 | 5.9 | 0.0 | 849.6 | 8.2 |
| 1:36 | 30.7 | 601.5 | 2.60 | 6.3 | 0.0 | 850.1 | 9.1 |

Wet end samples were taken every five minutes during the above sampling times. The wet end test results, summarized in Table 23B, exhibited similar characteristics to previous trials. The temperature of the whitewater decreased about 2° C. when the pepsin solubilized collagen was added. First pass retention results were very consistent throughout the trial, generally ranging from 85 to 89%. The highest retentions were found during the pepsin solubilized collagen addition of 99 gpm to the center screen. Pumping the pepsin solubilized collagen to the center screen at lower flows appears to have equivalent effects as higher flow rates to the machine chest. The interactions between the wood fibers and the pepsin solubilized collagen were greatest when the pepsin solubilized collagen was added at 99 gpm to the center screen. This is reflected in the low cationic demand results. The 50 gpm samples had the least effect on the system. BOD results held constant throughout the trial, ranging from 576 to 607.

TABLE 23B

Trial 7 Wet End Summary

| Sample | Whitewater Temperature (°C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 8:00 AM | 34.9 | 6.49 | 3676 | 477 | 87.0 | 588 | 6.4 |
| 8:05 | 34.9 | 6.64 | 3720 | 468 | 87.4 | — | — |
| 8:10 | 34.9 | 6.76 | 3634 | 469 | 87.1 | 596 | 6.3 |
| 8:15 | 34.9 | 6.85 | 3661 | 479 | 86.9 | — | — |
| 8:20 | 34.9 | 6.88 | 3493 | 503 | 85.6 | 599 | — |
| 9:40 | 34.7 | 6.20 | 3192 | 447 | 86.0 | 602 | 6.8 |
| 9:45 | 34.7 | 6.11 | 3351 | 445 | 86.7 | — | — |
| 9:50 | 34.7 | 6.22 | 3370 | 488 | 85.5 | 602 | — |
| 9:55 | 34.7 | 6.31 | 3591 | 548 | 84.7 | — | — |
| 10:00 | 34.7 | 6.31 | 2763 | 523 | 81.1 | 605 | 7.0 |
| 10:40 | 33.2 | 5.87 | 2740 | 343 | 87.5 | 602 | 5.4 |
| 10:45 | 33.2 | 5.77 | 3010 | 348 | 88.4 | — | — |
| 10:50 | 33.2 | 5.82 | 3116 | 319 | 89.8 | 596 | — |
| 10:55 | 33.2 | 5.85 | 2972 | 338 | 88.6 | — | — |
| 11:00 | 33.2 | 5.79 | 3414 | 310 | 90.9 | 576 | 5.0 |
| 11:35 | 33.0 | 6.47 | 3697 | 496 | 86.6 | 607 | 6.2 |
| 11:40 | 33.0 | 6.36 | 3569 | 456 | 87.2 | — | — |
| 11:45 | 33.0 | 6.49 | 3710 | 507 | 86.3 | 607 | — |

TABLE 23B-continued

Trial 7 Wet End Summary

| Sample | Whitewater Temperature (°C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 11:50 | 33.0 | 6.57 | 3492 | 518 | 85.2 | — | — |
| 11:55 | 33.0 | 6.65 | 3595 | 505 | 86.0 | 603 | 6.0 |
| 1:10 PM | 34.6 | 6.60 | 3430 | 374 | 89.1 | 596 | 5.5 |
| 1:15 | 34.6 | 6.44 | 3344 | 401 | 88.0 | — | — |
| 1:25 | 34.6 | 6.62 | 3494 | 381 | 89.1 | 605 | — |
| 1:30 | 34.6 | 6.69 | 3128 | 398 | 87.3 | — | — |
| 1:35 | 34.6 | 6.77 | 3358 | 413 | 87.7 | 606 | 5.0 |

The results of the physical testing performed at Ranpak are summarized in Table 24B. As with Trial 6, "A" and "B" samples were tested to give a good estimation of the average sheet strength across the paper machine. Three samples for each set were taken at ten minute intervals (during sampling times) off the winder. The controls were represented by the first and fifth sets of data. There was only a 1 to 2% difference in machine direction tensile index and cross direction tear index, and <1% difference in burst index between the controls, suggesting that the system returned to "normal" after the pepsin solubilized collagen addition and that the test results were reliable.

The following conclusions were reached: Machine direction tensile index increased 6.0% with pepsin solubilized collagen at a low flow to the center screen; 7.2% with pepsin solubilized collagen at a medium flow to the center screen; and 8.0% with pepsin solubilized collagen at a high flow to the machine chest. MD tensile index increases only occurred when pepsin solubilized collagen was added. The lowest tensile results occurred with the controls (at the start and at the end of the trial). Cross direction tensile index increased about 8 to 10% when pepsin solubilized collagen was added. Burst index increased 7 to 10% when pepsin solubilized collagen was added. First pass retention was consistent

TABLE 24B

Test Results Summary

| Property | Control: APC polymer beginning of trial | pepsin solubilized collagen: 50 gpm @ center screen | pepsin solubilized collagen: 99 gpm @ center screen | pepsin solubilized collagen: 134 gpm @ machine chest | Control: APC polymer end of trial |
|---|---|---|---|---|---|
| Basis Weight | 31.6 | 30.8 | 31.3 | 31.0 | 30.7 |
| Caliper | 3.4 | 3.3 | 3.4 | 3.3 | 3.4 |
| MD Tear Index | 64 | 69 | 69 | 64 | 68 |
| CD Tear Index | 78 | 80 | 81 | 79 | 79 |
| MD Tensile Index | 75.4 | 79.4 | 80.3 | 80.9 | 74.4 |
| CD Tensile Index | 33.3 | 35.0 | 34.5 | 35.2 | 30.6 |
| Burst Index | 2.92 | 3.13 | 3.20 | 3.11 | 2.91 |
| Porosity | 35 | 26 | 24 | 37 | 21 |
| F. P. Retention | 86.8 | 84.8 | 89.0 | 86.3 | 88.2 |
| BOD | 594 | 603 | 591 | 606 | 602 |
| Cationic Demand | 6.35 | 6.90 | 5.20 | 6.10 | 5.25 |

All three samples containing pepsin solubilized collagen showed modest increases in machine direction tensile index, ranging from 6 to 8%. Cross direction tensile index increased from 8 to 10%, which was comparable to Trial 6. As the pepsin solubilized collagen flow rate increased from 50 to 134 gpm, there was essentially no change in machine or cross direction tensile strength.

The tear results were unaffected by the pepsin solubilized collagen addition, showing changes of −2.3 to +5.5%. Burst index had increases (7 to 10%) similar to that of tensile strength. The increase in machine direction tensile and burst was more pronounced in Trial 6, suggesting that there is a range of increases that could be expected from the addition of pepsin solubilized collagen. The porosity values for the controls varied from 21 to 35, so it was difficult to observe any changes due to the pepsin solubilized collagen addition. Based on the last two trials, it appeared that there was no loss in strength or first pass retention when a lower flow was used at the center screen, instead of a higher flow to the machine chest.

throughout for all samples, generally ranging from 85 to 89%. The BOD of the whitewater stream did not change when pepsin solubilized collagen was added. Cationic demand had the most significant decrease when the pepsin solubilized collagen was added to the center screen at a medium flow.

The pepsin solubilized collagen appeared to be of good quality. The reaction took place at 20° C. with no large particles present. The center screen appeared to be the better addition point than the machine chest because significantly lower flow rates could be used to produce the same tensile strength increases and first pass retentions.

Example 12B

The objectives of this trial were to run an entire trial with 100% ONP mixture (actual ~75% ONP/25% OCC); and to observe the effects of three different addition rates of pepsin solubilized colladen to the center screen.

It had been decided that the pepsin solubilized collagen would be added at the center screen. To help determine the optimal addition rate for pepsin solubilized collagen, three flow rates were used during the trial. In an effort to find a weaker fiber source, the ONP pulped at Putney Paper was chosen for 100% of the furnish.

Standard 30 lb. basis weight paper was produced at about 864 fpm. Sixty-eight hundred (6800) gallons of pepsin solubilized collagen were produced from 650 lbs. of limed splits ground at the USDA. It was produced in a 9000 gal. mixing tank. From there, it was pumped into a 3000 gal. tank with dilution water. At this point, it was pumped to the center screen towards the beginning of the trial and later diverted to the machine chest.

The following is a description of the trial. The machine was stabilized at 100% furnish, at 6.0 pH, with APC's polymer additive. Sample set #1 was taken as the first set of controls, then APC's polymer was cut off. Pepsin solubilized colladen flow was started to the center screen at 33 gpm. Sample set #2 was taken, then pepsin solubilized collagen flow was increased to 66 gpm. Sample set #3 was taken, then pepsin solubilized collagen flow was increased to 98 gpm. Sample set #4 was taken. The pepsin solubilized collagen tank ran out. APC's polymer was pumped back into system. Sample set #5 was taken as the second set of controls.

Trial 8 was similar in procedure to the Trials 6 and 7, so there was good control over the system. Because of the high percentage of ONP in the system, there was some trial and error as to what the machine parameters should be. Groundwood fiber pulps (ONP) have significantly different drainage and drying characteristics than chemical (OCC) pulps. As can be seen in Table 25B, the machine speed was still operated as fast or faster than previous trials, even though the ONP had poorer drainage properties. There was continued success in controlling the pH at around 6.0. The primary machine parameter that was affected was the main steam. When APC's polymer additive was used, the main steam ranged from about 10 to 11. This value decreased to 7 to 9 during the entire time pepsin solubilized collagen was added. The main steam usage was decreased consistently for most of the trials, suggesting that the paper machine could be run at a faster speed and result in a higher production rate.

TABLE 25B

Trial 8 Measurex Data from Paper Machine

| Sample | Reel Basis Wt. | Stock Flow | Thick Stock Consistency | Thick Stock pH | Pepsin Solubilized Collagen Flow | Machine Speed | Main Steam |
| --- | --- | --- | --- | --- | --- | --- | --- |
| 7:50 AM | 32.6 | 623.9 | 2.5 | 5.9 | 0.0 | 863.8 | 11.9 |
| 7:59 | 31.8 | 618.1 | 2.6 | 5.9 | 0.0 | 863.9 | 11.7 |
| 8.09 | 32.1 | 609.1 | 2.6 | 6.0 | 0.0 | 863.9 | 10.5 |
| 8:10 | 32.3 | 608.4 | 2.6 | 6.0 | 0.0 | 863.9 | 10.5 |
| 8:19 | 32.3 | 604.0 | 2.6 | 6.0 | 0.0 | 863.6 | 10.2 |
| 8:30 | 29.8 | 604.7 | 2.6 | 6.0 | 0.0 | 864.0 | 8.7 |
| 8:45 | 31.5 | 607.7 | 2.6 | 6.1 | 0.0 | 863.9 | 9.9 |
| 8:49 | 31.9 | 606.8 | 2.6 | 6.1 | 0.0 | 864.1 | 10.2 |
| 8:55 | 31.4 | 605.7 | 2.6 | 6.1 | 0.0 | 864.1 | 10.3 |
| 8:58 | 31.9 | 605.0 | 2.6 | 6.1 | 8.7 | 864.2 | 10.3 |
| 8:59 | 31.6 | 604.8 | 2.6 | 6.2 | 43.2 | 864.1 | 10.3 |
| 9:00 | 33.5 | 600.7 | 2.6 | 6.2 | 40.9 | 864.0 | 11.2 |
| 9:03 | 31.6 | 600.8 | 2.6 | 6.2 | 37.1 | 864.0 | 10.7 |
| 9:16 | 30.5 | 600.8 | 2.6 | 6.2 | 33.2 | 864.2 | 9.4 |
| 9:29 | 31.3 | 602.7 | 2.6 | 6.1 | 33.3 | 863.7 | 8.8 |
| 9:52 | 31.2 | 608.7 | 2.6 | 6.1 | 32.7 | 863.6 | 7.5 |
| 9:53 | 31.7 | 608.9 | 2.6 | 6.1 | 32.8 | 863.6 | 7.4 |
| 9:54 | 31.2 | 608.7 | 2.6 | 6.1 | 33.1 | 863.5 | 7.5 |
| 10:05 | 31.9 | 612.1 | 2.6 | 6.0 | 33.4 | 863.8 | 7.4 |
| 10:07 | 32.0 | 608.2 | 2.6 | 6.0 | 68.5 | 864.0 | 7.9 |
| 10:15 | 30.7 | 604.4 | 2.6 | 6.0 | 67.5 | 864.7 | 7.6 |
| 10:30 | 30.7 | 605.8 | 2.6 | 6.0 | 67.4 | 863.6 | 7.1 |
| 10:40 | 32.4 | 607.0 | 2.6 | 6.0 | 65.0 | 863.5 | 5.9 |
| 10:50 | 31.5 | 603.2 | 2.6 | 6.0 | 66.3 | 863.7 | 6.2 |
| 11:05 | 31.6 | 608.6 | 2.6 | 6.0 | 67.0 | 863.9 | 6.8 |
| 11:12 | 30.8 | 605.7 | 2.6 | 6.0 | 96.6 | 863.6 | 6.2 |
| 11:14 | 31.6 | 603.5 | 2.6 | 6.0 | 96.6 | 863.2 | 6.8 |
| 11:30 | 31.4 | 606.0 | 2.6 | 6.1 | 95.7 | 864.2 | 7.2 |
| 11:40 | 31.7 | 605.2 | 2.6 | 6.3 | 95.8 | 863.4 | 7.8 |
| 11:50 | 32.1 | 599.9 | 2.6 | 6.4 | 95.8 | 864.0 | 9.6 |
| 12:00 PM | 31.4 | 601.7 | 2.6 | 6.4 | 95.9 | 863.8 | 9.1 |
| 12:13 | 31.3 | 606.3 | 2.6 | 6.4 | 96.1 | 863.9 | 8.6 |
| 12:29 | 32.5 | 605.5 | 2.6 | 6.5 | 96.0 | 863.6 | 9.3 |
| 12:30 | 32.1 | 605.8 | 2.6 | 6.5 | 95.9 | 863.5 | 9.6 |
| 12:46 | 31.4 | 603.7 | 2.6 | 6.5 | 94.9 | 864.1 | 9.2 |
| 12:58 | 31.5 | 602.5 | 2.6 | 6.6 | 91.1 | 864.0 | 9.1 |
| 1:25 | 34.3 | 611.7 | 2.6 | 6.5 | 0.0 | 863.9 | 14.3 |
| 1:31 | 33.6 | 620.6 | 2.6 | 6.6 | 0.0 | 863.7 | 10.8 |
| 1:34 | 33.3 | 621.6 | 2.6 | 6.6 | 0.0 | 863.6 | 10.4 |

Wet end sampling and testing procedures remained the same as Trials 6 and 7. For the most part, the results, summarized in Table 26B, were predictable. The temperature of the whitewater dropped about 2° C. when pepsin solubilized collagen was added to the system. The whitewater pH remained between 6.8 and 7.3 throughout the trial.

First pass retention with pepsin solubilized collagen was as good as with APC's polymer retention aid, ranging from 83 to 87%. The BOD of the whitewater stream remained constant throughout the trial, but this appears to be a worst case scenario, where the BOD is not reduced. In some of the trials, the BOD was reduced during the period of pepsin solubilized collagen addition. The cationic demand results yielded much lower values than had been seen before. The predominantly groundwood furnish may have been responsible, because the cationic demand varies from furnish to furnish. As the pepsin solubilized collagen addition rate increased, the cationic demand decreased. This was expected, as was the fact that the pepsin solubilized collagen samples with the highest addition rate gave approximately the same result as the samples containing APC's polymer retention aid. In previous trials, run at the higher pepsin solubilized collagen flow rates, the cationic demand was the same for both the pepsin solubilized collagen samples and the samples with APC's polymer additive.

slightly lighter and more grey. The second pepsin solubilized collagen sample set was the lightest of any of the sets. The last sample (second control) was nearly as dark as the first sample.

Initially, there were only OCC fines in the whitewater system, thus producing a brown sheet. As time passed, the OCC fines were flushed out of the system and replaced by ONP fines which would produce a grey sheet. This procedure was followed for the first three samples, but the samples got darker again towards the last half of the trial, before changing back to their standard 100% OCC furnish. It is possible that the ONP mixture that Putney Paper supplied for the trial did not contain a consistent amount of OCC throughout. The pulp may have averaged between 20 and 25% OCC, but could have varied from 15 to 30% OCC thus yielding inconsistent colors and test results. Most of the strength properties for the pepsin solubilized collagen samples were in between the two controls, so there was no notable increases in strength.

TABLE 26B

Trial 8 Wet End Summary

| Sample | Whitewater Temperature (C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 8:00 AM | 28.7 | 6.80 | 4046 | 526 | 87.0 | 570 | 3.0 |
| 8:05 | — | — | 3940 | 534 | 86.4 | — | — |
| 8:10 | — | — | 4049 | 548 | 86.5 | 550 | — |
| 8.15 | — | — | 4013 | 552 | 86.2 | — | — |
| 8:20 | 28.4 | 6.79 | 3983 | 539 | 86.5 | 570 | 3.4 |
| 9:40 | 29.0 | 7.11 | 3884 | 613 | 84.2 | 530 | 4.0 |
| 9:50 | — | — | 3874 | 636 | 83.6 | — | — |
| 9:55 | — | — | 3816 | 630 | 83.5 | 480 | — |
| 10:00 | — | — | 3776 | 619 | 83.6 | — | — |
| 10:05 | 28.3 | 7.06 | 3955 | 629 | 84.1 | 510 | 4.0 |
| 10:40 | 27.0 | 6.94 | 3890 | 537 | 86.2 | 500 | 3.5 |
| 10:45 | — | — | 3861 | 539 | 86.0 | — | — |
| 10:50 | — | — | 3785 | 541 | 85.7 | 520 | — |
| 11:00 | — | — | 4060 | 481 | 88.2 | — | — |
| 11:05 | 27.5 | 6.90 | 3833 | 617 | 83.9 | 440 | 3.8 |
| 11:40 | 26.9 | 6.81 | 3829 | 581 | 84.8 | 700 | 3.5 |
| 11:45 | — | — | 3988 | 598 | 85.0 | — | — |
| 11:50 | — | — | 3985 | 611 | 84.7 | 540 | — |
| 11:55 | — | — | 4089 | 631 | 84.6 | — | — |
| 12:00 PM | 26.9 | 6.67 | 3965 | 628 | 84.2 | 510 | 3.3 |
| 1:25 | 27.3 | 7.25 | 3891 | 571 | 85.3 | 560 | 3.4 |
| 1:33 | — | — | 3951 | 575 | 85.4 | — | — |
| 1:34 | — | — | 4071 | 533 | 86.9 | 460 | — |
| 1:35 | — | — | 4026 | 547 | 86.4 | — | — |
| 1:36 | 28.9 | 7.33 | 4011 | 501 | 87.5 | 430 | 3.8 |

Physical testing, summarized in Table 27B, was performed, and each sample set represents the average of three "B" samples. Each of the three "B" samples was tested in duplicate to ensure accuracy. The first and fifth sets of data were the controls run at the beginning and at the end of the trial. The three pepsin solubilized collagen sample sets were compared to the average of the controls. There was not as good a correlation between the controls as with Trial 7. There was a 3-4% difference in machine direction tensile index, a 15% difference in cross machine tensile index and a 6% difference in burst index. To investigate this discrepancy, the color of the sheets was observed. The first set contained the darkest, or "brownest" paper. The first and third sets containing pepsin solubilized collagen were Even though no strength increases were found when the pepsin solubilized collagen was added, there were some positive aspects of this trial. It was proven a predominantly groundwood furnish could be run and still produce a sheet almost as strong as with standard furnish. There were about five breaks (four wet end, one dry end) on the paper machine. The wet end breaks occurred mainly because the ONP does not drain as well on the forming wire, and the sheet entered the press section with too much water in it. Because there was a little experience at running with this much ONP, it was difficult to correct the problem instantaneously.

TABLE 27B

Trial 8 Test Results Summary

| Property | Control: APC Polymer, beginning of trial | pepsin solubilized collagen: 33 gpm added @ Center Screen | pepsin solubilized collagen: 66 gpm added @ Center Screen | pepsin solubilized collagen: 98 gpm added @ Center Screen | Control: APC Polymer, end of trial |
|---|---|---|---|---|---|
| Basis Weight | 32.7 | 31.7 | 31.8 | 31.5 | 33.5 |
| Caliper | 3.6 | 3.5 | 3.6 | 3.5 | 3.9 |
| MD Tensile | 22.2 | 21.8 | 21.1 | 21.6 | 21.9 |
| CD Tensile | 8.8 | 8.5 | 8.8 | 9.5 | 10.4 |
| MD Tensile Index | 74.9 | 76.2 | 73.5 | 75.7 | 72.3 |
| CD Tensile Index | 29.6 | 29.5 | 30.6 | 33.4 | 34.4 |
| Burst | 23.4 | 21.9 | 21.5 | 22.2 | 22.6 |
| Burst Index | 3.03 | 2.93 | 2.87 | 2.98 | 2.86 |
| Porosity | 31 | 54 | 34 | 41 | 44 |
| F. P. Retention | 86.5 | 83.8 | 86.0 | 84.6 | 86.3 |
| BOD | 563 | 507 | 487 | 583 | 483 |
| Cationic Demand | 3.20 | 4.00 | 3.65 | 3.40 | 3.60 |

Note:
Tear testing was not done on these samples due to the inconsistency of the two sets of controls. It was concluded that performing the tear tests would not affect the conclusions drawn from this trial.

The following conclusions were reached: There were negligible increases in machine direction tensile strength when pepsin solubilized collagen was added to the fiber furnish. Burst Index did not increase with the addition of pepsin solubilized collagen. The 75% ONP/25% OCC fiber furnish was equivalent to 100% OCC, in terms of final sheet strength. The color of the sample sheets was not consistent throughout the trial suggesting a variance in the furnish. Main steam decreased significantly (~10–11 down to 7–8) during the time that pepsin solubilized collagen was added. The pepsin solubilized collagen did not affect the BOD of the whitewater stream. Like previous trials, first pass retention was the same with either pepsin solubilized collagen or APC's polymer retention aid, generally ranging from 83 to 87%. The pepsin solubilized collagen appeared to be good quality, with few "fish eyes" present.

There were a few more difficulties. More sheet breaks occurred than in any trial before due to the dramatic increase of ONP in the furnish. However, those problems probably did not affect the final analysis significantly. Using a weaker fiber source should significantly aid the strength enhancement capabilities of pepsin solubilized collagen. As of this date it was planned to use 100% news blank and eucalyptus for future trials.

Example 13B

The objectives of this trial were to produce the pepsin solubilized collagen from ground limed trimmings; and to run an entire trial with a 75% news blank/25% OCC furnish.

Limed splits have been used at all previous trials to produce the pepsin solubilized collagen. Trimmings are a lower cost and lower grade material than the splits. The high percentage of news blank was used in an attempt to find a lower quality fiber source to produce weaker paper for the pepsin solubilized collagen to strengthen.

Standard 30 lb basis weight paper was produced at about 856 fpm on APC's paper machine. Fifty-six hundred (5600) gallons of pepsin solubilized collagen produced from 580 lbs. of limed trimmings ground at the USDA. It was produced in a 9000 gal. mixing tank and from there it was pumped into a 3000 gal. dilution tank (to make a 2×dilution). The pepsin solubilized collagen was pumped from the dilution tank to the center screen to be mixed with the stock before going to the headbox.

The following is a description of the trial. Operating furnish was evaluated and selected (75 to 80% news blank/25% OCC). The machine was stabilized at 6.0 pH with APC's polymer additive. Sample set #1 was taken. Pepsin solubilized collagen flow was started to the center screen at 99 gpm. Sample set #2 was taken, then pepsin solubilized collagen flow was decreased to 50 gpm. Sample set #3 was taken out and APC's polymer additive was pumped back into the system. Sample set #4 was taken.

This was the first trial where the final sheet was primarily ONP. The news blank made up 75 to 80% of the furnish (with the balance being OCC). It was encouraging that the paper machine was able to run as fast as 856 fpm considering the high fines content, which can lead to worse drainage on the wire. The pepsin solubilized collagen produced from the trimmings was poor quality with many small undigested particles present. The pepsin solubilized collagen was given an extra day (~65 hours total time) to react, because trimmings react slower than splits. However, the maximum viscosity at 6 rpm, as measured on a Brookfield Viscometer Model LVF with spindle #3, reached only 50 cps, suggesting that not many of the collagen particles were in solution, or that the material had degraded some. The maximum viscosity at 6 rpm for the pepsin solubilized collagen made from limed splits is generally above 1000 cps after 24 hours.

Table 28B summarizes the data collected by the Measurex system during the trial. There was excellent control over the pH, as it remained between 5.6 and 5.9 throughout the entire trial. The main steam displayed different characteristics than in previous trials. From 8:00 AM to 12:30 PM, the steam increased steadily (4.5–5.0 up to 5.5–6.0). The system did not appear in equilibrium, as the steam usage at the beginning of the trial was much different than the steam usage at the end. The pepsin solubilized collagen did not appear to have any effect on the steam usage for this trial.

Table 29B summarizes the wet end testing during the trial. First pass retention decreased significantly when pepsin solubilized collagen was added. This had not happened during any other trial, thus revealing little interaction between the pepsin solubilized collagen and the fiber furnish. If the retention gets too low, fines will build up in the system and can cause drainage problems on the wire. This would in turn lead to the paper being wetter entering the press section and a greater amount of steam required to dry the sheet.

TABLE 28B

Trial 9 Measurex Data from Paper Machine

| Time | Reel Basis Wt. | Stock Flow | Thick Stock Consistency | Thick Stock pH | Pepsin Solubilized Collagen Flow Rate | Machine Speed | Main Steam |
|---|---|---|---|---|---|---|---|
| 7:15 AM | 33.6 | 601.3 | 2.6 | 5.8 | 0.0 | 856.5 | 6.0 |
| 7:20 | 32.9 | 600.9 | 2.6 | 5.7 | 0.0 | 856.3 | 6.1 |
| 8:00 | 31.0 | 579.4 | 2.6 | 5.8 | 0.0 | 856.4 | 5.0 |
| 8:05 | 31.7 | 582.2 | 2.6 | 5.8 | 0.0 | 856.2 | 4.4 |
| 8:10 | 31.5 | 578.5 | 2.6 | 5.8 | 0.0 | 856.2 | 4.7 |
| 8:16 | 31.8 | 582.8 | 2.6 | 5.8 | 0.0 | 856.3 | 4.2 |
| 8:20 | 31.3 | 579.7 | 2.6 | 5.8 | 0.0 | 856.4 | 5.0 |
| 8:49 | 30.9 | 579.5 | 2.6 | 5.9 | 98.6 | 856.4 | 4.8 |
| 8:50 | 30.6 | 583.3 | 2.6 | 5.9 | 99.4 | 856.2 | 4.7 |
| 9:00 | 30.9 | 586.7 | 2.6 | 5.8 | 98.5 | 856.3 | 4.5 |
| 9:23 | 31.6 | 583.5 | 2.6 | 5.8 | 94.9 | 856.2 | 5.0 |
| 9:31 | 31.0 | 584.4 | 2.6 | 5.8 | 94.9 | 856.2 | 4.6 |
| 9:45 | 31.6 | 581.6 | 2.6 | 5.8 | 94.5 | 856.4 | 5.4 |
| 9:54 | 31.5 | 582.7 | 2.6 | 5.8 | 94.2 | 856.2 | 5.5 |
| 9:56 | 31.4 | 585.9 | 2.6 | 5.8 | 95.1 | 856.3 | 5.3 |
| 10:02 | 31.5 | 588.4 | 2.6 | 5.8 | 95.3 | 856.3 | 4.8 |
| 10:06 | 31.1 | 587.8 | 2.6 | 5.8 | 95.0 | 856.3 | 5.5 |
| 10:35 | 31.3 | 581.8 | 2.6 | 5.7 | 49.6 | 856.3 | 5.8 |
| 10:40 | 31.3 | 582.4 | 2.6 | 5.7 | 49.8 | 856.4 | 5.1 |
| 10:51 | 31.9 | 582.7 | 2.6 | 5.7 | 50.3 | 856.4 | 5.6 |
| 11:20 | 32.3 | 589.1 | 2.6 | 5.6 | 0.0 | 856.6 | 5.6 |
| 12:01 PM | 31.6 | 573.4 | 2.6 | 5.7 | 0.0 | 856.3 | 5.5 |
| 12:11 | 31.4 | 574.5 | 2.6 | 5.7 | 0.0 | 856.4 | 6.2 |
| 12:19 | 32.1 | 576.3 | 2.6 | 5.6 | 0.0 | 856.4 | 6.2 |
| 12:26 | 31.4 | 577.5 | 2.6 | 5.6 | 0.0 | 856.5 | 5.7 |
| 12:31 | 31.8 | 579.8 | 2.6 | 5.6 | 0.0 | 856.4 | 6.3 |

When the retention dropped from 85%, using APC's polymer additive, down to 75%, with the pepsin solubilized collagen, the whitewater consistency nearly doubled (527 to 1000 mg/l). The increased fines in the whitewater did not affect its BOD, as most results ranged from 450 to 490 mg/l regardless of the additive.

It was important to look at the retention results when analyzing the physical test results, summarized in Table 30B. Basis weight, caliper, tear and cross direction tensile index did not change significantly when pepsin solubilized collagen was added. Burst index showed only a slight increase of 5%. However, there was a 10.5% increase in

TABLE 29B

Trial 9 Wet End Summary

| Sample | Whitewater Temperature (°C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 8:00 AM | | | 3802 | 581 | 84.7 | 530 | 3.8 |
| 8:05 | | | 3664 | 567 | 84.5 | | |
| 8:10 | | | 3673 | 524 | 85.7 | 490 | |
| 8:15 | | | 3659 | 513 | 86.0 | | |
| 8:20 | 32.8 | 6.56 | 3658 | 493 | 86.5 | 486 | 3.5 |
| 8:40 | | | 4078 | 1100 | 73.0 | | |
| 8:43 | | | 3886 | 1108 | 71.5 | | |
| 9:45 | | | 4038 | 951 | 76.4 | 488 | 3.4 |
| 9:50 | | | 3961 | 912 | 77.0 | | |
| 9:55 | | | 902 | 939 | 75.9 | 482 | |
| 10:00 | | | 4073 | 918 | 77.5 | | |
| 10:05 | 30.2 | 5.99 | 3930 | 1046 | 73.4 | 485 | 3.5 |
| 10:35 | | | 3979 | 1078 | 72.9 | 462 | 4.1 |
| 10:40 | | | 4051 | 1025 | 74.7 | | |
| 10:45 | | | 4031 | 1000 | 75.2 | 443 | |
| 10:50 | | | 4084 | 1022 | 75.0 | | |
| 10:55 | 31.7 | 6.77 | 3991 | 1111 | 72.2 | 493 | 4.0 |
| 12:10 PM | | | 3443 | 503 | 85.4 | 423 | 3.1 |
| 12:15 | | | 3520 | 510 | 85.5 | | |
| 12:20 | | | 3455 | 539 | 84.4 | 462 | |
| 12:25 | | | 3530 | 494 | 86.0 | | |
| 12:30 | 32.8 | 6.82 | 3598 | 545 | 84.9 | 486 | 3.0 | machine direction tensile index. This may be the result of low first pass retention. The control samples contained more fines, which contribute little to sheet strength. The pepsin solubilized collagen samples had less fines and a greater percentage of "quality" fibers that do contribute to sheet strength. Therefore, the pepsin solubilized collagen samples should have greater strength than the samples containing APC's additive. It was difficult to determine how much of the strength increase was due to the fines/fiber composition and how much was due to the pepsin solubilized collagen interaction with the fibers. All the samples had low porosity results (the sheets were more porous). The pepsin solubilized collagen samples were slightly more "closed", suggesting they did not drain as well on the wire.

TABLE 30B

Trial 9 Test Results Summary

| Property | Control: APC polymer - beginning of trial | Pepsin Solubilized Collagen: 99 gpm @ center screen | Pepsin Solubilized Collagen: 50 gpm @ center screen | Control: APC polymer - end of trial |
|---|---|---|---|---|
| Basis Weight | 31.6 | 31.0 | 31.2 | 31.3 |
| Caliper | 4.0 | 4.1 | 4.2 | 3.9 |
| MD Tear | 34 | 34 | 34 | 35 |
| CD Tear | 43 | 44 | 44 | 43 |
| MD Tear Index | 66 | 68 | 67 | 69 |
| CD Tear Index | 84 | 88 | 86 | 85 |
| MD Tensile | 16.6 | 18.3 | 18.4 | 17.0 |
| CD Tensile | 7.6 | 7.7 | 7.6 | 7.7 |
| MD Tensile Index | 58.1 | 65.4 | 65.4 | 60.3 |
| CD Tensile Index | 26.7 | 27.3 | 27.0 | 27.3 |
| Burst | 19.7 | 20.3 | 20.1 | 19.2 |
| Burst Index | 2.63 | 2.77 | 2.73 | 2.60 |
| Porosity | 12 | 16 | 20 | 14 |
| F. P. Retention | 85.5 | 76.0 | 74.0 | 85.2 |
| BOD | 502 | 485 | 466 | 457 |
| Cationic Demand | 3.65 | 3.45 | 4.05 | 3.05 |

The following conclusions were reached: Machine direction tensile index increased 10.5% when pepsin solubilized collagen was added. Burst index increased ~5% when pepsin solubilized collagen was added. Overall sheet strength was 10 to 20% less with 75 to 80% news blank in the furnish. This was the first trial where the furnish was "poor" quality. First pass retention with pepsin solubilized collagen, produced from limed trimmings, was very low compared to that of APC's polymer additive (85% to 75%) and may have contributed to the machine direction tensile strength increase. The BOD was not affected by the pepsin solubilized collagen addition (and the subsequent increase of fines in the whitewater system). The limed trimmings produced a poor pepsin solubilized collagen batch. There were many undigested particles present, even though the reaction took place for ~65 to 70 hours.

The limed trimmings did not digest quickly or thoroughly. Because of this, they had little effect on the system. The news blank contains a higher content of fines than OCC, so it is imperative that a good quality pepsin solubilized collagen batch is produced so that retention results remain high. Limed splits will be used again because it is better known how they will digest.

Example 14B

The objectives of this trial were to run the entire trial with the greatest amount of ONP possible (90+%); and to demonstrate a significant increase in machine direction tensile strength when pepsin solubilized collagen is added.

Standard 30 lb. basis weight paper was produced at 871 gpm on APC's paper machine. Over seven thousand (7350) gallons of pepsin solubilized collagen were produced from 660 lbs. of limed splits ground at the USDA. It was produced in a 9000 gal. mixing tank where it was pumped into a 3000 gal. dilution tank (to make a 2×dilution). The pepsin solubilized collagen was pumped from the dilution tank to the machine chest where it mixed with the thick stock (for about 15 min.) before reaching the headbox.

This was the first trial where conditions were reached that were not runnable. The 95% news blank furnish was able to run until APC's polymers were taken out. With no additives in the system, the fines retention and drainage worsened and the dry line reached the couch. The sheet broke, because it was too wet going into the press section. To help regain the sheet, 96 gpm pepsin solubilized collagen was pumped to the center screen. This added more water going to the wire, but it failed to move the dry line back. Pumping APC's polymer back into the system also failed to affect the dry line. It was decided to continue the trial with more OCC in the furnish so that the furnish would be more runnable. To minimize the number of sheet breaks, it was decided to add the pepsin solubilized collagen to the machine chest rather than the center screen. This would allow less water onto the wire and would not adversely affect the dry line. Furnishes high in ONP or mechanical pulps do not drain as well on the wire, so it was critical to minimize the amount of water going to the headbox.

The following is a summary of the trial. Approximately ~95% news blank furnish, at 6.0 pH, with normal APC polymer additive flows was used. Sample set #1 was taken then, APC's polymer additive flow was cut off. One foot of dry line at first, then the dry line reached the couch where a wet end break occurred. Pepsin solubilized collagen flow was started to the center screen at 96 gpm to try to regain the sheet and move the dry line back. The pepsin solubilized collagen flow was lowered to 60 gpm because too much water was on the forming wire. APC's polymers were turned back on, but we were still unable to restart with pepsin solubilized collagen and APC's polymers. Pepsin solubilized collagen flow was turned off. A decision was made to continue trial at ~80% news blank. A rope break occurred on dryers. Sampling began again (sample set #2—Control #2). The furnish was ~80% news blank, at 6.0 pH, with twice normal APC polymer flows. Pepsin solubilized collagen was pumped to machine chest at 99.9 gpm (50.5 gpm from mixing tank to make a 2×dilution). APC polymer was cut flow by 50% (back to normal flow). A break occurred at second press, but the dry line was intact. Pepsin solubilized collagen flow was cut to 75 gpm (38 gpm from mixing tank). APC polymer flow was cut to about 20%. Sample set #3 was taken. Pepsin solubilized collagen flow was turned up to 100 gpm to empty the tank.

This was a critical trial, because a furnish was selected that without a retention aid could not run. The 95% news blank furnish ran well with APC's polymer additives, but within 10–15 minutes of removing them the drainage on the wire decreased to the point where the dry line reached the couch. Once the machine was running again, an 80/20 furnish was used. To compare the two furnishes, all the data taken throughout the trial was saved.

Table 31B summarizes the data collected by the Measurex process control system. Because pepsin solubilized collagen was added to the machine chest instead of the center screen, its effects can be seen in Table 31B. The pH of the thick stock dropped from 5.9–6.0 to 4.5, when the pepsin solubilized collagen flow was close to 100 gpm. The pH came back up to 4.8 when the flow was decreased to 75 gpm. The pH drop should not have contributed significantly to the strength of the sheet. Trial 5 results showed that a pH drop from 7.0 to 5.0 displayed minimal tensile strength increases (<5%). The basis weight control remained consistent even when the thick stock flow increased because of a decrease in consistency. Main steam pressure displayed a consistent and significant decrease from 9–10 down to 7–8 psi during the period of pepsin solubilized collagen addition. The main steam was ~6 when the furnish was 95+% news blank, but increased when the OCC content increased.

retention characteristics. It was difficult to see the full extent of the retention capability since APC's polymers were being pumped into the system at about 20% of their typical flow. The second set of data (second control) showed very good retention, but twice the normal amount of APC's polymers were used. The first pass retention would have most likely been closer to 80–85%, rather than 90%, if the polymer flows had not been doubled. All of the BOD results were comparable throughout the trial at about 500 mg/l. Because of the two different furnishes run and the pH drop, it was difficult to interpret the cationic demand results.

TABLE 31B

Trial 10 Measurex Data from Paper Machine

| Time | Reel Basis Wt. | Stock Flow | Thick Stock Consistency | Whitewater pH | Pepsin Solubilized Collagen Flow Rate | Machine Speed | Main Steam Pressure |
|---|---|---|---|---|---|---|---|
| 9:30 AM | 32.7 | 607.8 | 2.60 | 6.0 | 0.0 | 870.2 | 5.9 |
| 9:35 | 32.0 | 603.0 | 2.60 | 6.0 | 0.0 | 869.9 | 6.4 |
| 9:39 | 31.3 | 605.7 | 2.59 | 6.0 | 0.0 | 870.2 | 6.2 |
| 9:44 | 31.4 | 606.7 | 2.57 | 5.9 | 0.0 | 869.9 | 6.6 |
| 9:48 | 32.4 | 607.1 | 2.57 | 5.9 | 0.0 | 869.8 | 6.9 |
| 10:41 | 31.0 | 630.2 | 2.42 | 6.1 | 0.0 | 874.0 | 4.8 |
| 2:59 PM | 32.5 | 620.1 | 2.60 | 6.0 | 0.0 | 871.5 | 10.3 |
| 3:10 | 32.0 | 621.2 | 2.58 | 6.0 | 0.0 | 871.8 | 10.1 |
| 3:13 | 31.8 | 623.2 | 2.59 | 6.0 | 0.0 | 871.7 | 10.4 |
| 3:19 | 32.0 | 623.6 | 2.59 | 6.0 | 0.0 | 871.3 | 9.4 |
| 3:53 | 31.0 | 654.0 | 2.40 | 4.6 | 99.4 | 871.0 | 5.7 |
| 4:12 | 31.9 | 666.8 | 2.39 | 4.5 | 71.9 | 871.2 | 7.8 |
| 4:36 | 32.5 | 653.8 | 2.46 | 4.7 | 74.5 | 871.3 | 8.5 |
| 4:43 | 32.4 | 655.7 | 2.47 | 4.8 | 74.8 | 871.2 | 7.7 |
| 4:48 | 32.8 | 652.7 | 2.47 | 4.8 | 74.7 | 870.6 | 7.6 |
| 4:55 | 32.3 | 653.3 | 2.47 | 4.8 | 75.4 | 871.3 | 7.7 |
| 4:59 | 31.8 | 652.8 | 2.47 | 4.8 | 75.3 | 871.1 | 7.8 |
| 5:06 | 32.0 | 655.5 | 2.45 | 4.8 | 75.6 | 871.2 | 7.2 |
| 5:09 | 31.8 | 654.7 | 2.45 | 4.8 | 76.5 | 871.1 | 7.7 |

Table 32B summarizes the wet end testing throughout the trial. Unlike the previous trial, where pepsin solubilized collagen, made from limed trimmings, had little effect on fines retention, this was a well digested batch that had good

TABLE 32B:

Trial 10 Wet End Summary

| Sample | Whitewater Temperature (C.) | Whitewater pH | Headbox Consistency (mg/l) | Whitewater Consistency (mg/l) | First Pass Retention (%) | Whitewater BOD (mg/l) | Cationic Demand |
|---|---|---|---|---|---|---|---|
| 9:30 AM | | | 3875 | 1086 | 72.0 | 496 | 3.5 |
| 9:35 | | | 3441 | 470 | 86.3 | | |
| 9:40 | | | 3652 | 560 | 84.7 | 521 | |
| 9:45 | | | 3463 | 740 | 78.6 | | |
| 9:50 | 33.9 | 6.23 | 3514 | 534 | 84.8 | 527 | 3.8 |
| 2:55 PM | | | 3402 | 355 | 89.6 | 467 | 3.6 |
| 3:00 | | | 3228 | 323 | 90.0 | | |
| 3:10 | | | 3426 | 323 | 90.6 | 499 | |
| 3:15 | | | 3543 | 334 | 90.6 | | |
| 3:20 | 32.0 | 4.18 | 3364 | 377 | 88.8 | 474 | 1.7 |
| 4:50 | | | 3683 | 636 | 82.7 | 429 | 2.0 |
| 4:55 | | | 3718 | 638 | 82.8 | | |
| 5:00 | | | 3673 | 603 | 83.6 | 576 | |
| 5:05 | | | 3640 | 625 | 82.8 | | |
| 5:10 | 30.7 | 4.46 | 3634 | 648 | 82.2 | 568 | 2.2 |

The physical test results are summarized in Table 33B. Pepsin solubilized collagen containing samples had very encouraging results. Machine direction tensile index was about 22% more than the second control and 19% more than the first. Cross direction tensile index of the pepsin solubilized collagen samples was about 13% greater than the two controls. A more significant increase was noted in burst index, where the pepsin solubilized collagen samples were 40% stronger over the first control and 26% stronger over the second. The overall strength of the pepsin solubilized collagen samples was comparable to the 100% OCC sheet. APC's polymers were present in the pepsin solubilized collagen samples at 20% their normal level, but did not contribute to the strength of the sheet because they are retention aids. They most likely contributed a small amount to the retention values.

TABLE 33B

Test Results Summary

| Property | 1st Control | 2nd Control | Pepsin |
|---|---|---|---|
| Caliper | 4.7 | 4.2 | 4.1 |
| MD Tear Index | 65 | 87 | 80 |
| CD Tear Index | 82 | 112 | 99 |
| MD Tensile Index | 59.9 | 58.4 | 71.4 |
| CD Tensile Index | 26.2 | 26.4 | 29.8 |
| Burst Index | 2.29 | 2.55 | 3.22 |
| Porosity | 16 | 11 | 18 |
| F.P. Retention | 81.3 | 89.9 | 82.8 |
| BOD | 515 | 480 | 524 |
| Cationic Demand | 3.65 | 2.65 | 2.10 |

1st Control: 95% ONP/5% OCC, normal Betz polymer flow
2nd Control: 80% ONP/20% OCC, 200% Betz polymer flow
pepsin solubilized collagen: 80% ONP/20% OCC, 20% Betz polymer flow, 75 gpm of 2 × dil. pepsin solubilized collagen to the machine chest The following conclusions were reached. The following strength increases were noted when pepsin solubilized collagen was added to the system: MD tensile index+20%; CD tensile index+13%; Burst index+25-40%. Overall sheet strength of the pepsin solubilized collagen samples was comparable to that of 100% OCC 30 lb. paper typically supplied by APC. Main steam pressure decreased about 20% when pepsin solubilized collagen was added. (The pepsin solubilized collagen samples were compared to the second set of controls since the same furnish was used in both cases. The first control was not used for this comparison because a greater portion of news blank was in the furnish contributing to a lower steam pressure needed to dry.) APC's paper machine cannot be run at 95+% news blank with no retention aid present. The batch of pepsin solubilized collagen appeared to be the best to date. The collagen was well digested and "smoother" than previous batches.

This was the first trial where conditions were achieved at which the furnish became unrunnable. Because of this, there was more difficulty in controlling the process. Much was learned about the optimal conditions under which to use pepsin solubilized collagen. As weaker and weaker furnishes were used, this type of trial was an inevitable step in finding a poor furnish that pepsin solubilized collagen could upgrade and make runnable.

Example 15B

Effect of Soluble Collagen Addition to Paper Made from Eucalyptus Pulp

Solubilized collagen solution was prepared as described in Example 8A and collected after approximately 20 hours to yield a collagen solution with approximately 3.5 mg collagen solids/ml. Pulp slurries were prepared from ONP, OCC and eucalyptus paper stocks at 3% consistency by shredding the materials, soaking them in 1% NaOH overnight (or not soaking them, as indicated in Table 34B), rinsing the soaked solids in tap water, and pulping the rinsed solids in a Tappi disintegrator for 15 minutes.

Pulp suspensions were adjusted to pH 4.0 and diluted to a consistency of approximately 0.5%, to which either no soluble collagen (0%) or 0.5% or 1.0% collagen solids were added (collagen solids/pulp solids×100). Suspensions to which collagen was added were stirred for 15 minutes by a blade-type mixer, at which time paper handsheets were prepared by the methods described in Example 4B. If no soluble collagen was added, handsheets were prepared without mixing for 15 minutes. All samples were equilibrated and tested as described in Example 4B. Results of these experiments are summarized in Table 34B.

The addition of solubilized collagen to the NaOH-soaked eucalyptus fibers resulted in beneficial increases in all of the evaluated properties of the eucalyptus papers, including tear and burst strengths. Without the NaOH treatment, no significant effects were observed in the tensile strength when solubilized collagen was added. Tensile strength increases when solubilized collagen was added were typically in the range of 25% to 50% or more, and were similar to those observed, in the laboratory with handsheets, with NaOH-treated ONP or OCC fibers. Even with the increased strength resulting from the addition of solubilized collagen, however, the eucalyptus papers were considerably weaker than the ONP or OCC papers.

This example demonstrates that addition of solubilized collagen to paper leads to significant increases in strength properties, even for very low strength fibers such as those of recycled pulps, such as ONP or OCC, or soft woods such as eucalyptus or similar pulps. Thus, the beneficial effects for papermaking may lead to a significant increase in the value of such low-valued pulps, particularly if the addition of solubilized collagen allows such pulps to be blended with other fibers/pulps without detracting significantly from the desired mechanical properties of the resultant papers.

TABLE 34B

Summary of Eucalyptus Fiber Investigation Results

| Pulp | % Soluble Collagen | N | Average ΔTS/BW | Average ΔBurst Str. | Average ΔTear Str. |
|---|---|---|---|---|---|
| Group I | | | | | |
| ONP | 0 | 3 | — | did not run | did not run |
|  | 1 | 3 | 40.3 | did not run | did not run |
| OCC | 0 | 3 | — | did not run | did not run |
|  | 1 | 3 | 55.3 | did not run | did not run |
| Eucalyptus[1] | 0 | 5 | — | did not run | did not run |
|  | 0.5 | 5 | 2.3 | did not run | did not run |
|  | 1 | 5 | 4.2 | did not run | did not run |
| Group II | 0 | 8 | — | did not run | did not run |
|  | 0.5 | 5 | 52.8 | did not run | did not run |
|  | 1 | 5 | 68.5 | did not run | did not run |
| Group III | 0 | 10 | 00 | — | — |
|  | 1 | 11 | 25.7 | 30.3 | 46.1 |

N = Number of samples tested per sample set; all other definitions are as defined in Example 3A.
[1]This sample set was not soaked overnight in 1% NaOH; all other sample sets were soaked overnight in 1% NaOH before pulping.

Example 16B

Prophetic Example of Use of Solubilized Collagen for Papermaking Based on Summary of Experience in Trials (Examples 5B–14B)

Based on the extensive experience with the addition of solubilized collagen to an approximately 60 ton/day papermaking process, summarized in Examples 5B–14B herein, we conclude that beneficial addition of solubilized collagen can be achieved at large scales of production. Such beneficial use of solubilized collagen should be especially obtained when short- or weak-fiber pulps, such as ONP or short pulp fibers such as eucalyptus, comprise a significant proportion of the paper furnish. Beneficial properties should result in the increase in tensile and burst strengths, permitting the use of such papers at lower basis weight or in applications where higher-valued pulps are typically required. In addition to increased paper strength, certain improvements in machine performance should be also be observed when solubilized collagen is added to the process. For example, solubilized collagen appears to act as a retention aid, permitting higher recovery of pulp fines and higher paper machine speeds. In addition, higher drainage rates due to the addition of solubilized collagen should result in decreased steam usage in the dryer section of the paper machine and/or higher processing rates. Furthermore, the addition of solubilized collagen appears to decrease BOD values in process whitewater, suggesting that more BOD-contributing soluble organic materials are retained in the paper, thereby reducing effluent concentrations of such materials.

Based on the experience summarized above, we believe that addition of collagen solids derived from hide by-products or the like, for example, by enzymatic hydrolysis will lead to tensile strength increases of 10% to 30% when compared to typical paper strengths obtained by commercially available polymeric paper additives. Preferred embodiments of this invention would result from the addition of approximately 0.2% to 1.0% of the soluble collagen solids, most preferably 0.5% or less, compared to pulp solids. The preferred pH of addition of the solubilized collagen results when the final pulp suspension pH is in the acidic range of 4.0 to 7.0, preferably between 5.5 and 6.5. Greater enhancement in paper physical properties are generally observed when short pulp fibers are used, such as when recycled ONP or eucalyptus fiber is used. Preferred furnish compositions of ONP such as newsblank for example, when mixed with stronger fiber such as virgin kraft or OCC for example, are in the range of 80% ONP to 95% ONP, with most preferred compositions having more than 90% ONP or lower-strength pulps.

Thus, for the paper machine employed in the investigations summarized in Examples 5B–14B, we believe that optimal enhancement of paper properties for recycled ONP would result from the use of furnish pulp having approximately 90% ONP fiber and 10% OCC, and with 0.5% solubilized collagen solids, on a dry weight basis added to the process at a final pulp pH of approximately 6.0. On the paper machine employed, machine speeds exceeding 850 ft/min will be possible with first-pass retention of pulp solids exceeding 85%. Under these conditions, paper tensile strength in the machine direction will be approximately 15% to 20% greater than papers made with normally employed synthetic polymers added as retention aids, etc.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A collagen strengthened cellulosic product made by a process comprising:
   a. adding soluble collagen solids having a number average molecular weight of at least 300,000 daltons to a cellulosic pulp slurry in a paper machine in an amount of about 0.2% to about 1.0% soluble collagen solids as compared to pulp solids and at a pH of addition of about 4.0 to 7.0 based on the final pulp slurry pH;
   b. mixing said soluble collagen and said slurry to form a collagen/pulp slurry;
   c. forming a cellulosic product of desired shape from said collagen/pulp slurry; and
   d. drying said product.

2. A product as set forth in claim 1, wherein said cellulosic pulp slurry comprises short pulp fibers.

3. A product as set forth in claim 2, wherein said pulp slurry comprises about 80% to about 95% ONP.

4. A product as set forth in claim 3, wherein said pulp slurry comprises greater than 90% ONP.

5. A product as set forth in claim 1, wherein said ONP comprises newsblank mixed with stronger fibers.

6. A product as set forth in claim 2, wherein said pulp slurry comprises about 90% ONP and about 10% OCC.

7. A product as set forth in claim 2, wherein said short pulp fibers comprises eucalyptus fiber.

8. A collagen strengthened cellulosic product made by a process comprising:
   a. adding soluble collagen solids having a number average molecular weight of at least 300,000 daltons to a cellulosic pulp slurry in a paper machine, wherein said soluble collagen is added in an amount of about 0.5% soluble collagen solids as compared to pulp solids and said cellulosic pulp slurry is comprised of about 90% ONP fiber and about 10% OCC, and said addition is at a pH of addition of about 6.0 based on the final pulp slurry pH;
   b. mixing said soluble collagen and said slurry to form a collagen/pulp slurry;
   c. forming a cellulosic product of desired shape from said collagen/pulp slurry; and
   d. drying said product.

9. A product as set forth in claim 8, wherein said cellulostic product is a cellulosic sheet.

10. A product as set forth in claim 8, wherein machine direction tensile strength of the resultant cellulosic sheet is about 15% to about 20% greater than that obtained with normally employed synthetic polymers employed as retention aids.

* * * * *